(12) United States Patent
Karlovich

(10) Patent No.: US 11,311,448 B2
(45) Date of Patent: *Apr. 26, 2022

(54) MOBILITY ASSISTANCE DEVICE

(71) Applicant: Robert J. Karlovich, San Jose, CA (US)

(72) Inventor: Robert J. Karlovich, San Jose, CA (US)

(73) Assignee: Core Ingenuity Holdings LLC, San Jose, CA (US)

( * ) Notice: Subject to any disclaimer, the term of this patent is extended or adjusted under 35 U.S.C. 154(b) by 158 days.

This patent is subject to a terminal disclaimer.

(21) Appl. No.: 16/826,602

(22) Filed: Mar. 23, 2020

(65) Prior Publication Data
US 2020/0281800 A1 Sep. 10, 2020

Related U.S. Application Data

(63) Continuation of application No. 15/852,706, filed on Dec. 22, 2017, now Pat. No. 10,786,418, which is a
(Continued)

(51) Int. Cl.
*A61H 3/00* (2006.01)
*A61G 5/12* (2006.01)
(Continued)

(52) U.S. Cl.
CPC ............... *A61H 3/008* (2013.01); *A47C 1/00* (2013.01); *A47C 3/20* (2013.01); *A47C 7/02* (2013.01); *A61G 5/02* (2013.01); *A61G 5/041* (2013.01); *A61G 5/0816* (2016.11); *A61G 5/1051* (2016.11); *A61G 5/1059* (2013.01); *A61G 5/124* (2016.11); *A61G 5/128* (2016.11); *A61H 3/04* (2013.01); *A61N 1/0452* (2013.01); *A61N 1/36003* (2013.01); *A63B 22/0235* (2013.01); *A63B 69/0064* (2013.01); *A61G 5/08* (2013.01); *A61G 2203/14* (2013.01); *A61H 2003/007* (2013.01); *A61H 2003/043* (2013.01); *A61H 2003/046* (2013.01); *A61H 2201/0161* (2013.01); *A61H 2201/0165* (2013.01); *A61H 2201/0192* (2013.01);
(Continued)

(58) Field of Classification Search
CPC .......... A61H 3/04; A61H 3/008; A61G 5/048; A61G 5/1051; A61G 5/124
See application file for complete search history.

(56) References Cited

U.S. PATENT DOCUMENTS 4,431,076 A * 2/1984 Simpson ................ A61G 5/045
280/250.1
5,538,268 A * 7/1996 Miller ...................... A61H 3/04
280/87.041
(Continued)

Primary Examiner — Hau V Phan
(74) Attorney, Agent, or Firm — Patent PC; Bao Tran

(57) ABSTRACT

A mobility assistance apparatus includes first and second frames positioned on left and right sides of a user; a hinge arm mechanism coupled to the first and second frames; and a securing unit or a walking seat coupled to the frames to transfer at least a portion of the user's body weight from the legs and to transfer weight through the user's hip or pelvis to the first and second frame enabling the user to stand or work for an extended period without requiring the user's arms to hold the frame.

27 Claims, 48 Drawing Sheets

Related U.S. Application Data continuation of application No. 14/327,464, filed on Jul. 9, 2014, now Pat. No. 9,149,408.

(60) Provisional application No. 61/684,505, filed on Aug. 17, 2012.

(51) Int. Cl.

| | |
|---|---|
| *A63B 69/00* | (2006.01) |
| *A61H 3/04* | (2006.01) |
| *A63B 22/02* | (2006.01) |
| *A47C 1/00* | (2006.01) |
| *A47C 3/20* | (2006.01) |
| *A47C 7/02* | (2006.01) |
| *A61G 5/10* | (2006.01) |
| *A61G 5/08* | (2006.01) |
| *A61G 5/02* | (2006.01) |
| *A61G 5/04* | (2013.01) |
| *A61N 1/04* | (2006.01) |
| *A61N 1/36* | (2006.01) |
| *G01S 17/931* | (2020.01) |

(52) U.S. Cl.
CPC .............. *A61H 2201/1633* (2013.01); *A61H 2201/1652* (2013.01); *A61H 2201/5043* (2013.01); *G01S 17/931* (2020.01)

(56) References Cited

U.S. PATENT DOCUMENTS

| | | | | | |
|---|---|---|---|---|---|
| 5,702,326 | A | * | 12/1997 | Renteria | .................. A61H 3/04 135/67 |
| 6,607,202 | B1 | * | 8/2003 | Palmer | ..................... A61H 3/04 135/65 |
| 6,733,018 | B2 | * | 5/2004 | Razon | .................... A61H 3/008 135/67 |
| 7,275,554 | B2 | * | 10/2007 | Mullholand | ........... A61H 3/008 135/67 |
| 7,726,327 | B2 | * | 6/2010 | Battiston | .................. A61H 3/04 135/67 |
| 7,883,483 | B2 | * | 2/2011 | Ido | ......................... B25J 9/0006 601/5 |
| 8,220,465 | B2 | * | 7/2012 | Kudoh | ................... A61H 1/024 128/845 |
| 9,149,408 | B2 | * | 10/2015 | Karlovich | ............. A61N 1/0452 |
| 9,861,549 | B2 | * | 1/2018 | Karlovich | ............. A63B 22/02 |
| 9,913,773 | B2 | * | 3/2018 | Karlovich | ............. A61G 5/124 |
| 10,786,418 | B2 | * | 9/2020 | Karlovich | ............. A61G 5/124 |
| 2001/0048206 | A1 | * | 12/2001 | Niu | ......................... A61H 3/04 280/87.021 |
| 2002/0121755 | A1 | * | 9/2002 | Workman | ................ A61H 3/04 280/87.021 |
| 2005/0236217 | A1 | * | 10/2005 | Koelin | ................... A61G 5/046 180/411 |
| 2009/0186747 | A1 | * | 7/2009 | Lokken | .................. A61G 5/124 482/51 |
| 2010/0270771 | A1 | * | 10/2010 | Kobayashi | ........... A61H 1/0255 280/210 |

* cited by examiner

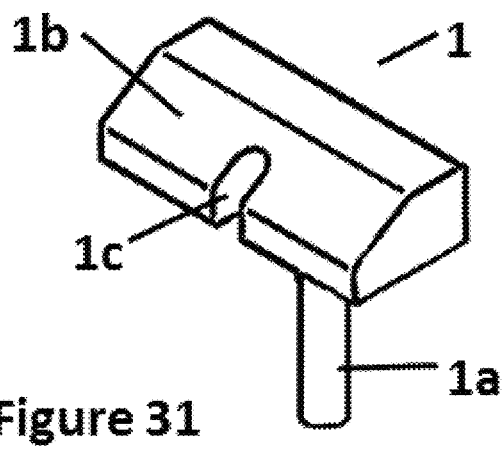
Figure 31
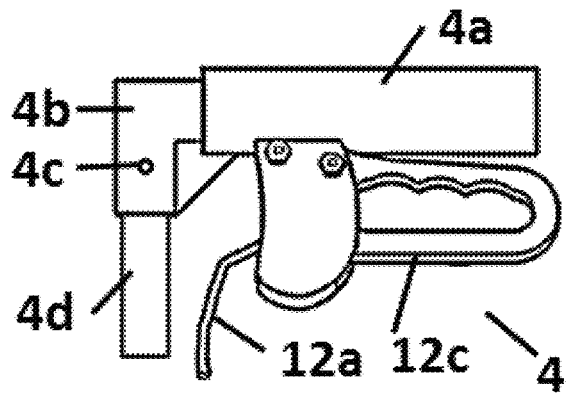
Figure 32
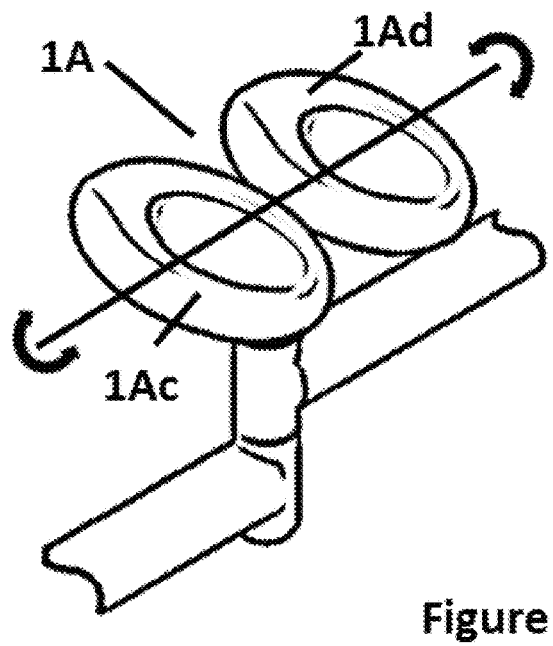
Figure 31a
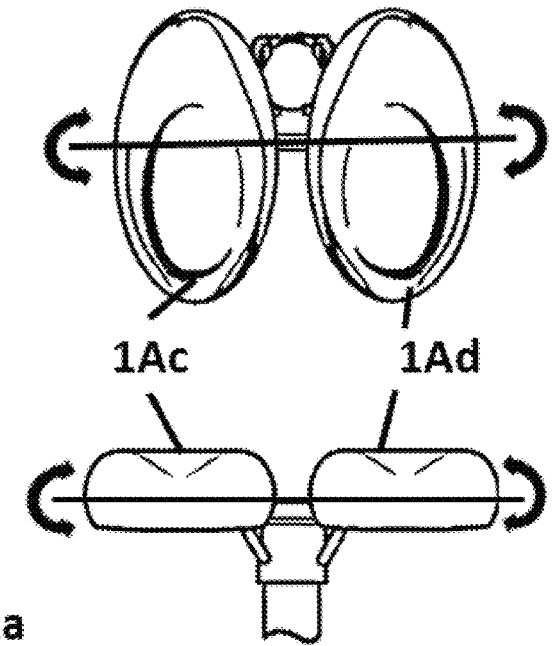

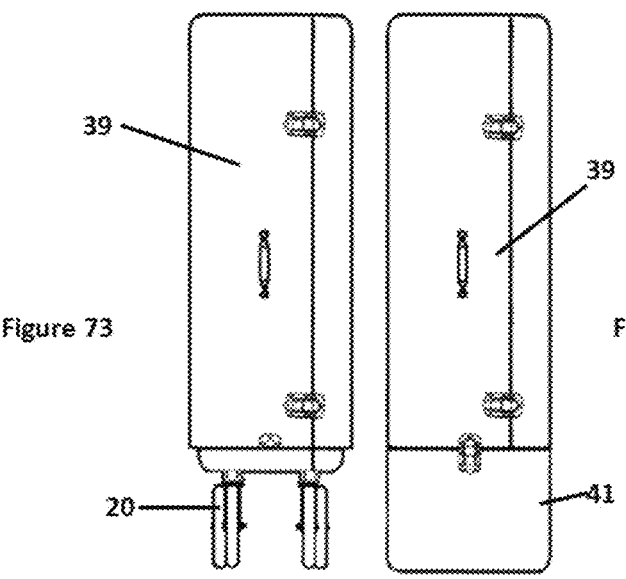
Figure 73
Figure 74
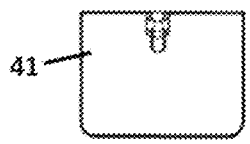
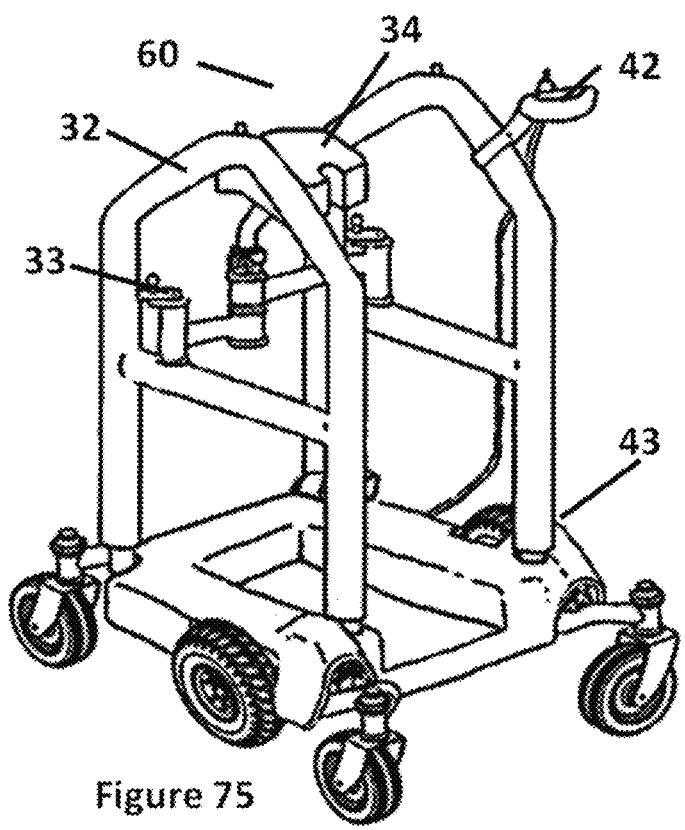
Figure 75

| |
|---|
| Positioning first and second frames on left and right sides of the user with a hinge arm mechanism coupled to the first and second frames including a walking seat positioned on the hinge arm mechanism to receive the person (102) |
| Positioning user on the walking seat and securing the user to the walking seat with a belt (104) |
| Walking while contacting the walking seat for support, wherein the walking seat provides clearance for legs walking in a forward and backward motion (106) |
| Gradually transitioning in position from a mostly seated posture to a fully or nearly fully standing posture over the course of therapy (108) |

Figure 83

MOBILITY ASSISTANCE DEVICE

This application is a continuation of application Ser. No. 15/852,706 which is a continuation in part of application Ser. No. 14/327,464 filed Jul. 9, 2014, which claims priority to Provisional Application Ser. No. 61/684,505, filed Aug. 17, 2012, the content of which is incorporated by reference.

BACKGROUND OF THE INVENTION

The preferred embodiment relates to the field of mobility assistance devices that allow individuals to move from place to place in a standing or partially standing posture.

DESCRIPTION OF THE RELATED ART

Conventional mobility assistance devices used for walking, such as crutches and walkers, typically require an individual to support their body weight alternating (or distributing) between their legs to arms and shoulders. This places stresses on ankle, knee, hip, wrist, elbow and shoulder joints, often times limiting the individuals' ability to use these devices without significant pain or discomfort. Furthermore, because these devices require the individual to use their arms to move about, the individual's arms are not free to use for other purposes. Many of these individuals are forced to use a wheelchair for mobility when they would prefer to stand and move about in a more erect posture.

Additionally, approximately 50% of people with mobility challenges are preclinical. They do not use any mobility assistance device as currently available devices do not address their fundamental need to stand comfortably and safely to accomplish typical tasks of daily living. The mobility devices predominant in the market today generally interfere with the completion of these tasks, not facilitate the user's ability to complete them. The device disclosed in this document allows individuals to accomplish activities of daily living without interference from the device itself. The device addresses the unmet need of preclinical individuals as well as significantly improves on the state of the art for many of the other individuals with more significant challenges standing and moving about.

The disclosed innovations blur the line between a mobility device and furniture. Since a primary objective of the device is to facilitate the completion of everyday tasks, a primary use will be the replacement of chairs in the user's house, office of other locations where the user desires to be.

Furthermore, as scientific study reveals, there are tremendous health benefits for people to avoid excess sitting. Use of the disclosed device to facilitate standing in the proper posture comfortably and safely for extended periods promote the use of this device to be used by the general population at large, not just those with standing and mobility problems. The innovations disclosed in this document will help move society to avoid excess sitting and sedentary behaviors and towards a society that predominantly stands comfortably and safely for extended periods of time.

U.S. Pat. No. 7,828,311 discloses a wheelchair that includes a wheelchair frame, a pair of rear wheels and a pair of front wheels carried by the wheelchair frame, a drive motor drivingly engaging at least one of the pair of rear wheels and the pair of front wheels, a pair of wheelchair tracks detachably carried by the wheelchair frame and a locomotion assist assembly carried by the wheelchair frame.

Remaining in a seated position for extended periods is detrimental to an individual's health, negatively affecting basic body functions including digestive, cardio-vascular, and respiratory systems. Encouraging and enabling an individual to stand, especially if the individual can walk around, can improve these body functions and help avoid deterioration of health. Many individuals become dependent on wheelchairs rather than remaining mobile in an upright posture because there is no practical choice available to them today. Problems with legs, joints and or balance lead individuals to limit or eliminate walking, putting health at risk.

Prosthetic devices can be considered as mobility assistance devices and in the context of this preferred embodiment they are considered complementary. In fact, it is because of the challenges of prosthetics-leg-wearing veterans that motivated the originating work on this preferred embodiment. Prosthetic leg wearers have significant challenges standing and walking for periods of time and suffer in particular because of the stresses on the leg at the juncture of the prosthetic and the limb.

Over-reliance on conventional wheelchairs may aggravate problems with legs, joints or balance, leading users to limit or eliminate walking. As a result, wheelchair-dependent individuals may be putting their health into a potentially accelerating decline as they stop or limit walking and reduce the time spent in standing posture.

SUMMARY OF THE INVENTION

In one aspect, a mobility assistance apparatus includes first and second frames positioned on left and right sides of a user; a hinge arm mechanism coupled to the first and second frames; and a harness coupled to the frames to transfer at least a portion of the user's body weight from the legs and to transfer weight through the user's hip or pelvis to the first and second frame to stand or walk for an extended period without requiring the user's arms to hold the frame.

In another aspect, a mobility assistance apparatus includes first and second frames positioned on left and right sides of a user; a hinge arm mechanism coupled to the first and second frames; and means to remove at least a portion of the user's body weight from the legs and transfer the weight through the hips or pelvis to the first and second frame that does not require the user's arms to stand or walk for periods of time.

In another aspect, a walking assistance apparatus includes first and second frames positioned on left and right sides of a user; a hinge arm mechanism coupled to the first and second frames; and a walking seat positioned on the hinge arm to receive the user at a predetermined point and a belt to secure the user to the walking seat, wherein the walking seat and belt removes weight from the user's legs without requiring the user's arm, and wherein the walking seat has a predetermined shape providing clearance for legs when the user stands, partially stands, or walks for extended periods of time without requiring a wheelchair.

In yet other aspects, systems and methods are disclosed to provide standing and walking assistance to a person by positioning first and second frames on left and right sides of the user with a hinge arm mechanism coupled to the first and second frames including a walking seat positioned on the hinge arm to receive the person; positioning the user on the walking seat and securing the user to the walking seat with a belt, a flip, a grasp or a combination of elements; standing while contacting the walking seat for support, wherein the walking seat provides weight bearing support to comfortable and safe standing for extended periods of time; walking while using a treadmill while contacting the walking seat for support, wherein the walking seat provides clearance for legs moving and a forward and backward motion; and walking while contacting the walking seat for support, wherein the walking seat provides clearance for legs walking in a forward and backward motion.

Implementations of the above aspects may include one or more of the following. The walking seat can consist of two padded seat pans mounted on a seat frame, each supporting the corresponding side of the buttocks, each of which can independently pivot around a horizontal axis while the user walks. The walking seat positions the user's body in the optimal posture to support extended use for standing or walking or standing and using a treadmill. There are several preferred embodiments to secure the use into the device such as a belt and buckle, a flip, a grasp, or a combination thereof. Each frame can have a height adjuster to adjust a frame height to fit the user. The height adjuster can be a manual extender with a core and a plurality of openings to select height, or the height adjuster comprises a motorized extender. The motorized extender can be a linear actuator or a pneumatic pump. The hinge arm mechanism is foldable and can have three hinge points: one on a seat support and two points each to be connected to one of the first and second frames. The frame can have one or more wheels: a front wheel that swivels 360 degrees around a vertical axis and a rear wheel that does not swivel. A brake assembly can stop the one or more wheels and be controlled by the user to stop movement. The wheel(s) can be motorized. The wheel can be a hub wheel motor. A processor can control the motorized wheel. The movement of a paraplegics legs can be driven through FES (functional electrical stimulation). A processor can control the FES electrodes. This can be for walking or for exercise with a treadmill. A joystick can be provided to receive direction command, a display can provide visual feedback, and a processor can be connected to the joystick and the display to guide the user. A smartphone can include an application to provide the same capabilities of the joystick. An obstacle warning system can be provided. Buttons can be provided to select move forward, move backward, turn right, turn left, and brake. A foot rest can be placed on the front bottom of the first or second frame. Other securing systems can be used including harness, belt, sling seat and latching straps. The frame members are of identical design and interchangeable, or they can be different to support the specific needs of a unique individual. The frames and the hinge arm mechanism are collapsible or they can be replaced with a no-collapsible form of a different design for use with a treadmill. A seat height adjuster including an air spring can be used for seat height adjustment. Shock absorbers can be included to smooth out rough surface rides.

In another aspect, a walking assistance apparatus includes first and second frames positioned on left and right sides of the user, each frame further comprising one or more motorized wheels coupling the frame to the ground; a hinge arm mechanism coupled to the first and second frames with a seat-support; a walking seat positioned on the seat-support to receive the user at a predetermined point, wherein the walking seat provides clearance for legs walking in a forward and backward motion; and a belt or other means to secure the user to the walking seat.

Implementations of the above aspect may include one or more of the following. Each frame can have a first wheel that swivels 360 degrees around a vertical axis and a second wheel that does not swivel. A brake assembly can be connected to the one or more wheels and controlled by the user to stop movement. The wheel can be a hub wheel motor. A processor can control the motorized wheel. Other electronics can be used including a joystick to receive direction command, a display to provide visual feedback, and a processor coupled to the joystick and the display to guide the user. An obstacle warning system can help the user navigate. A joystick or buttons can be used to select move forward, move backward, turn right, turn left, and brake. Two seat pans can be mounted on a seat frame, each supporting a corresponding side of the buttocks, each of the seat pans independently pivoting around a horizontal axis while the user walks. Each frame can have a height adjuster to adjust a frame height to fit the user. The height adjuster can be a manual extender with a core and a plurality of openings to select height, or the height adjuster comprises a motorized extender. The motorized extender comprises a linear actuator or a pneumatic pump. The hinge arm is foldable and comprises three hinges: one on the seat support and one each on each of the first and second frames. A foot rest can be provided at the bottom of the frame. The device can include a harness, belt, sling seat and latching straps. The frame members are of identical design and interchangeable. The frames and the hinge arm are collapsible. A seat height adjuster including an air spring can be used for seat height adjustment. One or more shock absorbers can smooth out a rough ride. The walking assistance apparatus can provide an assisted walking mode with a user walking with the moving motorized frames.

In a further aspect, a method to provide walking assistance to a person includes positioning first and second frames on left and right sides of the user with a hinge arm mechanism coupled to the first and second frames including a walking seat positioned on the hinge arm mechanism to receive the person; positioning the user on the walking seat and securing the user to the walking seat with a belt; and walking while contacting the walking seat for support, wherein the walking seat provides clearance for legs walking in a forward and backward motion.

Implementations of the above aspect may include one or more of the following. The system allows in selecting an assisted walking mode with the person walking with the moving motorized frames or alternatively using FES actuation of the user's legs or a combination of motorized frame and FES actuation of the user's legs. Wheels can be used to support ambulation. The method includes providing one each frame a first wheel that swivels 360 degrees around a vertical axis and a second wheel that does not swivel. The system can embed a motor in a wheel. The system could connect with electrodes in the user's legs. The method includes controlling a brake assembly coupled to the one or more wheels to stop movement. The method further includes controlling a motorized wheel with a processor, a portable computer, a table, or a smart phone. The system can receive a direction command with buttons or a joystick and displaying visual feedback to the person. The method includes warning of obstacle(s). The method includes selecting a command to move forward, move backward, turn right, turn left, or brake. The system can include a walking seat having a pair of seat panels extending from each seat support frame, and wherein each seat panel is pivotally attached to a corresponding seat support frame. The method includes adjusting a frame height to fit the user. The hinge arm is foldable and comprises three hinges: one on the seat support and one each on each of the first and second frames, comprising folding the hinge arm during transportation. The frame members can have identical design and interchangeable, comprising collapsing the frames and the hinge arm during transportation. The user can adjust a seat height. The method includes providing one or more shock absorbers to smooth out a rough ride. The method includes reducing overall depth and width for ease of transportation. The method further includes swiveling rear wheel assemblies and front wheel assemblies 180 degrees inward towards the center of one frame, and repeating this step in an opposite orientation to reduce overall depth; and folding the hinge arm inward proximally parallel to one side frames to reduce overall width. The method can be used for treating the person with a therapy. This can be done by gradually transitioning the person in position from a mostly seated posture to a fully or nearly fully standing posture over the course of therapy.

In yet another aspect, a method for performing ambulatory therapy for a patient includes positioning first and second frames on left and right sides of the user with a hinge arm coupled to the first and second frames including a walking seat positioned on the hinge arm to receive the person; positioning the user on the walking seat and securing the user to the walking seat with a belt; walking while contacting the walking seat for support, wherein the walking seat provides clearance for legs walking in a forward and backward motion; and transitioning in position from a mostly seated posture to a fully or nearly fully standing posture over the course of therapy.

Implementations of the above method may include one or more of the following. The method includes starting the therapy at a height that the user's legs project forward from the frames while sitting; and progressively raising a seat height and walking with the device until the user reaches a predetermined vertical standing posture. Therapy can be performed under the direction of a physical therapist or a health professional. The method includes raising a device height in small increments during the therapy. The patient can walk without the frames upon completion of therapy. The patient can walk with the frames and maintaining the final vertical standing posture upon completion of the therapy. Alternatively, the patient can use the method with the device attached to a treadmill to simulate walking. The therapy increases user strength, flexibility. The therapy also increases mobility, strengthening the heart and lungs, and controlling patient weight. The patient can walk with the frames in a hands-free manner. The method includes ambulating in a standing (legs vertical) or partially standing (legs between seated and standing position) posture to reduce stress on ankle, knee, hip, wrist, elbow and shoulder joints or at the interface with a prosthetic leg. The method alternatively includes simulated ambulation in conjunction with a treadmill in a standing (legs vertical) or partially standing (legs between seated and standing position) posture to reduce stress on ankle, knee, hip, wrist, elbow and shoulder joints or at the interface with a prosthetic leg. The method further includes reducing or eliminating dependency on a wheelchair for mobility. The method includes allowing the patient to walk for extended periods. The therapy includes providing support while traversing wheelchair accessible walkways, ramps, paths, rooms and other indoor and outdoor facilities. The user can fold the frames and hinge arm into a compact form for transportation. The treatment includes walking on a treadmill with the frames of a different design from the mobility device. The patient can walk without the device upon completion of the therapy. The patient can also walk with the device in case of a permanent ambulatory disability. The walking seat provides clearance for forward and backward motion of legs walking. The device can provide a surface to support ischial tuberosities (sits bones) and allow transfer of a body weight of the person to the walking seat. A secondary support including a belt or other means can secure the person to the walking seat.

In yet another aspect, a stand and work apparatus includes a treadmill; and a walking assistance apparatus positioned above the treadmill, including: first and second frames positioned on left and right sides of the user; a hinge arm coupled to the first and second frames with a seat-support; a walking seat positioned on the seat-support to receive the user at a predetermined point, wherein the walking seat provides clearance for legs walking in a forward and backward motion; and a belt to secure the user to the walking seat.

Implementations of the above method may include one or more of the following. Two seat pans can be mounted on a seat frame, each supporting a corresponding side of the buttocks, each of the seat pans independently pivoting around a horizontal axis while the user walks. Each frame has a height adjuster to adjust a frame height to fit the user. The height adjuster includes a manual extender with a core and a plurality of openings to select height, or the height adjuster can include a motorized extender. The motorized extender comprises a linear actuator or a pneumatic pump. The hinge arm is foldable and comprises three hinges: one on the seat support and one each on each of the first and second frames. Each frame has one or more wheel: the first wheel swivels 360 degrees around a vertical axis and a second wheel that does not swivel. A brake assembly can be used to brake the one or more wheels. The device includes a harness, belt, sling seat and latching straps. The walker/treadmill can be used for exercising a user by providing a walking assistance apparatus positioned above the treadmill. The exercise includes first and second frames positioned on left and right sides of the user; a hinge arm mechanism coupled to the first and second frames with a seat-support; a walking seat positioned on the seat-support to receive the user at a predetermined point, wherein the walking seat provides clearance for legs walking in a forward and backward motion; and securing by belt or other means the user to the walking seat; and walking on a treadmill. Therapy can be provided. The therapy includes gradually transitioning the person in position from a mostly seated posture to a fully or nearly fully standing posture over the course of therapy. A surface can be provided to support the ischial tuberosities (sits bones) and to transfer a body weight of the person to the walking seat. The therapy includes providing a secondary support including a belt or other means to secure the person to the walking seat. The patient can have sit-bones placed in a vertical orientation. The therapy uses a flatter, angled leading edge for the walking seat.

There are "heavy-" and "light-" weight variations of the motorized option of the device. The heavy-weight device leverages technologies typically used by motorized wheelchairs or one or two wheeled "balancing devices" an example being the Segway. The light-weight device replaces the rear (non-castor) wheel assemblies with independent motor-driven hub wheels. The user places their feet on foot rests off of the ground surface. These are controlled by the user through a joy-stick or smartphone application and controller unit. These motorized versions can include motorized height adjustment features, collision-avoidance sensors, and either an LCD display or an interface for the user's smart phone.

The lightweight motorized version can be used in an "assisted walking mode." In the assisted walking mode the user walks along while the device moves along driven by the hub wheels (and without the foot rests in place). A self-propelled lawnmower is an analogous solution. This can be particularly helpful for an individual during their rehabilitation period while the user gains more strength and capability in the affected leg or when walking unassisted would otherwise prove too difficult (traversing up an inclined walkway, for example). Alternatively, a fifth motor-driven hub wheel can be added to the rear of the non-powered device through an arm that attaches to the rear of the device to provide the propulsion and braking with control a joystick or smartphone application and controller unit.

In another aspect, the device can be used in conjunction with a rehabilitation therapy process. The user transitions over the course of the rehabilitation cycle from a mostly seated posture to a fully or nearly fully standing posture. The user would start with the device in a relatively low setting so that the legs project more forward from the device similar to when sitting in a chair. As the therapy proceeds and the user improves and gains proficiency, the device height is raised in small increments. This process continues until the user assumes as vertical a standing posture as deemed appropriate by the directing health professional. If the user is done with the therapy and no longer requires the device (such as for a surgically repaired knee, for example) the user can resume walking without the device. If the user will continue to require the device to enable walking for the indefinite future (such as for a permanent leg disability, for example), the device will remain more or less at this setting going forward.

In another aspect, as a part of therapy or as a means to otherwise improve posture and health, the device may be used to allow an individual to stand with improved posture, comfort and safety and not for walking. The user may not be able to or may not want to walk in this case but prefers to use the device simply to receive the health benefits of standing and improved posture. Many people who have been sitting for a prolonged time do not have the correct posture or the capability to do anything more than stand initially. Further, the objective of the therapeutic use for standing may be to correct postural problems or to increase strength of the core or to improve balance. At the appropriate time in therapy, the therapist may choose to have the wheels installed and henceforth work with the user on walking skills. Further, in a rehabilitation setting, the device can be used without wheels in a relatively low setting so the user's legs project more forward from the device similar to when sitting in a chair. As the therapy proceeds and user gains proficiency as well as the postural improvements necessary to stand, the devise height is raised in small increments.

Additionally, the user may use the device for both walking assistance and for standing assistance. The wheels may be either locked into position or completely removed from the device. For example, a person may need to get accustomed to standing before any effort is made to walk. Or, they simply prefer to stand comfortably when they are not walking. The user may also want to remove the wheels to provide a stable base for exercising, cooking or other activities where standing is preferred and walking is not required.

Variations of the preferred embodiment can include: alternative means to distribute weight from the legs (harness versus walking seat and belt); various alternative frame designs and orientations, various walking seat designs, scaled up or down versions to accommodate for body size and weight (children, for example); the use of wheels and use without wheels, motorized versus manual; and optional configurations ("stand-behind" walker mode, transport wheelchair), features and accessories (wheel sizes and types, carrying baskets, shock absorbers, and other configurations).

Advantages of the mobility assistance devices or systems described herein may include one or more of the following. The portable mobility assistance device allows individuals to move about in a standing or partially standing posture supported in a manner that can significantly reduce the stresses and discomfort on ankle, knee, hip, wrist, elbow and shoulder joints or at the interface with a prosthetic leg. The device improves the user's standing posture and gait. The device potentially reduces or eliminates the dependency on a wheelchair for mobility. The device uses the walking seat and belt or the harness to remove weight, up to 100%, from the legs to enable the user to walk or stand. Secure connection is provided with the device so stable that people with balance problems can walk and stand. The device provides for weight removal from the legs and stability over flat or wheelchair accessible ramps for assuring balance so that the person can walk. The device keeps people in a standing or partially standing posture for longer periods of time to provide a health benefit, even if they cannot walk or can only walk with motorized assistance with motorized versions and the walking assistance mode. Because of its compact size, maneuverability, and the standing or partially standing posture of the user, the device can potentially enable the user to avoid costly renovations to house and office that would otherwise be necessary if the user was wheelchair bound. The device frees the arms of the individual to be more available to use for other purposes. The preferred embodiment also provides stable support while traversing wheelchair accessible walkways, ramps, paths, rooms and other indoor and outdoor facilities as well as (when appropriately outfitted) over a variety of other terrain. Additionally, the device is foldable into a compact form and capable of being conveniently transported such as in an automobile trunk or as a checked item for an airplane. The system supports a disabled or elderly person during ambulation or while standing so that he or she can stand, walk or exercise while minimizing risks of falls or injuries related thereto. The mobility provided can reduce the user reliance on the wheelchair. By encouraging the user to stand and walk with aided support by the system, the system reduces causes of skin sores. The system encourages active standing and walking with attendant increased blood flow. Pressure on the buttock is reduced, and blood circulation is enhanced to minimize pressure or skin sores. The device minimizes skin sores as it eliminates prolonged pressure and wetness on the skin.

Other advantages of the mobility assistance device may include one or more of the following. The devices can be foldable which in extended or in use condition affords the comfort and convenience of supporting the disabled or elderly, but which when in folded condition is compact and occupies a side area defined substantially by the diameter of the floor to arm rest height distance. Such area reduction in combination with state-of-the-art width reduction provides a mobility assistance device which is accommodated and transportable within the reduced space available in the newer type smaller automotive vehicles. The foldable device affords side area reduction while retains the relatively low cost and maximum strength and rigidity of unit side frame construction. The device can have means for achieving side area reduction by controllably and automatically shifting the driving wheel axes relative to the side frame from their normal operating positions to place the chair in folded condition. In certain embodiments, the act of extending the chair from folded condition will controllably and automatically reposition the mobility assistance devices to their normal operating positions wherein the frames with wheels are secured for maximum efficiency in operation, balance and stability. The wheels can be removed to be used to assist in standing.

In addition to the ease of use and storage, the system reduces the negative effect of prolonged sitting and maximizes the benefits of standing/walking. Sitting and lying down for extended periods of time is detrimental to an individual's health, negatively affecting many basic body functions including digestive, cardio-vascular, and respiratory systems. Encouraging and enabling an individual to periodically change position to a standing or partially standing posture and especially if the individual can walk around can improve these body functions and help avoid further deterioration of health.

The device is multi-functional and can serve as a conventional walker when used without the belt (or alternative means) and walking seat. The individual can stand behind the device, getting support by holding onto the handles, similar to the conventional walker. The user can use the device with the handles "as is" or, if they prefer, they can also reverse the direction of the handles. The device can easily convert into a wheelchair for times when a user prefers to travel similar to a conventional transport wheelchair. The device can be used as an alternative to sitting by allowing the user to stand comfortably, with or without the wheels installed. By installing the optional foot rests and sling seat and reversing the handles, the device operates as a transport wheelchair.

While the preferred embodiment can specifically help prosthetic-leg wearing veterans, it is expected that it will also satisfy a broader market—includes the larger pool of leg amputees (who may or may not use a prosthetic), sufferers of degenerative joint diseases, as a rehabilitation tool for joint replacement or after leg or joint surgery to repair ligaments, tendons, bone or tissue, as a rehabilitation tool after stroke or brain injury, those who have problems maintaining balance, the elderly or others who suffer significant joint pain and discomfort when standing or walking.

BRIEF DESCRIPTION OF THE DRAWINGS

FIG. 31 shows an exemplary perspective view of walking seat.

FIG. 31a shows exemplary perspective, top and front views alternative walking seat.

FIG. 32 shows an exemplary side view of handle and brake lever.

FIG. 73 shows an exemplary side view of closed travel case with device, separated bottom wheel housing.

FIG. 74 shows an exemplary side view of closed travel case with device, connected bottom wheel housing.

FIG. 75 shows an exemplary perspective view of heavy-weight motorized device 60.

FIG. 83 shows an exemplary treatment process using the above devices.

FIGS. 91-92 show a "capture arm" arrangement that is a combination of the "flip" and "grasp" arrangements.

DETAILED DESCRIPTION

Figure 1:
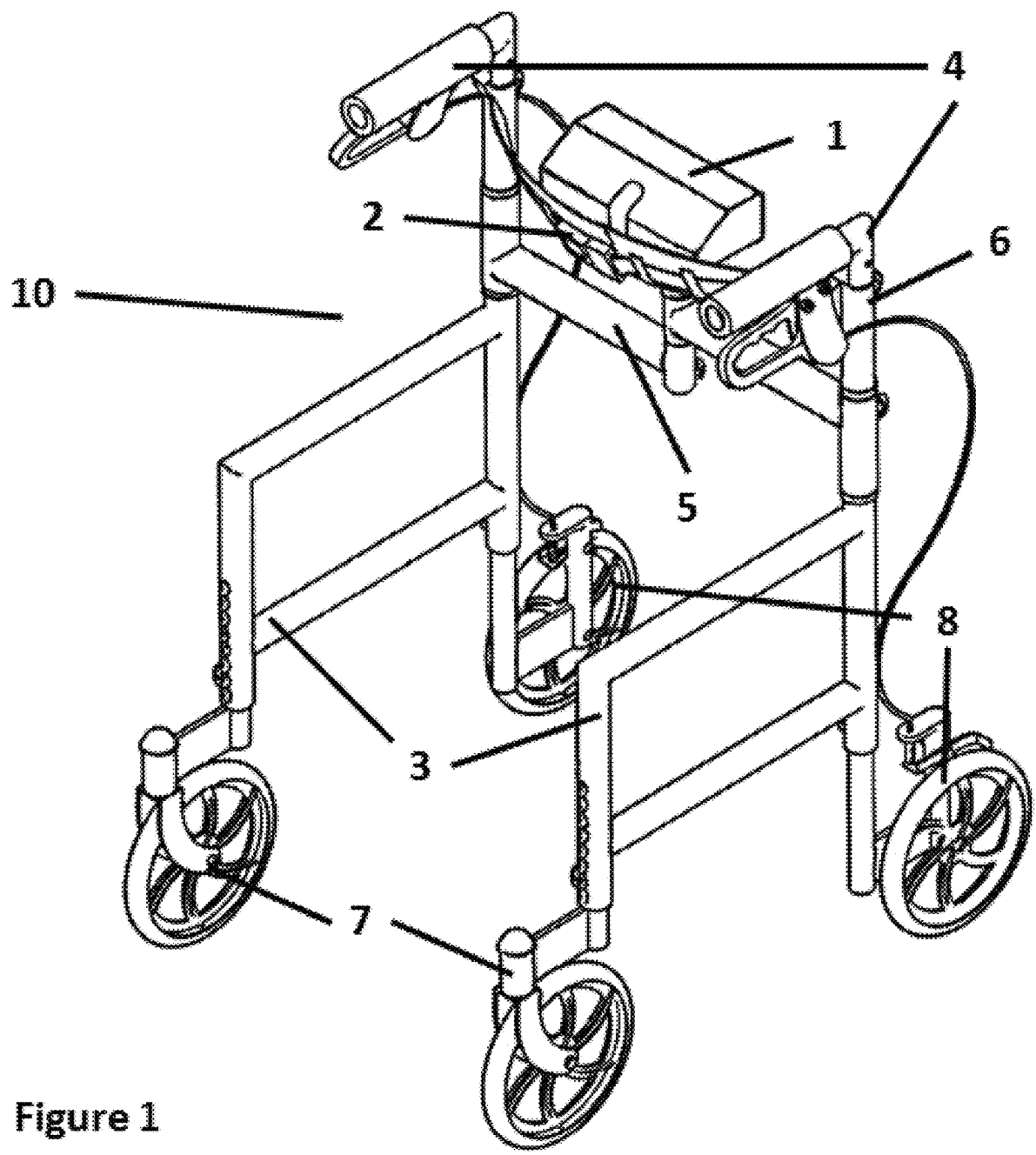
FIG. 1 shows an exemplary perspective view mobility assistance device 10.

Referring to the drawings, an illustrative embodiment of a mobility assistance device is generally indicated by reference numeral 10. Also shown in FIG. 1 are the primary structural components of device 10. These include two side frames 3, two handles 4, a hinge arm mechanism 5, and 2 hinge posts 6. The belt 2 is rigidly attached to handles 4, which connects through the hinge posts 6, to side frames 3 while securing the hinge arm mechanism with seat support frame members 5.

In one embodiment, the device 10 includes a support frame having a pair of generally elongated, parallel, spaced-apart side frames 3. Front wheel assembly 7 is provided on the front of each frame 3. In some embodiments of the device 10, a cam lever rigidly fixes each wheel assembly 7, 8 to the corresponding side frame 3. In one embodiment, the height of the frame member 3 relative to the ground can be controlled by various mechanisms, including the spring buttons and hole features as shown in FIG. 1 or motorized height extenders such as linear motor, as discussed in more details below.

In the embodiment of FIG. 1, a foldable hinge arm mechanism 5 extends in spaced-apart relationship between the respective side frames 3. When fully extended and locking cam levers 11 employed, the hinge arm mechanism 5 fixedly connects the side frames 3 to each other. A seat support extends from the center of the hinge arm mechanism 5.

In one embodiment, the side frames 3 and hinge arm mechanism 5 surround the user. In yet other embodiments, two frames could be in front and behind the user and the user would enter the device laterally in this case.

Referring now to FIG. 1 in more detail, the mobility assistance device 10 includes a walking seat 1 on which the user positions their "sit-bones" and an adjustable belt 2 that, in combination, holds the user firmly in place. A walking seat is a device that primarily differs from a bicycle seat in that it allows for walking while still supporting the user's weight. Unlike a bicycle seat, a walking seat generally requires a belt or other apparatus working in concert with the walking seat to hold the user in position.

The walking seat differs from a bicycle seatin that it does not have a "horn," which would be unbearably uncomfortable if used for walking with device 10. Also, the walking seat positions the sit-bones relatively close to the front edge of the walking seat and therefore does not interfere with the forward and backward motion of the legs while the user is walking. A typical bicycle seat positions the sit-bones towards the back of the seat which does not allow such ease of forward and backward movement to allow walking with a full range of motion. The walking seat 1 can be provided on the seat support 5c of hinge arms 5. The walking seat can consist of either a single padded seat pan 1b mounted on a seat frame, or alternatively two padded seat pans, 1Ac and 1Ad, mounted on a seat frame. In the case of a walking seat with two padded seat pans, each padded seat pan, 1Ac and 1Ad, supports the corresponding side of the buttocks, each of which can independently pivot around a horizontal axis while the user walks as shown in FIG. 31a. A seat strap extends from the walking seat 1 and can be pulled downwardly to facilitate folding of the walking seat 1 as the seat panels pivot with respect to the seat hinge for purposes of storing the mobility assistance device 10 when not in use. In some embodiments of the mobility assistance device 10, a frame spring extends between each support frame member and the wheels of the mobility assistance device side frame 3 to provide cushioning for the user. In yet other embodiments, the walking seat can be cushioned with a spring or other suitable compressible materials for shock absorption.

The user is positioned and held by the opposing forces of the walking seat 1 and belt 2 so that the user's weight (as much as 100%) is transferred from the user's legs to device 10. When operating the device 10, the user walks by using as much or as little force as desired (or comfortable) through one or both of their legs. In one embodiment, caster wheel assembly 7 and rear wheel assembly 8 allow both turning and forward movement with a minimum of force required through the users legs so that user's with even severe limitations can safely and conveniently propel themselves about.

Figure 76:
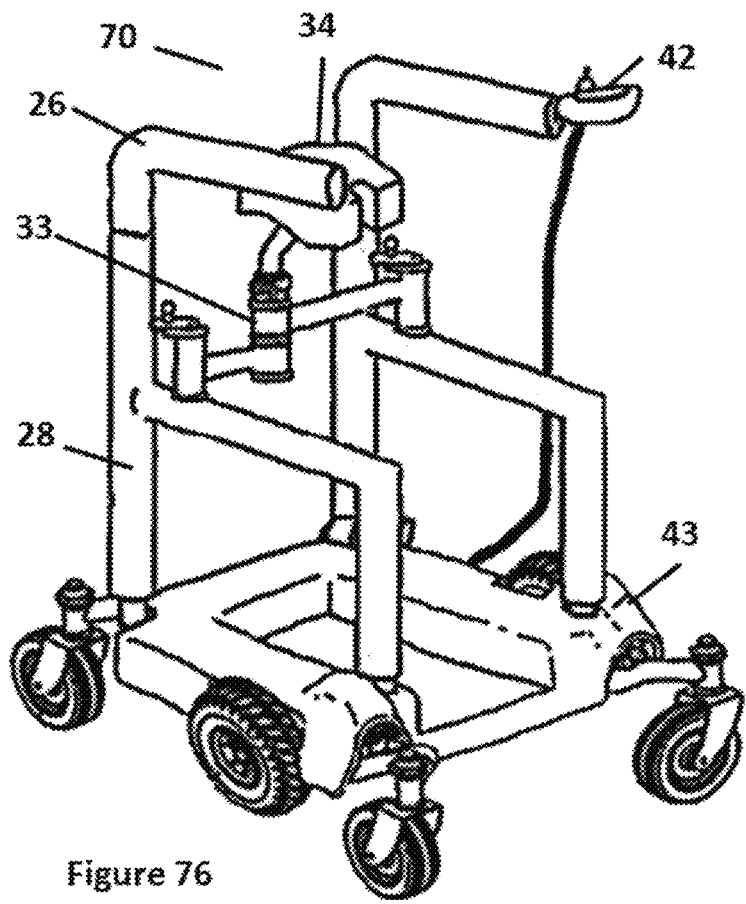
FIG. 76 shows an exemplary perspective view of heavy-weight motorized device 70.

A pair of rear wheel assemblies 8 (one of which is illustrated in FIG. 1) is rotatably mounted on the rear of the mobility assistance device frame 3. Each rear wheel assembly 8 typically includes a rear wheel axle which is rotatably mounted on wheel mount shaft 8e. A rear wheel hub may be provided on the rear wheel axle. A rear wheel rim, on which is mounted a small rubber roller or tire 8d, is generally concentric with the rear wheel hub. Multiple spokes connect the wheel rim to the rear wheel hub. In some embodiments, each of the spokes may be a spring to provide shock-absorbing capability between the rear wheel rim and the rear wheel hub. In certain embodiments, an electric drive motor is provided on the mobility assistance device frame 3 and drivingly engages one wheel axle (front, rear, or center, as shown in FIGS. 75 and 76). In one embodiment, the motor can be integrated into the wheel to form a hub wheel motor, as discussed in more details below.

The mobility assistance device 10 includes a walking seat 1 and belt 2. Walking seat 1 connects through hinge arm mechanism 5 to the side frames 3. Belt 2 connects through handles 4 and hinge posts 6 to the side frames 3. The hinge arm mechanism 5 provides rigid support horizontally to hold vertically and rigidly in place the side frames 3. The side frames 3 connect to wheel assemblies 7 and 8, firmly holding wheels assemblies 7 and 8 in a vertical position. In one embodiment, one distinction between the wheels assemblies 7 and 8 is that wheel 7 swivels 360 degrees around the vertical axis of the assembly while wheel 8 does not swivel. Wheels assemblies 7 and 8 are offset (7c and 8c respectively) from vertical shafts (7a and 8a respectively) that connect to the side frames 3. This offset allows a maximum of stability to prevent tipping while minimizing the overall size of the device 10. Wheels assemblies 8 also have braking features 12a and 12b, shown in FIG. 27.

The hinge arm mechanism 5 has three hinges, one at its center 5h2 and one hinge cylinder 5h1, 5h3 respectively at the connection points to the side frames 3. Hinges 5h1, 5h2 and 5h3 each smoothly pivot as shown in details below. These hinges 5h1, 5h2, and 5h3 enable the device 10 to be folded into a substantially smaller size for transport and storage. Hinge arm mechanism 5 is attached approximately ½-⅔ from the bottom of frame members 3. While providing rigid structural support holding in place frame members 3, structural member 5 does not interfere with the movement of the user. The hinges 5h1, 5h2 and 5h3 of hinge arm mechanism 5 lock rigidly into place using cam lever locks shown in FIG. 25.

In one embodiment, the adjustability for the device height is provided at the interface of side frames 3 and the wheel assemblies 7 and 8. Height adjustment features 6b used to raise or lower handles 4 at the interface with hinge posts 6 are of identical design to those used for the device height adjustment on side frames 3.

In one embodiment, a control box 17, fitted with a control lever or joystick, is provided on the mobility assistance device frame and connected to the drive motor to facilitate directional control of the drive motor. The control lever 17a may offer positions between rearward, neutral and forward positions to facilitate rearward, neutral and forward driving positions of the mobility assistance device 10. The control box 17 may be provided in any position which is accessible to a person (not illustrated) resting on the mobility assistance device 10M, 60 or 70, such as on the walking seat 1, for example. For motorized embodiments, a battery is secured to the mobility assistance device frame and connected to the control box through battery wiring.

Figure 27:
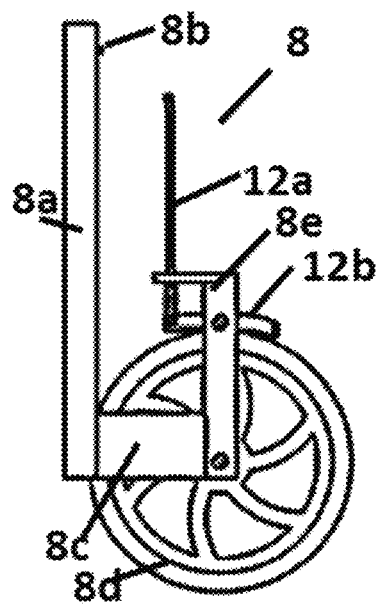
FIG. 27 shows an exemplary side view of rear wheel assembly including brake features.

In one embodiment shown in FIG. 1, each handle 4 provides a manual brake handgrip 12c, shown in FIG. 32, that in turn communicates through cable 12a actuation with a brake lever 12b mounted on wheel mount shaft 8e of wheel 8 shown in detail in FIG. 27. Actuation of the cable 12a causes the brake lever 12b to pivot about a mounting point on wheel mount shaft 8e and contact the tire 8d and apply a braking force to the wheel 8.

An alternative braking system is a caliper system mounted to wheel assembly 8 of device 10. The caliper system has two pivoting main arms, each supporting a brake pad positioned on opposing sides of the wheel rim. Actuation of the cable 12a causes the arms to pivot about a mounting point(s) such that the brake pads move together toward each other to apply a braking force to the wheel 8.

In other embodiments of the mobility assistance device 10, a brake lever engages the wheel axle of at least one wheel 7-8 to facilitate manual braking of the wheel 7-8, according to the knowledge of those skilled in the art. Moreover, as discussed below, the brake can be used as a regenerative brake to charge the battery to result in a smaller battery size with faster recharge period.

A pocket may be provided on a bottom surface of the walking seat 1. For example, the pocket may be provided on each seat panel of the walking seat 1. A notch 1c may be provided on the front edge of the walking seat to provide pressure relief to the user's tail bone. In some embodiments, a footrest 14 with strap 14a can be provided near the bottom of the frame 3.

The device 10 counteracts the negative effect of prolonged sitting in a wheelchair. Remaining in a seated position for extended period of time is detrimental to an individual's health, negatively affecting many basic body functions including digestive, cardio-vascular, and respiratory systems. Encouraging and enabling an individual to periodically change position to a standing or partially standing posture and especially if the individual can walk around can improve these body functions and help avoid further deterioration of health.

The device 10 can function as a conventional walker. The individual can stand behind the device and walk, getting support by holding onto the handles 4, similar to the conventional walker. The user can use the device with the handles 4 "as is" or, if s/he prefers, s/he can also reverse the direction of the handles.

The device can be converted into a wheelchair. By installing foot rests 14, reversing the handles 4 and installing a sling seat 13, the device 10 enables a second person to push the user from the rear of the device.

The mobility assistance device 10 encourages the user to ambulate using his or her legs as much as possible. In contrast, regular wheelchair users spend long hours seated or lying down which can lead to reduced blood circulation, deficiencies in digestion, mental uneasiness and significant general discomfort. The device 10 keeps the body up and moving as much as possible, helps enable a healthy and empowered lifestyle and enables walking as a regular part of a daily fitness program.

The device 10 can be used in conjunction with a rehabilitation therapy process. The user, under the direction of a physical therapist or other health professional, transitions in position from a mostly seated posture to a fully or nearly fully standing posture over the course of therapy. The user would start with the device in a relatively low setting so that the legs project more forward from the device similar to when sitting in a chair. As the therapy proceeds and the user improves and gains proficiency, the device height is raised in small increments. This process continues until the user assumes as vertical standing posture as deemed appropriate by the directing health professional. If the user is done with the therapy and no longer requires the device (such as for a surgically repaired knee, for example) the user can resume walking without the device. If the user will continue to require the device to enable walking for the indefinite future (such as for a permanent leg disability, for example), the device will remain more or less at this setting going forward.

Figure 2:
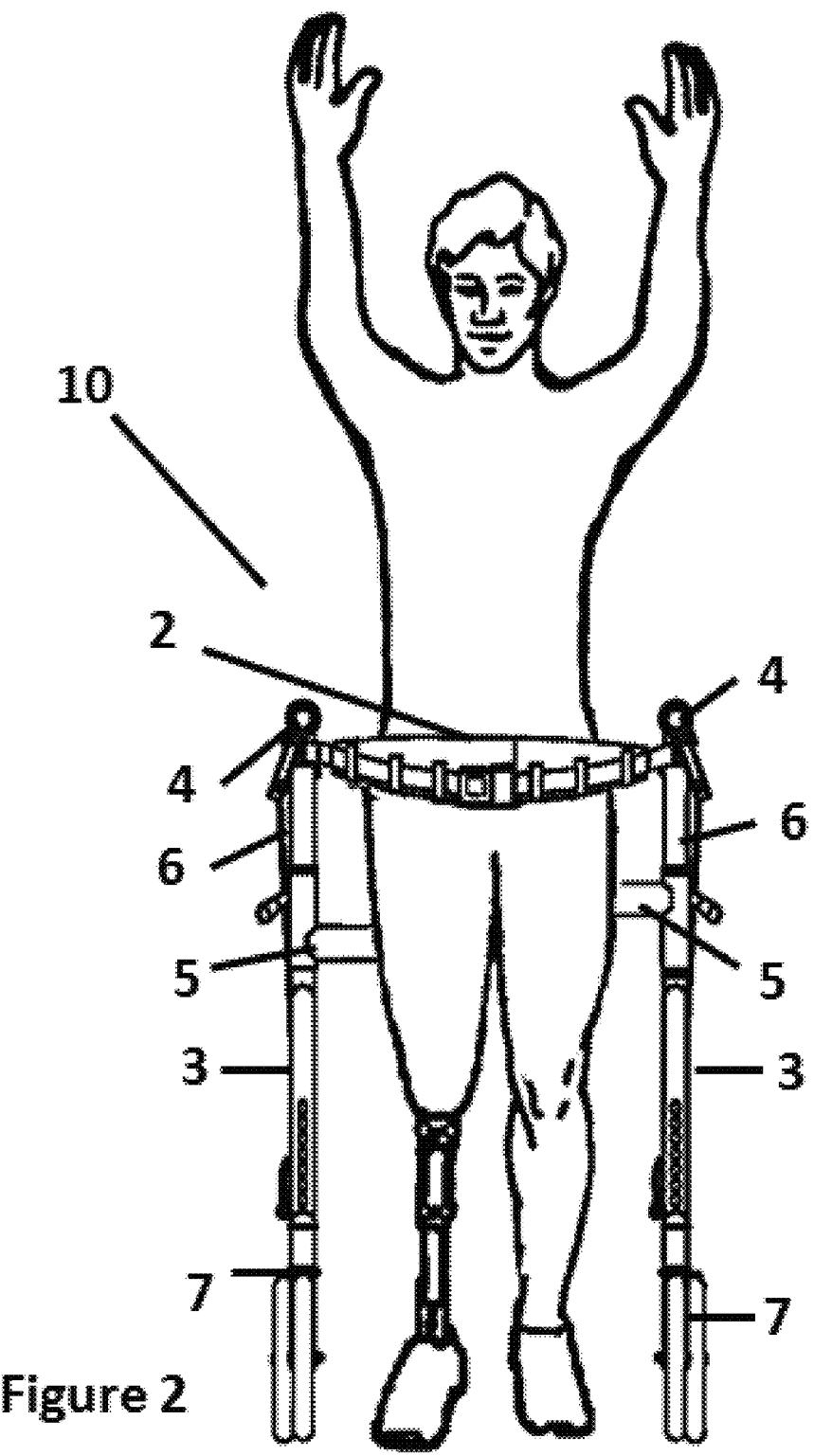
FIG. 2 shows an exemplary front view of device 10 with person.

As illustrated below in FIGS. 3-6, using the device 10 will help the user progress through a rehabilitation program to restore the user's ability to walk. Additional benefits include increased strength, flexibility, improved mobility, strengthened heart and lungs, while helping control weight. FIG. 2 shows a front view of the device 10 with a disabled person secured into position by belt 2. The person's hands are lifted in this view to show that hands are not necessary in order to effectively move about using the device 10. This view shows in another manner the arrangement of the handles 4, hinge posts 6, hinge arm mechanism 5, side frames 3, and caster wheel assemblies 7. The user is shown in the fully standing posture and demonstrating movement without using the arms for support.

The portable mobility assistance device allows individuals to move about in a full standing (legs vertical) or partially standing (legs anywhere between seated and standing position) posture in a manner that can significantly reduce the stresses and discomfort on ankle, knee, hip, wrist, elbow and shoulder joints or at the interface with a prosthetic leg. In other embodiments, "partially standing" would encompass the crouch/squat position of the user.

The device 10 potentially reduces or eliminates the dependency on a wheelchair for mobility, allowing the user to walk about for potentially extended periods. The device 10 allows the arms of the individual to be more available to use for other purposes. The device 10 also provides stable support while traversing wheelchair accessible walkways, ramps, paths, rooms and other indoor and outdoor facilities as well as (when appropriately outfitted) over a variety of other terrain. The device 10 adapts to provide a comfortable seated position for times the individual prefers to sit. The preferred embodiment is foldable into a compact form and capable of being conveniently transported such as in an automobile trunk or as a checked item for an airplane.

FIG. 2 is a front view of a person using the mobility assistance device 10 and supported by the walking seat and the belt. The user faces away from the hinge arm mechanism 5 and is approximately centered between the two side frames 3. Handles 4 are situated at similar heights on the right and left side of the person's body at approximately the individual's waist height. Hinges $5h1$, $5h2$ and $5h3$ lock rigidly into position and securely hold side frames 3 parallel to each other and perpendicular to hinge arm mechanism 5. Hinges $5h1$, $5h2$ and $5h3$ are used to fold the device into a convenient size for storage and transport. Up to 100% of the person's body weight is supported through the walking seat 1 with belt 2 to hinge arm mechanism 5 and hinge posts 6 respectively, to side frames 3 and onto the ground or floor through the wheel assemblies 7 and 8.

Figure 2A:
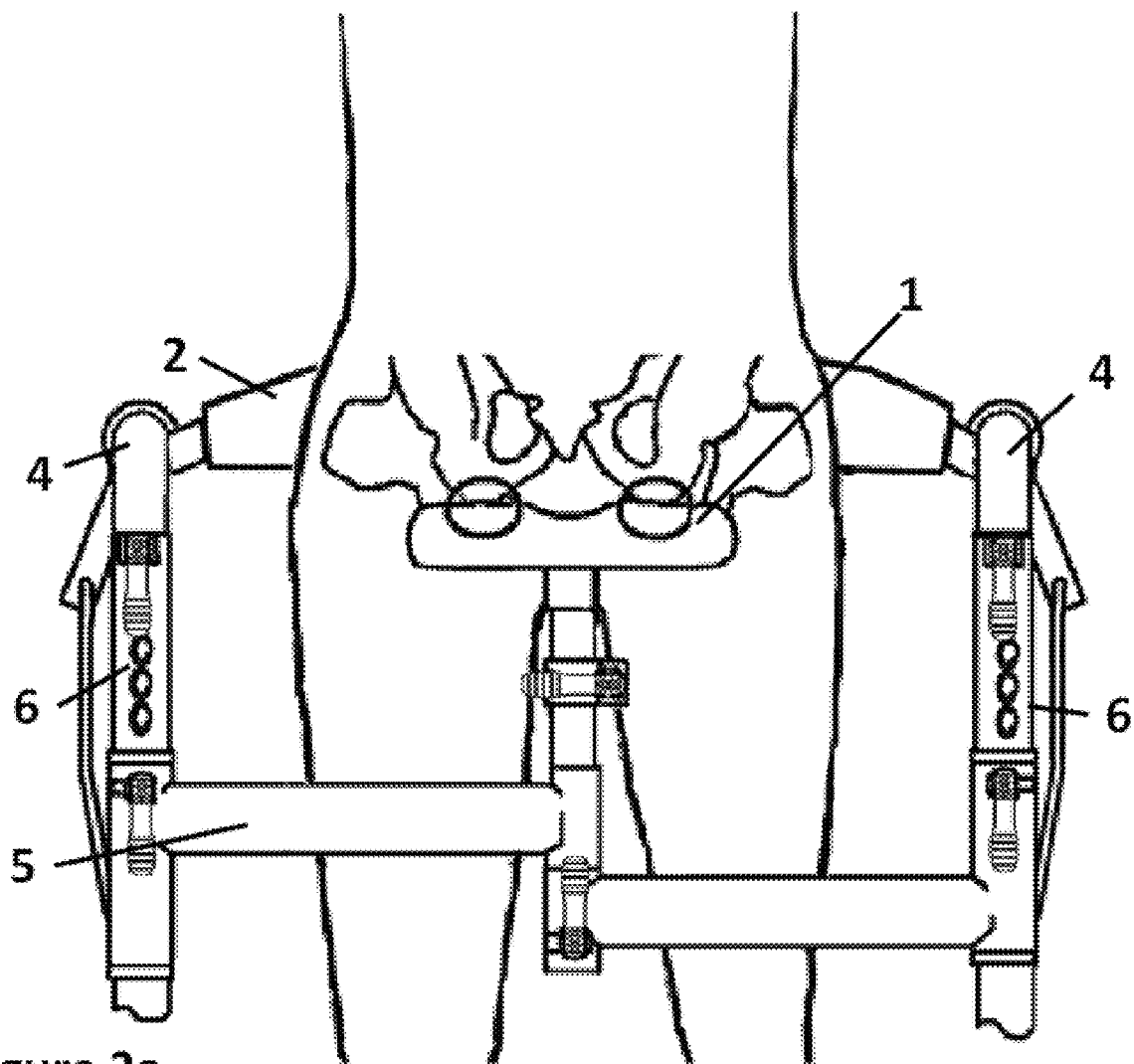
FIG. 2a shows in more details an exemplary sit-bones positioning on the walking seat.

FIG. 2A shows a detail rear view of the user positioned on the walking seat of device 10. This view shows an overlay of the user's pelvis and hips to highlight the position of the ischial tuberosities (sit-bones) onto the walking seat and the relative position of the belt 2 during operation of device 10.

The walking seat does not have a "nose" or "horn" typical of a bicycle seat. This eliminates the transfer of body weight through the pubic area which would otherwise occur. Additionally, the walking seat 1 positions the sit-bones towards the front of the walking seat so that the legs are free to move forward and backward when walking. In a standing position, there is much less surface of the sit-bones available, and that surface is more vertically oriented as compared to when seated. So to use the sit-bones to support the body weight while standing and walking as with device 10, a secondary support (i.e. the belt 2) is necessary in addition to the walking seat 1.

Figure 3:
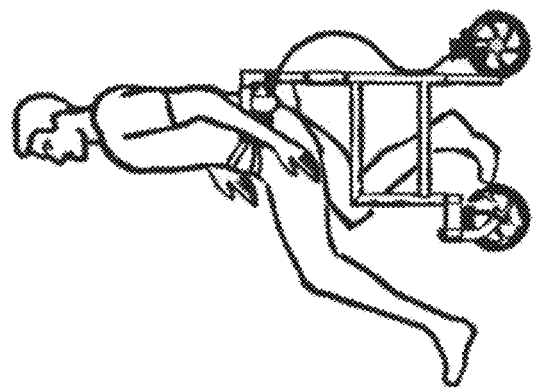
FIG. 3 shows an exemplary side view of person in low (closer to seated) posture.

FIG. 3 shows the posture of a user who is just beginning use and getting acclimated with the device 10. As a part of a rehabilitation process, a medical practitioner allows time for the user to gain strength and get accustomed to using the affected leg by starting the user at a relatively low posture. In the view, the user is positioned approximately half-way between a normal seated posture and a full standing posture with legs projected out relatively more horizontally than later in the rehabilitation cycle.

Figure 4:
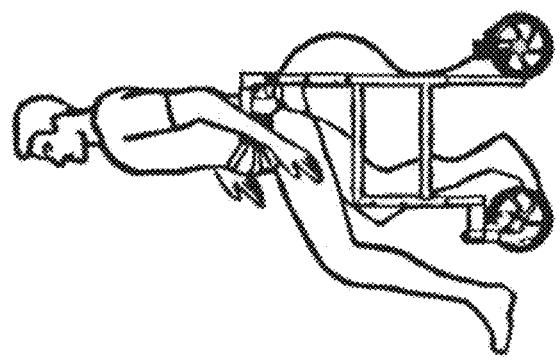
FIG. 4 shows an exemplary side view of person in low partially standing posture.

FIG. 4 shows a secondary position in device 10 by the user as a rehabilitation process progresses. In this view, the user is positioned at approximately ⅔ of a fully standing posture. This signifies that user has become more proficient at operating device 10 while gaining strength and capability in the affected limb.

Figure 5:
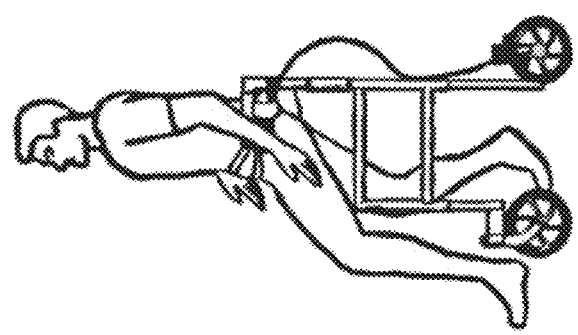
FIG. 5 shows an exemplary side view of person in high partially standing posture.

FIG. 5 shows the user at an advanced posture in the device 10 of approximately 80% of a fully standing posture. At this stage, the user is generally quite comfortable moving about in the device 10 and has progressed towards later stages of the rehabilitation cycle.

Figure 6:
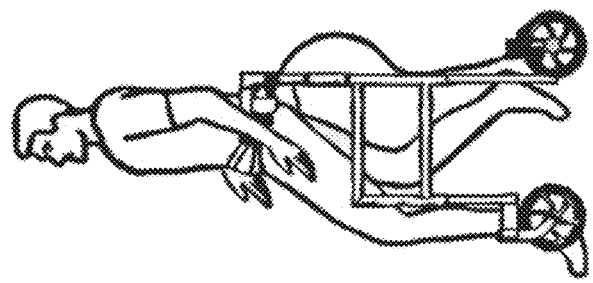
FIG. 6 shows an exemplary side view of person in full standing posture.

FIG. 6 shows the user at the most advance posture in the device 10 of 95% or more of a fully standing posture. The user has gone through all or nearly all of the rehabilitation cycle. Should the user require device 10 for the long term, this is the desired posture for ongoing use to maximize long-term health and lifestyle benefits.

Figure 7:
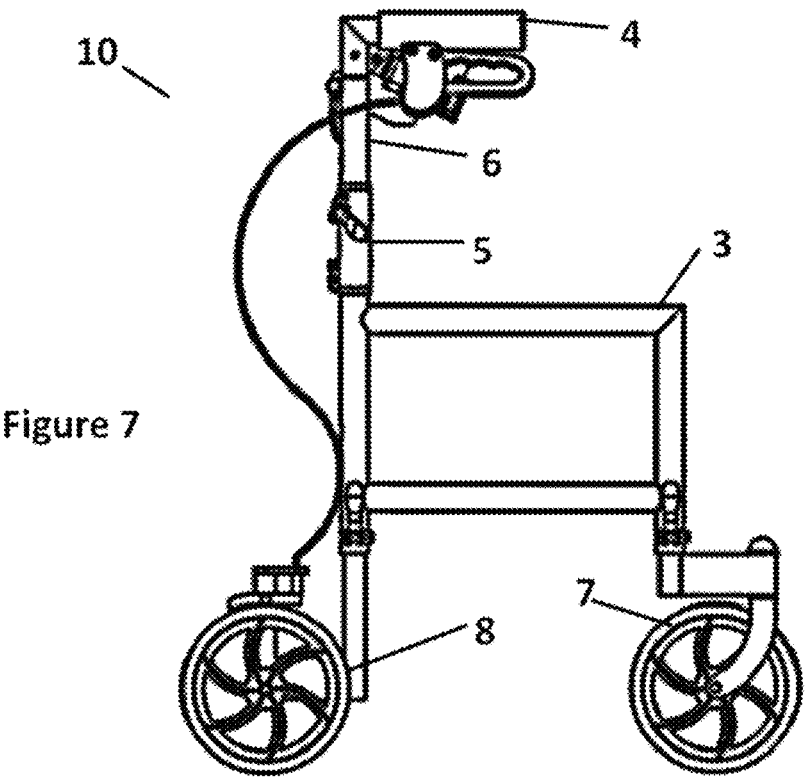
FIG. 7 shows an exemplary side view of device 10.

FIG. 7 shows a side view of the device 10. This view shows from another direction the handles 4, hinge posts 6, hinge arm mechanism 5, side frames 3, rear wheel assembly 8, and caster wheel assembly 7.

Figure 8:
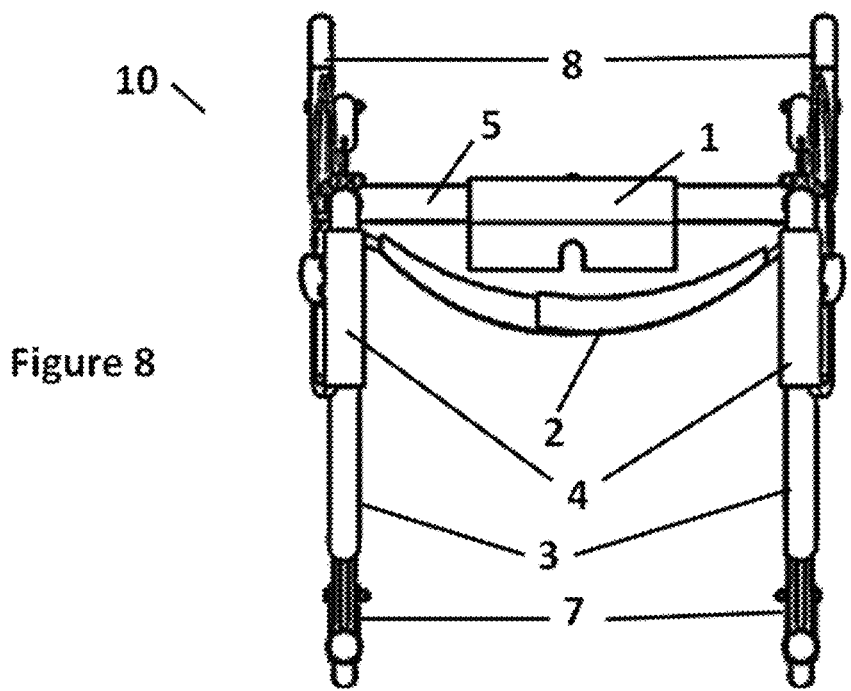
FIG. 8 shows an exemplary top view of device 10.

FIG. 8 rounds out the initial overview of the device 10 by showing the top view. Again, shown is the walking seat 1, belt 2, side frames 3, handles 4, hinge arm mechanism 5, caster wheel assemblies 7 and rear wheel assemblies 8.

Figure 9:
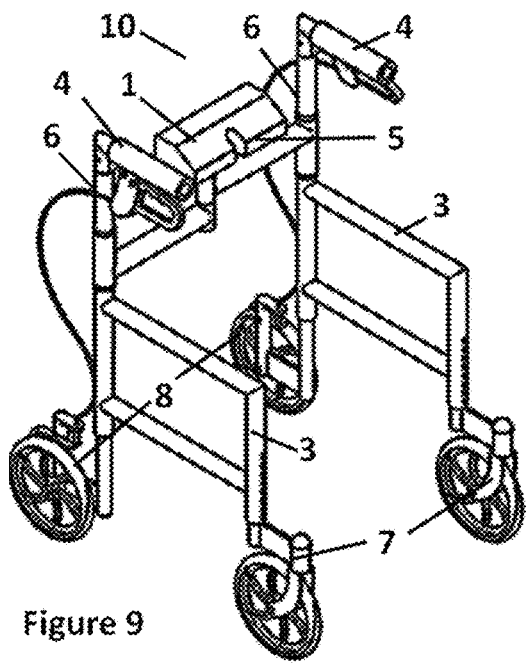
FIG. 9 shows an exemplary perspective view of device 10 fully opened.

FIG. 9 shows the fully open front perspective view of device 10. In this orientation, hinge arm mechanism 5 is perpendicular to the side frames 3. Rear wheel assemblies 8 extend towards the rear of device 10 in alignment with side frames 3. Caster wheel assemblies 7 similarly extend forward in alignment with side frame 3 (in opposite direction as rear wheel assemblies 8). This fully open configuration of the device 10 is shown without belt 10 to allow a clearer view of the remaining device 10 major structural components. This is the orientation of device 10 when operated by the user.

Figure 10:
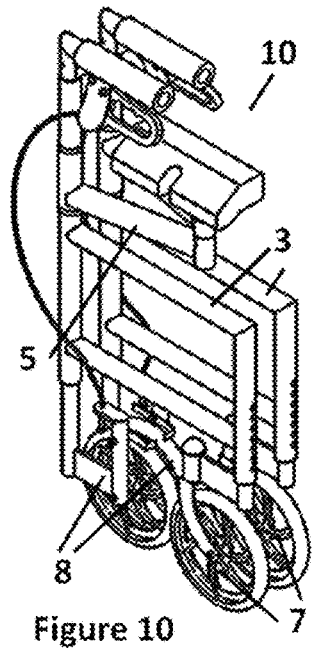
FIG. 10 shows an exemplary perspective view of device 10 fully closed.

FIG. 10 by contrast shows device 10 fully closed from perspective view. In this closed position, the device is ready to be transported, such as in the trunk of a car or checked in as baggage of an aircraft. Rear wheel assemblies 8 and caster wheel assemblies 7 are swiveled 180 degrees inward towards the center of side frames 3 in complete opposite orientation as shown in FIG. 9. This reduces the total depth of the device by about 35%. Hinge arm mechanism 5 is folded inward so that its alignment is nearer parallel to side frames 3. This folded position of hinge arm 5 reduces the width of the device by approximately 67%. This configuration minimizes the size and bulk of the device 10, making it of a form that is highly transportable and easily stowed in a minimum of space.

Figure 11:
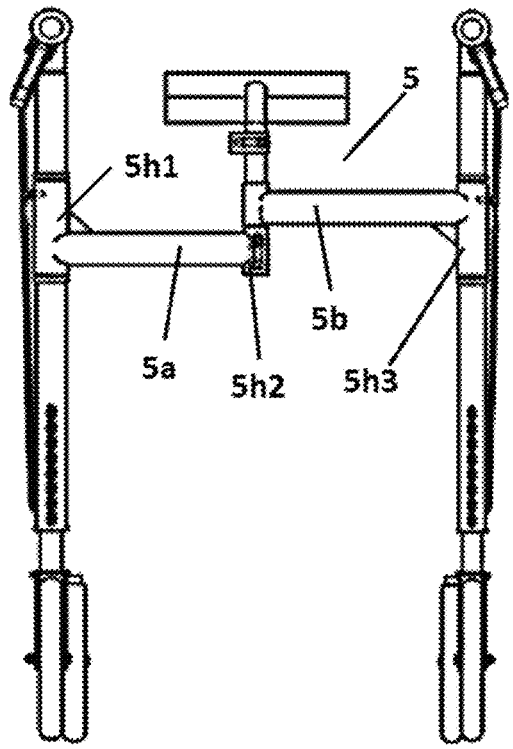
FIG. 11 shows an exemplary front view of device 10 fully opened.

FIG. 11 shows the front view of device 10 in the fully open configuration. Hinge arm mechanism 5 is made of left horizontal arm 5a, right horizontal arm 5b, hinge cylinders 5h1 and 5h3, and center hinge 5h2. When fully open, device 10 has each component oriented along a single plane.

Figure 12:
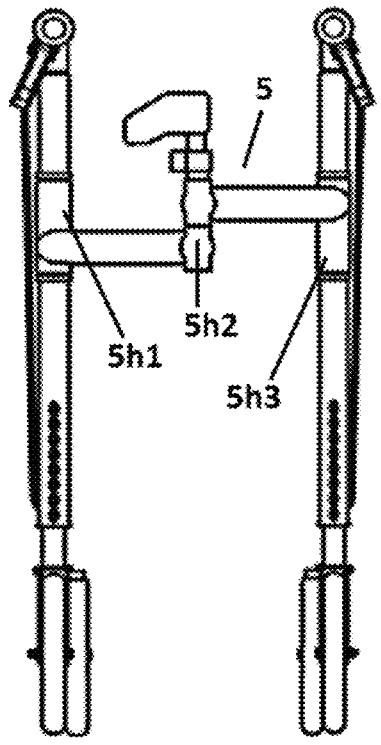
FIG. 12 shows an exemplary front view of device 10 half way closed.

FIG. 12 shows the front view of device 10 in half open configuration. In this view, hinge arm 5 swivels around hinge cylinders 5h1 and 5h2, and center hinge 5h3. Left horizontal arm 5a and right hinge arm 5b are now oriented at about 90 degrees to each other.

Figure 13:
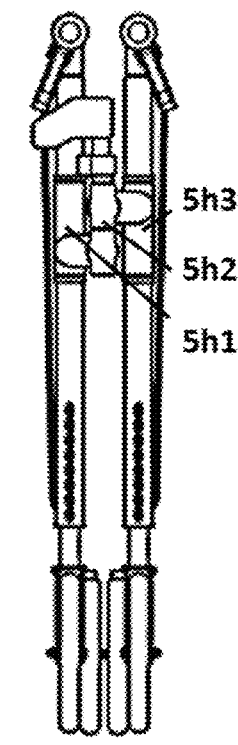
FIG. 13 shows an exemplary front view of device 10 fully closed.

FIG. 13 shows the front view of device 10 in the fully closed configuration. Left hinge arm 5a and right hinge arm 5b are now oriented much closer to parallel to each other at approximately 15 degrees to each other.

Figure 14:
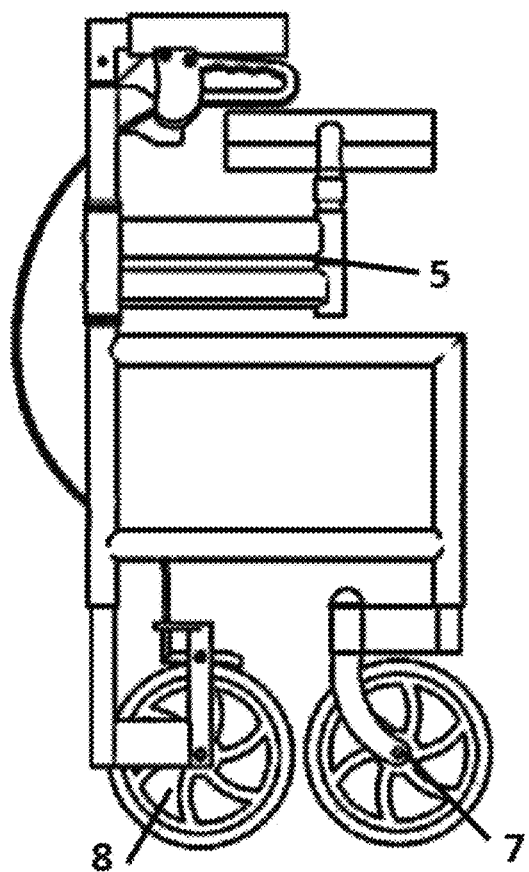
FIG. 14 shows an exemplary side view of device 10 fully closed.

FIG. 14 shows the side view of the device 10 fully closed. In this view hinge arm mechanism 5 is folded inward on itself, rear wheel assemblies 8 and caster wheel assemblies 7 are oriented 180 degrees opposite their fully open position.

Figure 15:
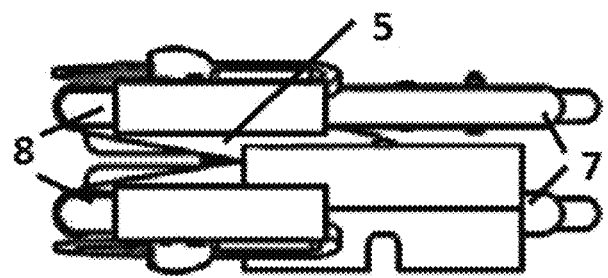
FIG. 15 shows an exemplary top view of device 10 fully closed.

FIG. 15 shows the top view of device 10 fully closed. Hinge arm mechanism 5, rear wheel assemblies 8, and caster wheel assemblies 7 are oriented to minimize the device 10 footprint to its smallest form.

Figure 16:
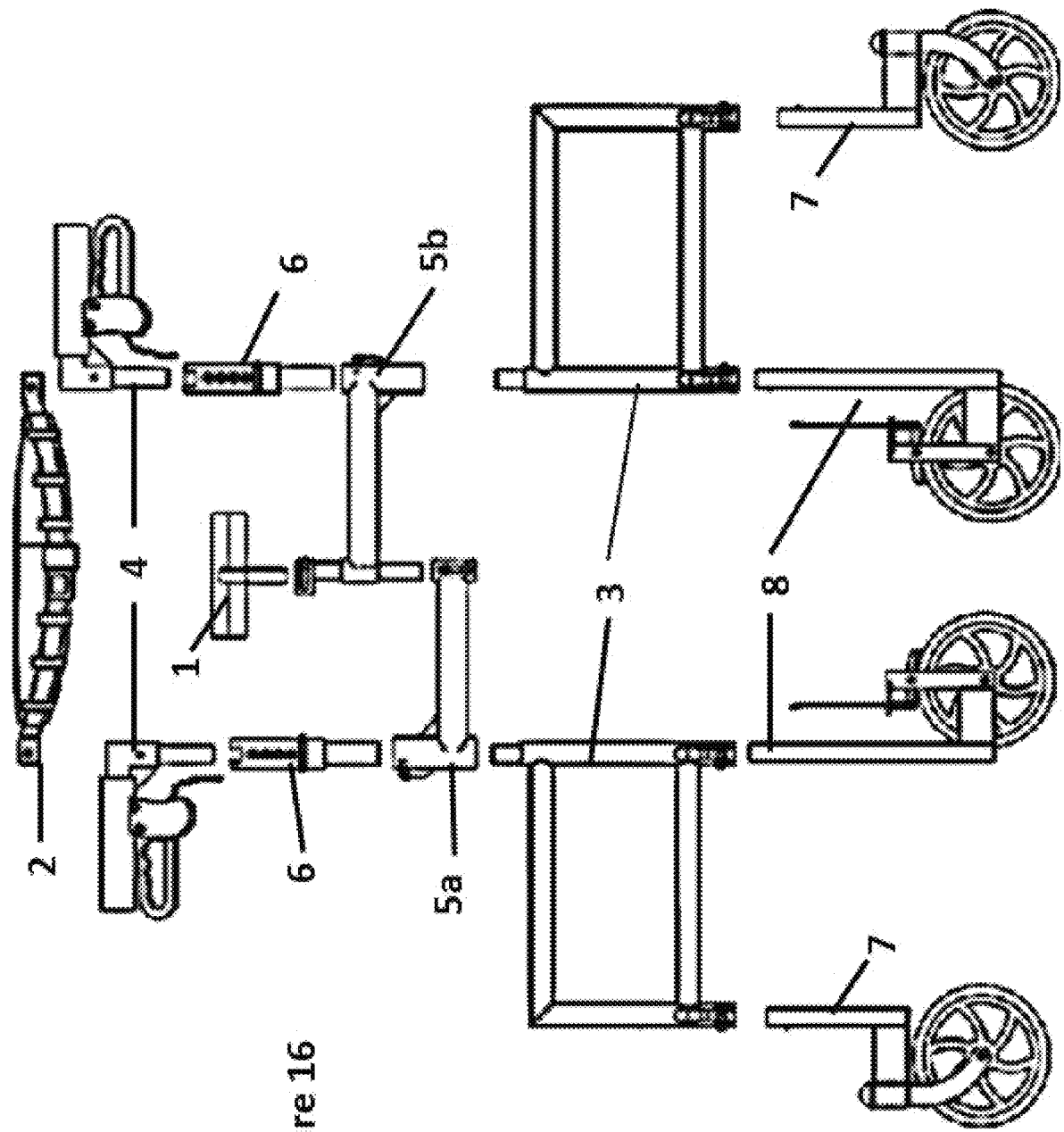
FIG. 16 shows an exemplary exploded view of device 10.

FIG. 16 is an exploded view of device 10 showing each major component in its most helpful view. This highlights and clarifies the basic forms of each. Walking seat 1 is shown in front view. Belt 2 is shown in front view. Side frames 3 are shown in side views. Handles 4 are shown in side views. Left hinge arm 5a and right hinge arm 5b are shown in front views. Hinge posts 6 are shown in front views. Caster wheel assemblies 7 are shown in side views. Rear wheel assemblies 8 are shown in side views.

Figure 17:
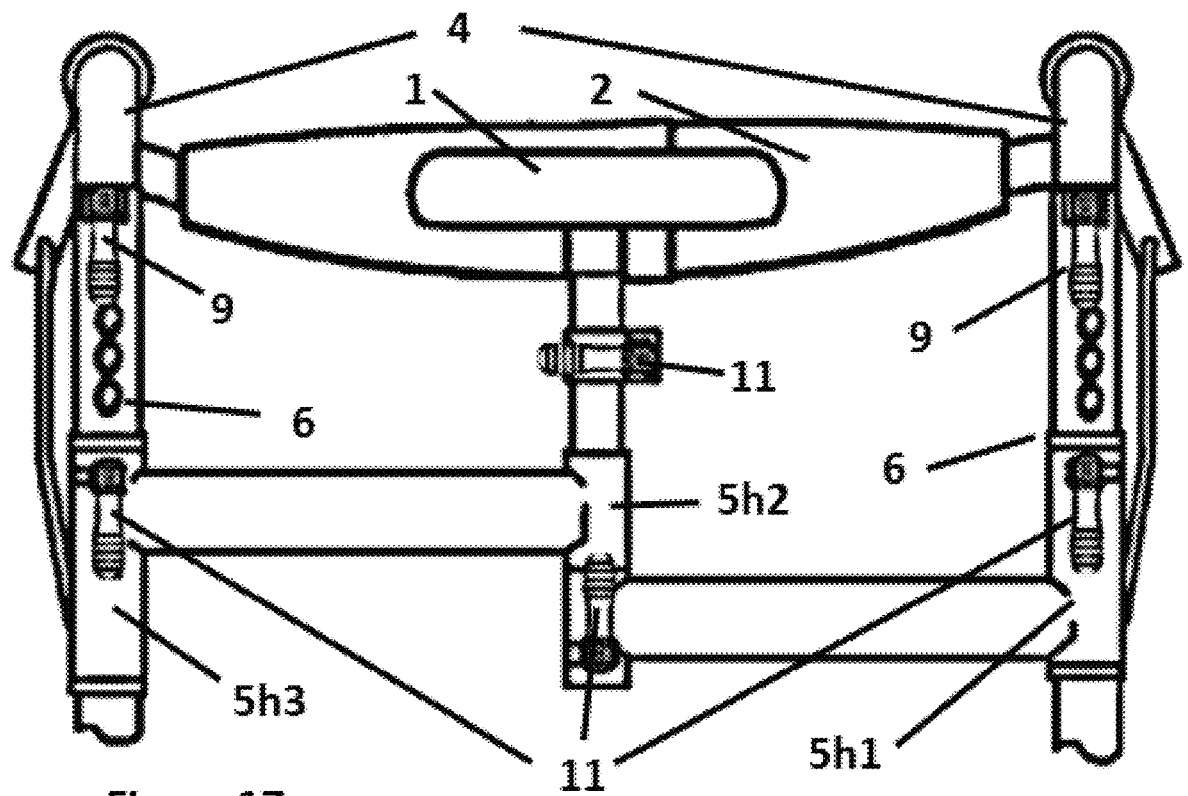
FIG. 17 shows an exemplary detail back view of device 10.

FIG. 17 is a detail rear view of the upper portion of device 10. This view shows the locking features for the walking seat 1, hinge cylinders 5h1 and 5h3, center hinge 5h2, and hinge posts 6. Belt 2 is fastened securely to handles 4 by bolts, nuts and washers. Cam levers 9 are bolted to hinge posts 6 to provide secondary locking of the handles 4 to the hinge posts 6. Rotating upward releases the cam lever 9, allowing changing handle 4 height up or down by pushing spring button 4b (see FIG. 20) through height adjustment feature 6b. Cam locking levers 11 tighten or release the hinge cylinders 5h1 and 5h3 and center hinge 5h2 for opening or closing device 10. The individual can optionally stand and walk behind the device, getting support by holding onto the handles, similar to the conventional walker either with the handles "as is" or, if they prefer, with the direction of the handles reversed.

Figure 18:
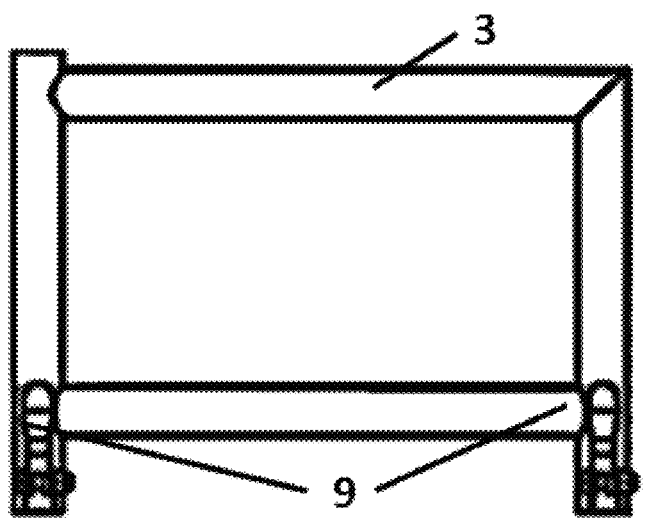
FIG. 18 shows an exemplary side view of side frame.

FIG. 18 shows the side frame 3. Side frame 3 uses the same secondary locking cam levers 9 as does hinge posts 6. Again, by lifting cam lever 9 the primary height adjustment (shown in later figures) can be activated.

Figure 19:
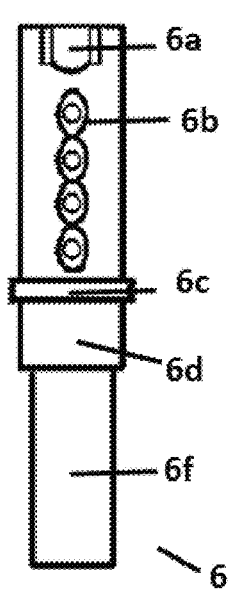
FIG. 19 shows an exemplary rear view of hinge post.

FIG. 19 shows the hinge post 6. This view has the cam lever 9 and bolt feature removed to show the hinge post 6 basic form. Feature 6a is the cam lever bolt attachment and slot through with the cam lever 9 tightens or releases the handle 4. Once cam lever 9 is released, feature 6b enables handle 4 to raised or lowed by depressing a spring button 4b (see FIG. 20).

Figure 20:
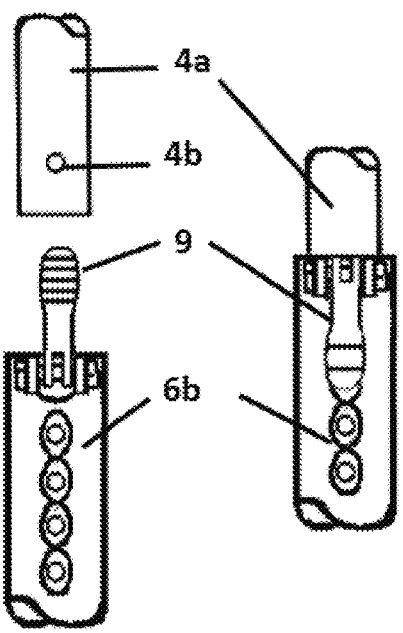
FIG. 20 shows an exemplary detail view of handle height adjustment and locking features.

FIG. 20 shows a detail of the bottom portion 4a of handle 4 that includes the spring button 4b in both the open (released) and closed (locked) positions. Rotating upward cam lever 9 allows spring button 4b to be depressed through height adjustment feature 6b so that handle 4 can be raised or lowered in position relative to hinge post 6. Rotating downward cam lever 9 provides secondary locking once spring button 4b snaps into one of the holes of height adjustment feature 6b.

Figure 21:
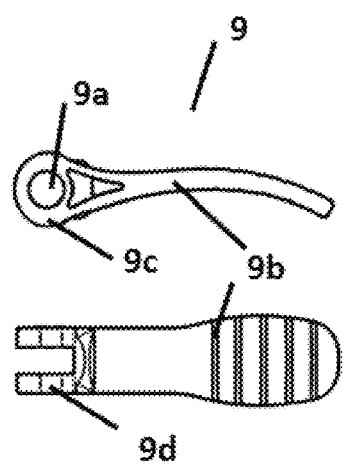
FIG. 21 shows an exemplary cam lever side and top views.

FIG. 21 shows side view and top view of cam lever 9. Cam lever rotates up or down by pivoting around bolt in hole 9a by applying pressure to cam handle 9b. Cam 9c increases or decreases the interference with the handle 4 when opened and closed.

Figure 22:
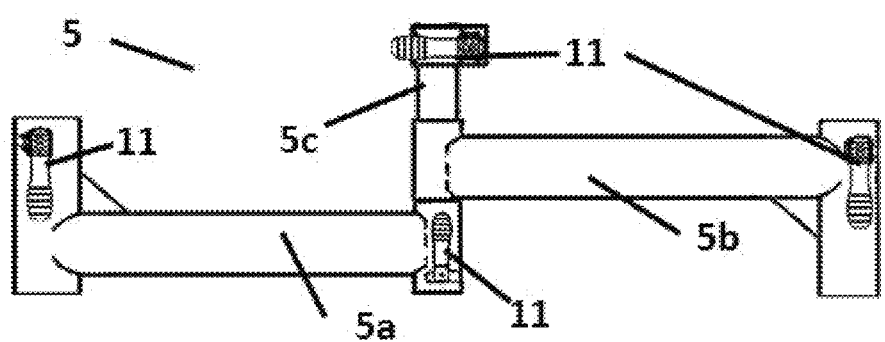
FIG. 22 shows an exemplary rear view of hinge arm mechanism.

FIG. 22 shows an assembled front view of hinge arm mechanism 5 and its locking components. When device 10 is in use, left hinge arm 5a locks to right hinge arm 5b using a cam lever lock 11. Similarly, left hinge arm 5a and right hinge arm 5b lock to hinge posts 6 using cam levers 11. Seat 1 is similarly locked into position by cam lever 11 positioned on seat holder 5c.

Figure 23:
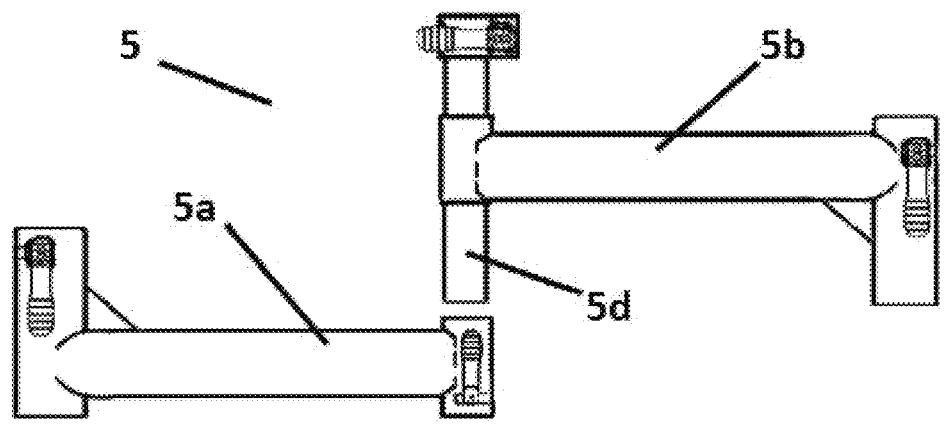
FIG. 23 shows an exemplary rear view of hinge arm mechanism, left and right arms separated.

FIG. 23 shows the hinge arm mechanism 5 front exploded view. Left hinge arm 5a is securely fastened to right hinge arm 5b by hinge cylinder 5d, which allows unrestricted axial rotation between hinge arms 5a and 5b.

Figure 24:
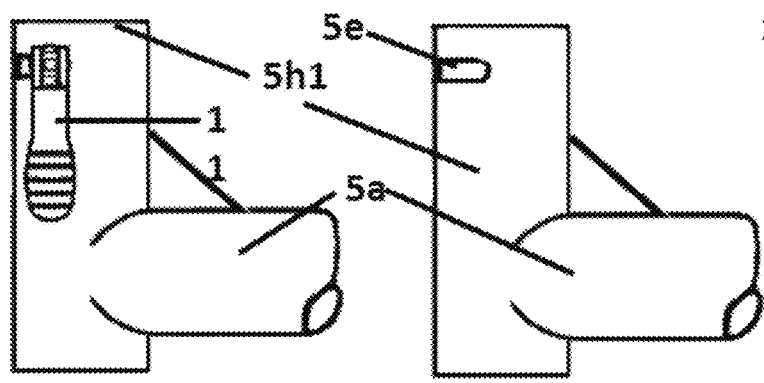
FIG. 24 shows exemplary detail views of hinge arm mechanism locking features.

FIG. 24 shows a front detail view of hinge cylinder 5h1 both with and without the cam locking lever. Slot 5e provides a window through hinge cylinder 5h1 that allows locking cam lever 11 to be fastened to hinge post 6. Lifting cam locking lever 11 releases force from hinge cylinder 5h1 on hinge post 6, allowing unrestricted axial rotation between the two elements for the length of slot 5e (approximately 80 degrees). Lowering the cam locking lever 11 produces a locking force that rigidly fixes the relative positions of hinge cylinder 5h1 and hinge post 6. Hinge cylinder 5h3 is similarly operated with the other hinge post 6 and center hinge 5h2 also operates similarly with hinge cylinder 5d (rotations allowed is 180 degrees at this interface).

Figure 25:
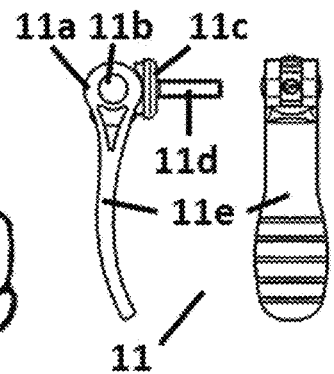
FIG. 25 shows an exemplary hinge arm mechanism locking cam levers.

FIG. 25 shows the side and top views of cam locking lever 11. Raising or lowering cam handle 11e causes cam feature 11a to rotate around cylinder 11b which, through bolt 11d, either presses or releases washer 11c to lock or release the hold between the hinge components (5h1, 5h2, 5h3 with hinge post 6 or hinge cylinder 5d).

Figure 26:
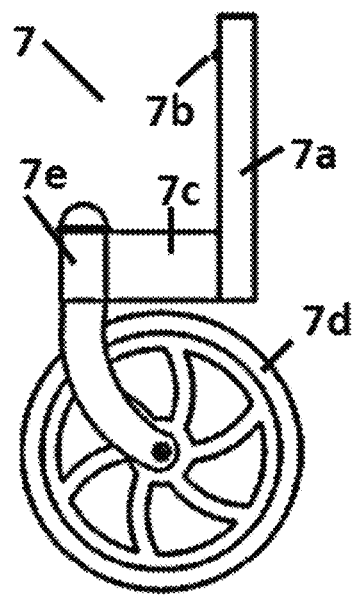
FIG. 26 shows an exemplary side view of caster wheel assembly.

FIG. 26 is a side view of the caster wheel assembly 7. This view shows in profile the height adjustment shaft 7a, which has the spring button 7b proximate to its top. The caster wheel 7d swivels 360 degrees and has smooth rolling bearings within the bearing shaft 7e. The offset 7c allows for the castor to be located forward for excellent weight distribution and stability while still allowing the device 10 to be closed into a compact form for transport. As an alternative embodiment, offset 7c can be eliminated to allow an even more compact form for the user during operation. For smaller people and tight indoor quarters, reduction or elimination of this offset may be desirable.

FIG. 27 is a side view of rear wheel assembly 8 which includes height adjustment shaft 8a that includes spring button 8b. Offset 8c allows the non-castor wheel 8d to be offset for maximum weight distribution and stability while allowing the device 10 to be closed into a compact form for transport. Rear wheel assembly 8 also contains mounting shaft 8e which holds braking features including the spring loaded brake lever 12b that connects with the braking system through brake cable 12a. As an alternative embodiment, offset 8c can be eliminated to allow an even more compact form for the user during operation. For smaller people and tight indoor quarters, reduction or elimination of this offset may be desirable.

Figure 28:
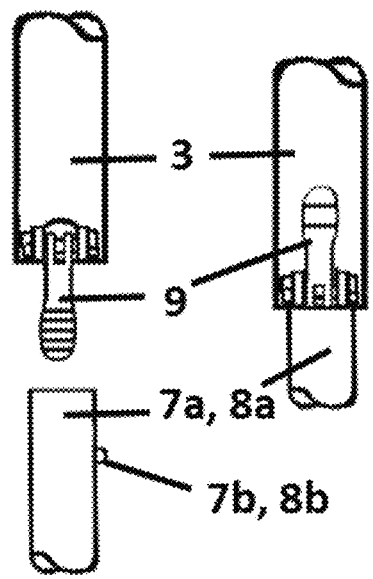
FIG. 28 shows an exemplary detail view of height adjustment features for wheel assemblies.

FIG. 28 shows the detail view of the height adjustment features of wheel assemblies 7 and 8 in both an open, detached state as well as closed and connected state. Once cam lever 9 is released, the spring button 7b or 8b can be depressed to raise or lower the height of device 10.

Figure 29:
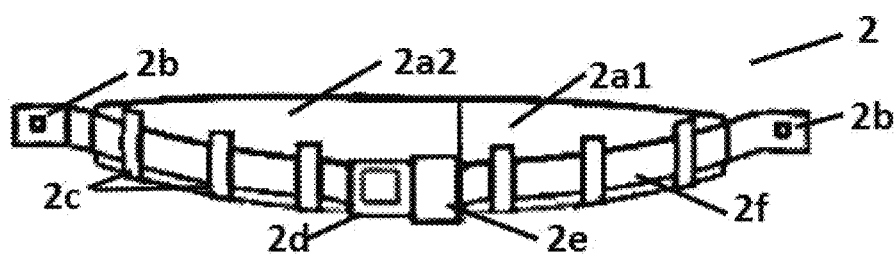
FIG. 29 shows an exemplary front view of belt.

FIG. 29 shows the belt 2 with both left belt side 2a2 and right belt side 2a1 latched by female 2d and male 2e latch elements. The belt 2 is bolted to the handle 4 using eyelet holes 2b. The belt loops 2c securely hold belt strap 2f while allowing for length adjustability to accommodate various sizes of users.

Figure 30:
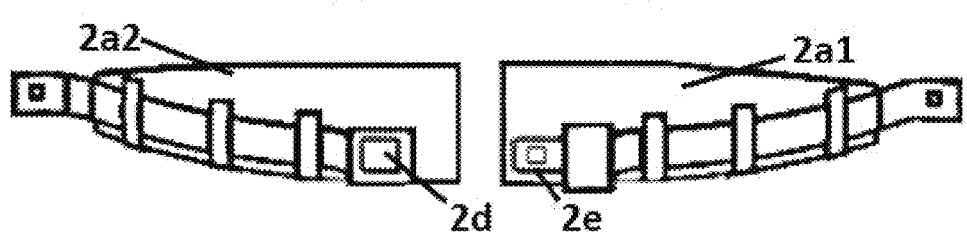
FIG. 30 shows an exemplary front view of belt, unlatched.

FIG. 30 shows belt 2 unlatched and clarifying that it consists of two sides including left belt side 2a2 and right belt side 2a1. Belt 2 latches enable quick connection and quick release of the user and are similar in design and operation as those used in automobile or aircraft seat belts.

FIG. 31 is a front perspective view of walking seat 1, including shaft 1a, cushion 1b and comfort notch 1c. Walking seat 1 works in conjunction with belt 2 to apply opposing forces to the hip/pelvis area of the user to transfer body weight from the legs to the device 10. By design, the walking seat 1 allows the legs to move relatively freely forward and backward while walking in device 10.

FIG. 31a shows perspective, top and front views of alternative walking seat 1A. Walking seat 1A has two padded seat pans 1Ac and 1Ad that support the corresponding side of the buttocks, each of which can independently pivot around a horizontal axis while the user walks. By allowing the set pans to pivot independently, the walking seat is shaped to conform more closely to the contours of the user's buttocks while still allowing the legs to comfortably move forward and backward in a natural walking motion. Some users may prefer this alternative walking seat form.

FIG. 32 is a side view of the handle 4 that includes brake handle 12c and attaches to brake cable 12a. A foam grip 4a provides comfort over the handle body 4b when the user holds the handle 4. Belt 2 is bolted to handle 4 at throughhole 4c. Height adjustment shaft 4d includes spring button 4b that enables discreet height levels in conjunction with hinge post 6 height adjustment feature 6b.

Figure 33:
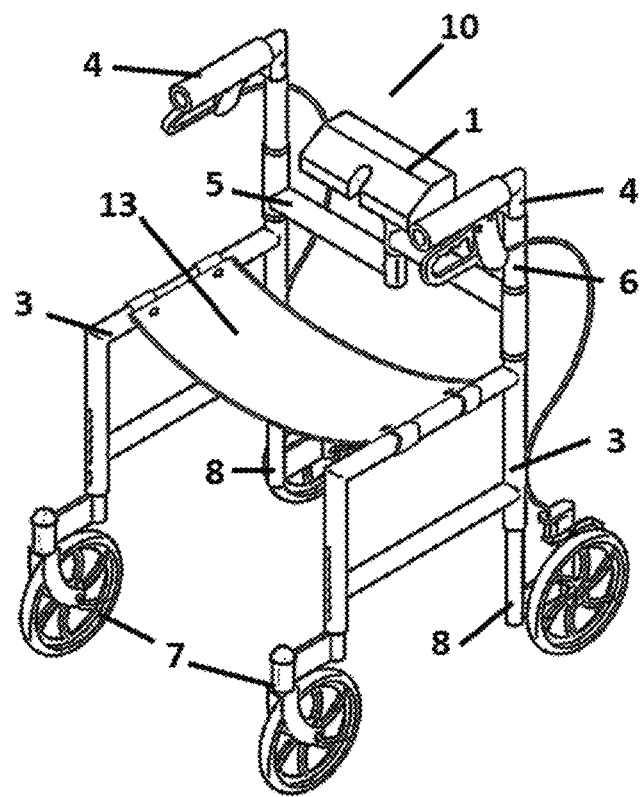
FIG. 33 shows an exemplary front perspective view of device 10 with sling seat installed.

FIG. 33 shows device 10 with the optional sling seat 13 installed. Sling seat 13 provides a comfortable resting position for the user when they are not walking with the device. The sling seat 13 attaches to side frames 3 to allow a secure seated position.

Figure 34:
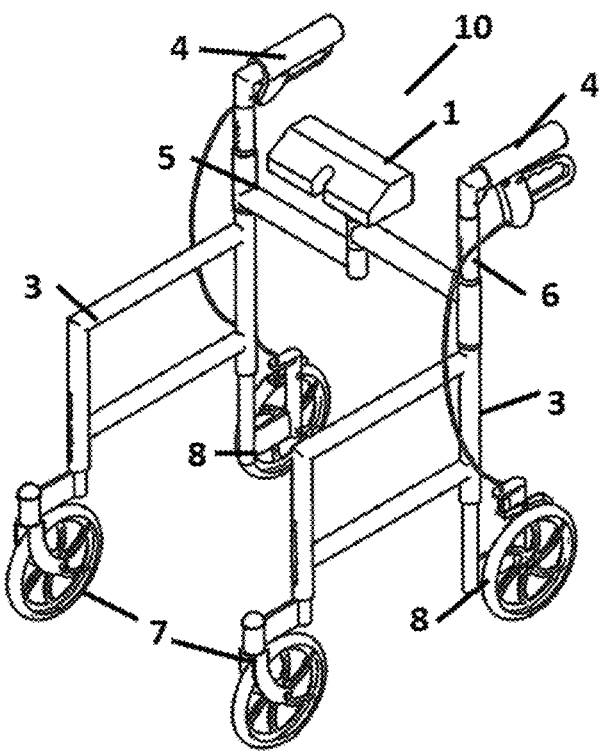
FIG. 34 shows an exemplary front perspective view of device 10 in optional usage configuration.

FIG. 34 shows the optional device 10 configuration with the handles 4 mounting in the reverse direction. Device 10 can be used as a "typical" stand-behind walker with the user having the option of using in this manner with or without reversing handles 4.

Figure 35:
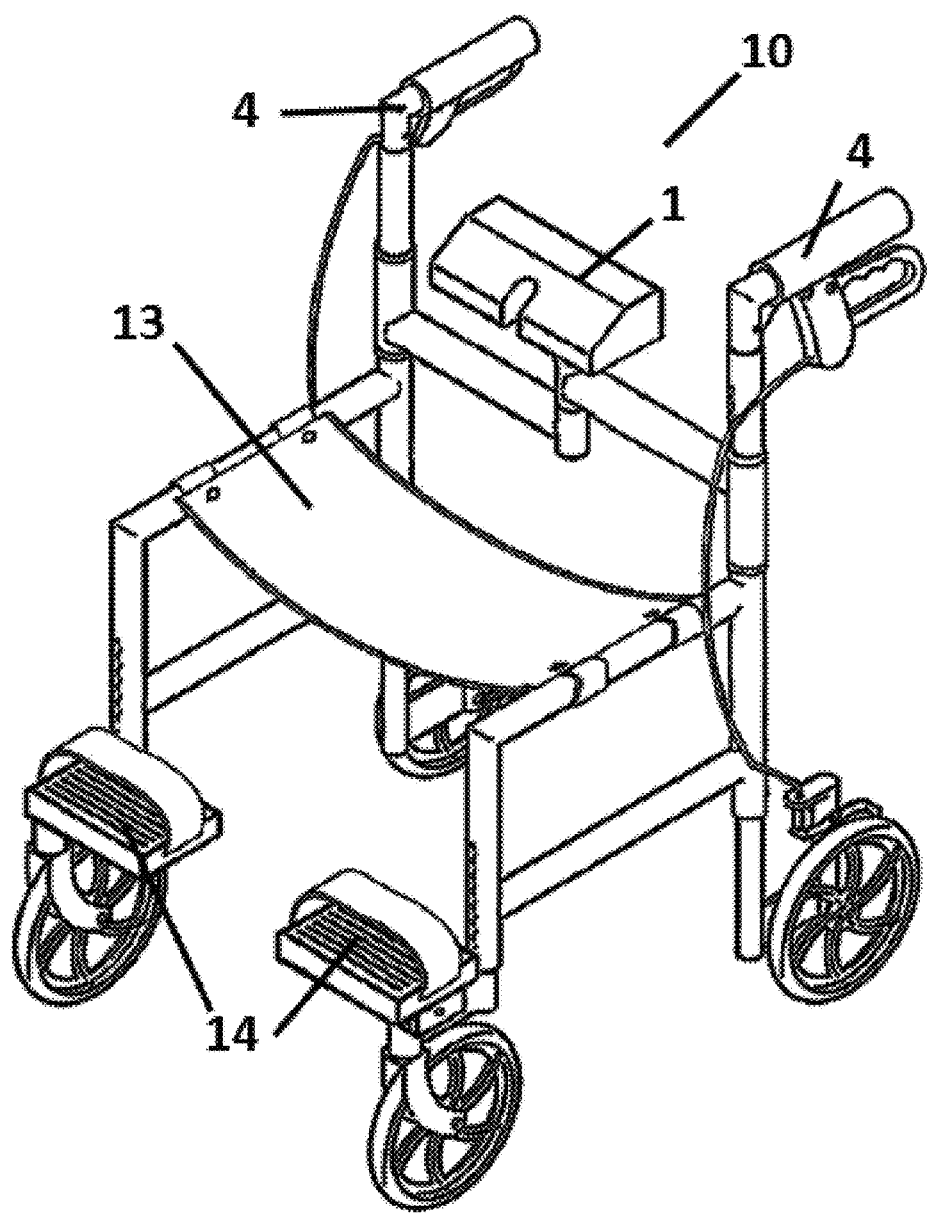
FIG. 35 shows an exemplary front perspective view of device 10 in optional configuration as a wheelchair.

FIG. 35 shows the optional device 10 configuration as a transport wheelchair. With the sling seat 13 installed, the handles 4 reversed in direction and the addition of foot rests 14, the user has the option of being pushed around by a second party. The walking seat 1 acts as a backrest for short-term use but an additional seat backrest (not shown) can be added for additional comfort for longer term use.

Next, "heavy-" and "light-" weight variations of a motorized option of the device 10 will be discussed. A heavyweight device leverages parts commonly used by motorized wheelchairs. The light-weight device replaces the rear (non-castor) wheel assemblies with independent motor-driven wheels. These are controlled by the user through a joy-stick which uses a controller unit that is also used on conventional joy-stick operated motorized wheelchairs. The motorized embodiments are described next.

Figure 36:
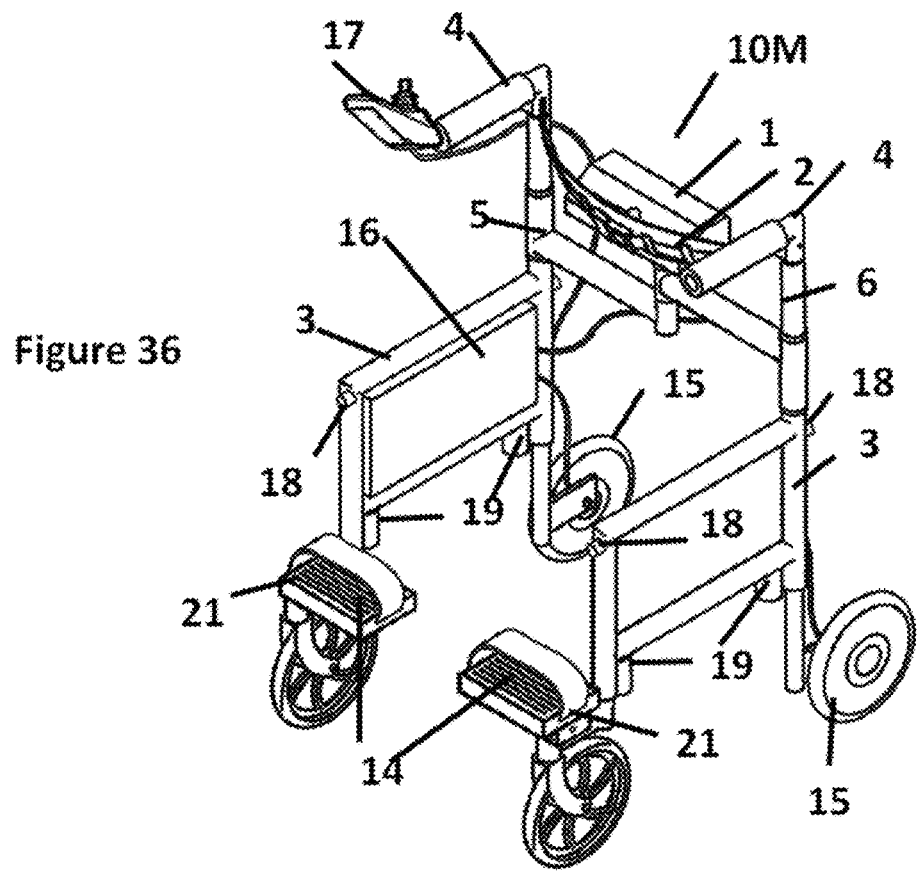
FIG. 36 shows an exemplary front perspective view of device 10M in optional lightweight motorized configuration.

FIG. 36 shows the device 10 conversion to a lightweight motorized mobility assistance device 10M. This configuration includes components common with device 10, including seat 1, belt 2, side frames 3, handles 4, hinge arm mechanism 5, and hinge posts 6. Device 10M operates in either power-assisted walking mode or full motorized mode.

With foot rests 14 installed, the device 10M is used for fully powered mobility assistance. Without the foot rests 14 installed, the user walks along as the motor assists by either partially or fully propelling the device. Either approach uses the joystick with LCD display 17, motor driven height adjustment capabilities leveraging caster wheel assemblies 21 and powered by hub wheel assemblies 15.

Hub wheel assemblies 15 include wheels that have the drive motors incorporated into the wheel itself. Height adjustment is accomplished through height adjustment motors 19. Device 10M has a controller unit 16 and sensors 18. Controller unit 16 takes the user instructions delivered through the joystick/LCD unit 17 to raise or lower the height, power the device forward, stop the device, and turn the device.

Sensors 18 are used by the controller unit 16 to "see" and avoid collisions with objects. These sensors 18 can also enable the device 10M automate operation. This includes detecting tracking tape or other means to determine location.

Figure 37:
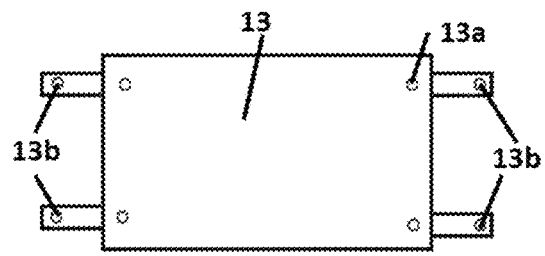
FIG. 37 shows an exemplary top view of sling seat.

FIG. 37 shows a top view of the sling seat 13. This seat is constructed of high strength fabric and is easily installed on device 10, 10M or other preferred embodiments by securing the sling seat 13 to side frames 3 using secure male and female latching connections 13a and 13b. Sling seat 13 rolls or folds into a convenient small form to be stowed when not in use.

Figure 38:
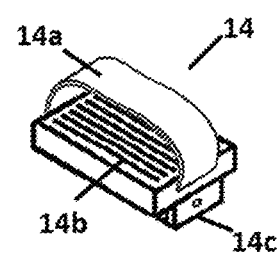
FIG. 38 shows an exemplary perspective view of foot rest.

FIG. 38 shows a perspective view of foot rest 14 which includes foot strap 14a, foot bed 14b, and footrest snap feature 14c that attaches to offset 7c of caster wheel assembly 7 or caster wheel assembly 21. Right and left foot rest 14 are identical, one is simply rotated 180 degrees and installed as compared to the other.

Figure 39:
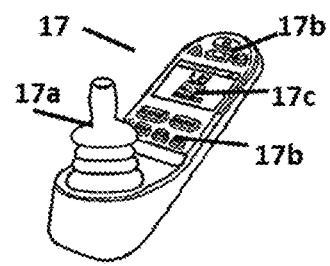
FIG. 39 shows an exemplary perspective view of joystick and LCD display.

FIG. 39 shows a perspective view of the joystick/LCD control unit 17. This unit includes the joystick 17a, button controls 17b and LCD display 17c. Joystick/LCD unit also has an interface for the user's smartphone. A user's smart phone can be used in place of the button controls 17b and LCD display 17c. The joystick/LCD control unit 17 can be operated in voice activation mode through the smartphone.

Figure 40:
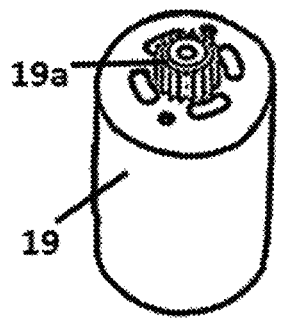
FIG. 40 shows an exemplary perspective view of height adjustment motor.

FIG. 40 shows the height adjustment motor 19 that includes a gear 19a that raises and lowers the device 20 height per instruction of the user through the joystick/LCD unit 17.

Figure 41:
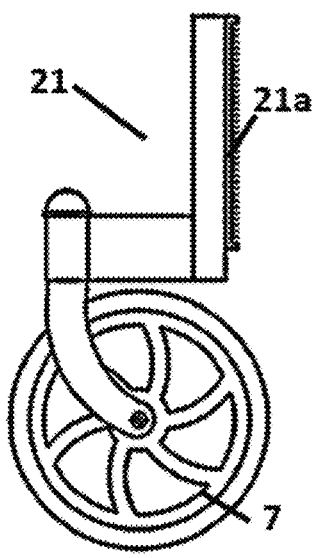
FIG. 41 shows an exemplary side view of caster wheel assembly for use with motorized height adjustment.

FIG. 41 shows caster wheel assembly 21 that includes linear travel feature 21a that is driven by height adjustment motor 19 and gear 19a to raise or lower the device 20.

Figure 42:
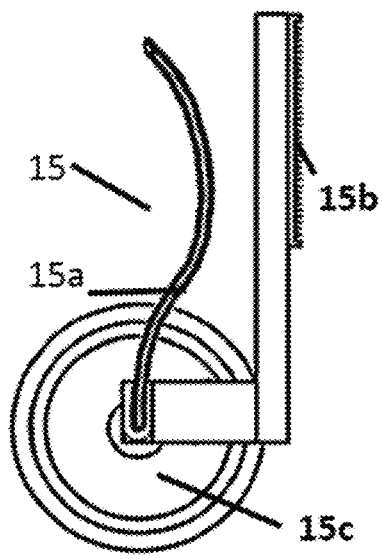
FIG. 42 shows an exemplary side view of hub wheel assembly.

FIG. 42 is the rear wheel assembly 15 that includes the hub wheel 15c, hub wheel power and control cable 15a, and linear travel feature 15b that is driven by height adjustment motor 19 and gear 19a to raise or lower the device 20.

Figure 43:
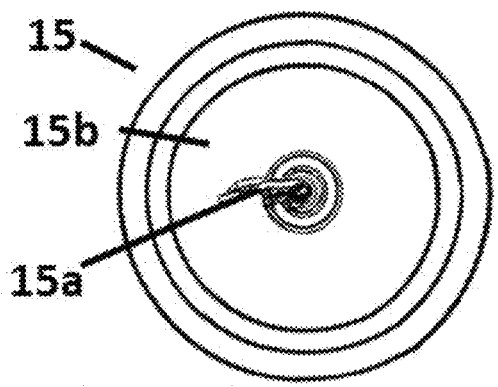
FIG. 43 shows an exemplary side view of hub wheel.

FIG. 43 is a side view of the hub wheel 15 that includes the hub wheel power and control cable 15a and the hub wheel motor cover 15b. By operating both left and right hub wheels 15 in synch at equal revolutions per minute (RPM) and the direction, device 10M moves either forward or backward accordingly. Device 10M can turn in a small radius when hub wheels are operated in opposite directions simultaneously. A wider turn can be achieved by operating the right hub wheel 15 at a higher RPM than the left hub wheel 15 to turn left and vice versa for the other direction. Directions for each hub wheel 15 speed and direction are provided from the joystick/LCD controller unit 17.

Figure 44:
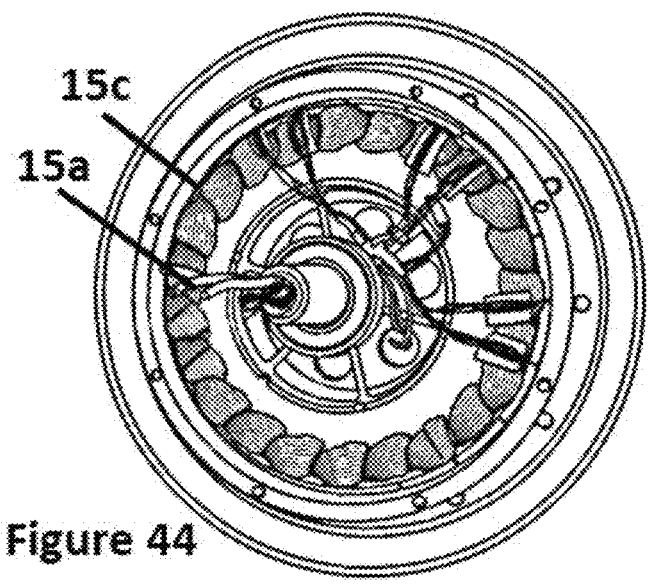
FIG. 44 shows an exemplary side view of hub wheel with internal motor features exposed.

FIG. 44 is a view of hub wheel 15 with the cover 15b removed to show the motor windings 15c and the power and control cable 15a. The hub wheel 15 allows the device 20 to be relatively lightweight but still maneuver similarly to the larger, heavier version described later.

Viewing FIGS. 43-44 in combination, the hub wheel motor 15 is enclosed by the hub cap or cover 15b and a tire supporting rim. A rubber wheel can be mounted on the rim. The hub cap has an opening through which a cable 15a is inserted therethrough. The cable 15a provides power as well as control signals to the motor. The cable 15a passes through the shaft to enter an internal chamber of the motor housing. The cable 15a has a plurality of electrical conducting wires which are connected to electronic components mounted on a printed circuit board. All wires are not shown and the number of the wires will vary based on control functions required. The printed circuit board is then fixedly mounted on a mounting plate in the motor. In one embodiment, the mounting plate is made of heat conductive material like aluminum and is fixedly attached by means of a set screw to the center shaft, which is capable of being rotated about rotational axis. It is to be noted that the rotational axis is located parallel to the longitudinal center axis. The locating of the parallel axis provides for smoother operation of the motor. Mounted interiorly of the motor are a series of magnets 15c. These magnets are located directly adjacent but slightly spaced from a series of radially located coils. There are multiple numbers of the coils each of which comprises electrically conductive wires that are wound about a series of radially disposed spokes called stator laminations, which are not shown. The outer, ring-shaped permanent magnet (stator) rotates and the inner metallic core (rotor) is fixed. When the motor is switched on, the static rotor stays still while the stator spins around it. The wheel rubber or tire is attached to the motor, and as the outer part of the motor rotates, the wheel (or wheels) powers the vehicle forward.

Sensors can be mounted in the hub wheel motor. An encoder such as a linear sensor, a capacitive sensor, a Hall-effect encoder or an LED based sensor can be used. For Hall effect sensors, by sensing the current provided to a load and using the device's applied voltage as a sensor voltage it is possible to determine the power dissipated by the motor. Hall effect devices used in motion sensing and motion limit switches can offer enhanced reliability in extreme environments. As there are no moving parts involved within the sensor or magnet, typical life expectancy is improved compared to traditional electromechanical switches. Additionally, the sensor and magnet may be encapsulated in an appropriate protective material. In one implementation, the Hall effect sensor is used as a direct replacement for the mechanical breaker points used in earlier automotive applications. Its use as an ignition timing device in various distributor types is as follows. A stationary permanent magnet and semiconductor Hall effect chip are mounted next to each other separated by an air gap, forming the Hall effect sensor. A metal rotor consisting of windows and tabs is mounted to a shaft and arranged so that during shaft rotation, the windows and tabs pass through the air gap between the permanent magnet and semiconductor Hall chip. This effectively shields and exposes the Hall chip to the permanent magnet's field respective to whether a tab or window is passing though the Hall sensor. A processor or controller can provide anti-skid functions for extended vehicle handling enhancements. The controller can also control the motor 15 to provide power regeneration. In one embodiment, a regenerative brake control circuit uses a chopper circuit which is first closed thereby to form a closed loop comprising at least a motor, a reactor and a chopper. The motor is used as a generator during the braking operation and therefore a current generated by the motor flows in the closed loop thereby to store electromagnetic energy in the reactor. A voltage drop in the chopper and other junction points is so small that the voltage across the reactor is substantially equal to the voltage generated by the motor. Next, the chopper is opened to thereby connect the series-connected motor and reactor to power source. The voltage across the motor and the reactor becomes higher than the source voltage and power is returned to the power source. With the decrease in the energy stored in the reactor, the voltage across the series-connected motor and reactor drops, and when it is decreased to a level lower than the source voltage, the current flowing to the power source is reduced accordingly to zero. By closing again the chopper circuit after the decrease of the current to the power source, the motor current is increased to thereby raise the voltage across the reactor again. Then, again connecting the motor circuit to the power source, a reverse current again flow to the power source. With repetition of the above process the motor current, that is, regenerative brake current can be controlled.

Figure 45:
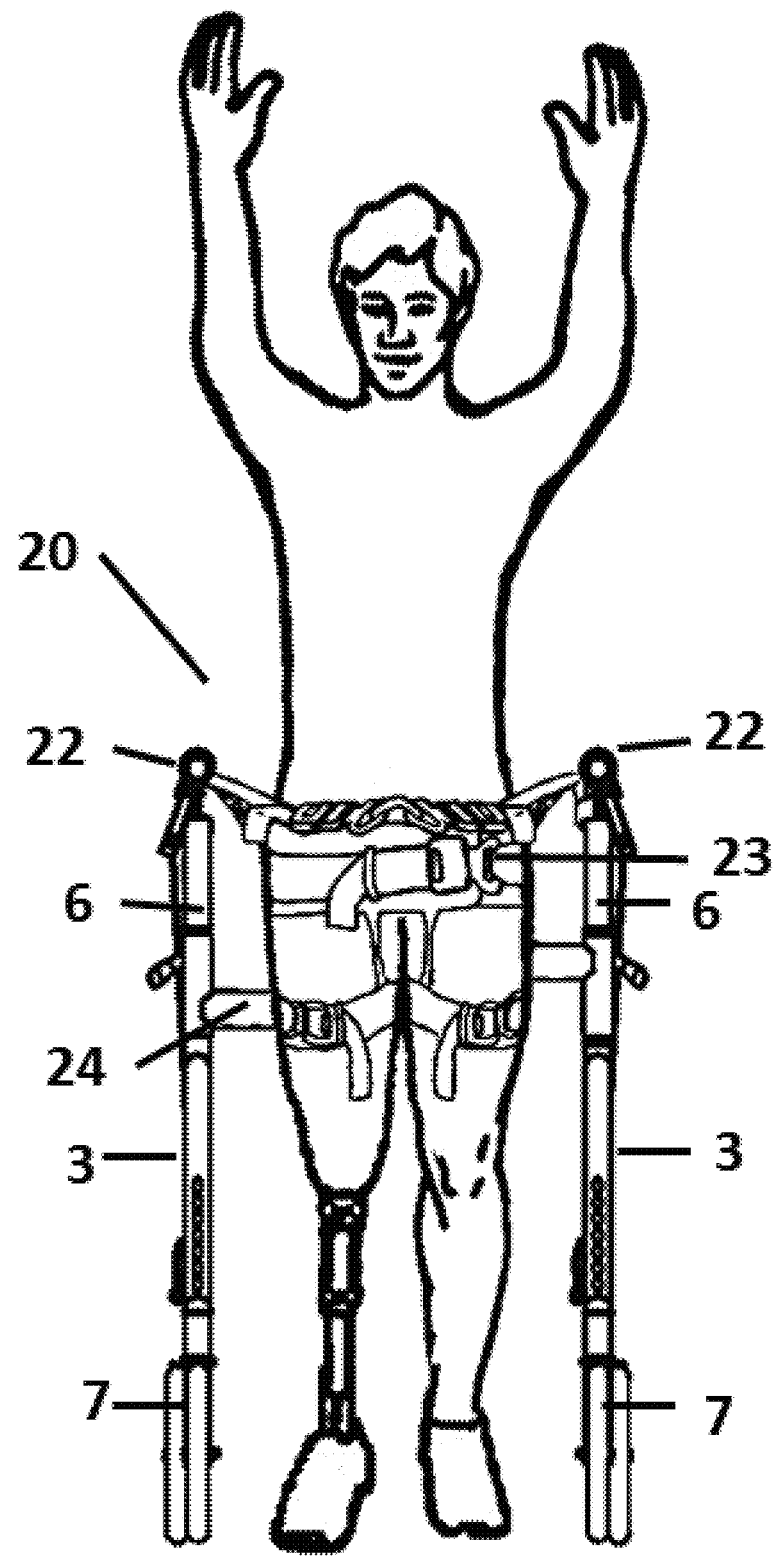
FIG. 45 shows an exemplary front view of device 20 with person.

FIG. 45 shows a front view of mobility assistance device 20 with a person positioned in the device. Device 20 replaces the walking seat 1 and belt 2 with harness 23. The user's weight (as much as 100%) is transferred from the user's legs through harness 23. When operating the device 20, the user walks by using as much or as little force as desired (or comfortable) through one or both of their legs. Caster wheel assembly 7 and rear wheel assembly 8 allow both turning and forward movement with a minimum of force required through the users legs so that user's with even severe limitations can safely and conveniently propel themselves about. In these regards, device 20 is considered functionally equivalent to device 10.

Also shown in FIG. 45 are the primary structural components of device 20. These include two side frames 3, two handles 22, a hinge arm mechanism 24, and 2 hinge posts 6. The harness 23 is rigidly attached to handles 22, which connects through the hinge posts 6, to side frames 3 while securing the hinge arm mechanism 24. These structural members are essentially identical to device 10 with the exception of hinge arm mechanism 24 which does not have the accommodation for the walking seat 1 and handles 22 are extended in length to accommodate harness 23. The device of FIG. 45 can be used in conjunction with a rehabilitation therapy process. The user, under the direction of a physical therapist or other health professional, transitions in position from a mostly seated posture to a fully or nearly fully standing posture over the course of therapy. The user would start with the device in a relatively low setting so that the legs project more forward from the device similar to when sitting in a chair. As the therapy proceeds and the user improves and gains proficiency, the device height is raised in small increments. This process continues until the user assumes as vertical standing posture as deemed appropriate by the directing health professional. If the user is done with the therapy and no longer requires the device (such as for a surgically repaired knee, for example) the user can resume walking without the device. If the user will continue to require the device to enable walking for the indefinite future (such as for a permanent leg disability, for example), the device will remain more or less at this setting going forward.

Figure 46:
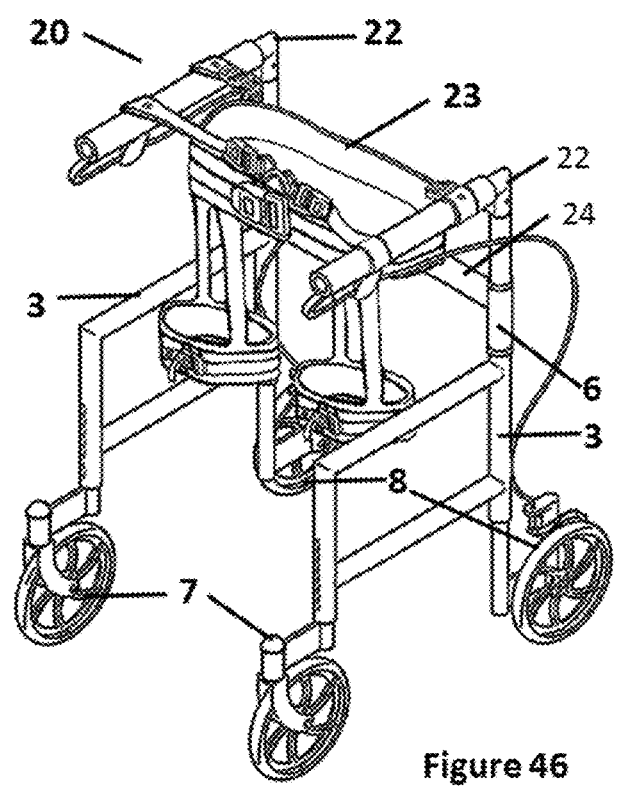
FIG. 46 shows an exemplary perspective view of device 20.

FIG. 46 shows device 20 in a front perspective view which includes two side frames 3, two caster wheel assemblies 7, two rear wheel assemblies 8, two handles 22, a hinge arm mechanism 24, and hinge post 6. The harness 23 is rigidly attached to handles 22, which connects through the hinge posts 6, to side frames 3 while securing the hinge arm mechanism 24. Hinge arm mechanism 24 is perpendicular to the side frames 3. Rear wheel assemblies 8 extend towards the rear of device 20 in alignment with side frames 3. Caster wheel assemblies 7 similarly extend forward in alignment with side frame 3 (in opposite direction as rear wheel assemblies 8). This is the orientation of device 20 when operated by the user.

Figure 47:
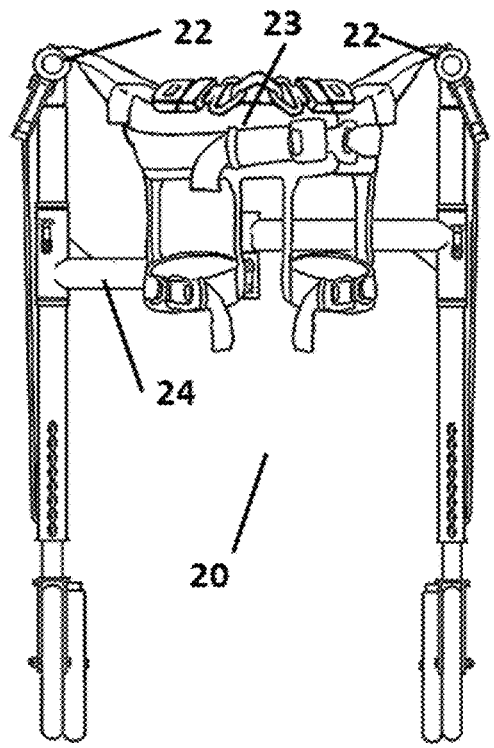
FIG. 47 shows an exemplary front view of device 20.
Figure 48:
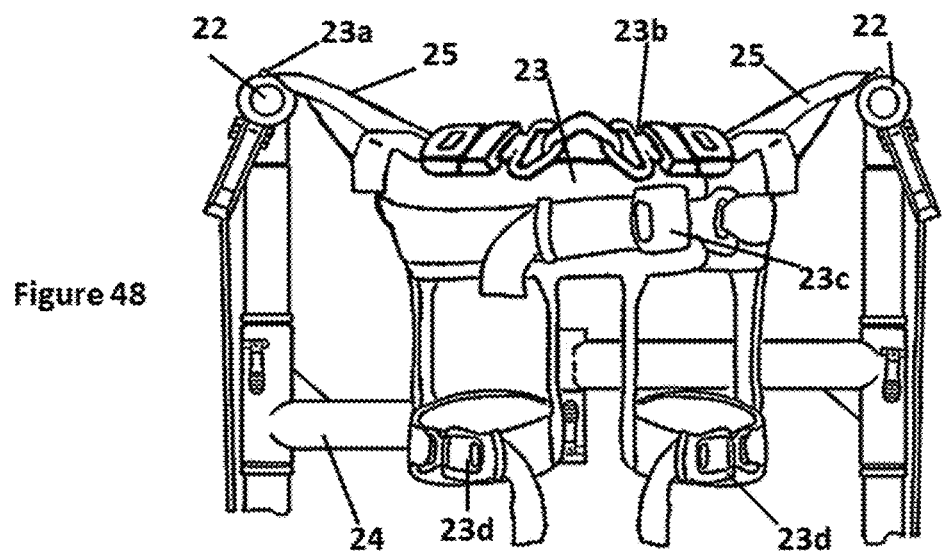
FIG. 48 shows an exemplary front detail view of harness installed on device 20.

FIG. 47 shows the fully open front perspective view of device 20 showing another view of harness 23 connected to handles 22. FIG. 48 shows a front view of harness 23 connected to handles 22 through attachment straps 25. Harness 23 is held securely by bolt 23a at approximately at the same height as handles 22. This view shows harness latches 23b, waist belt 23c and leg belts 23d. The weight of the user is supported by a combination of waist belt 23c and leg belts 23d and transferred to handles 22 by attachment straps 25. This is functionally equivalent to device 10's use of walking seat 1 and belt 2 in supporting and transferring the user's weight.

Figure 49:
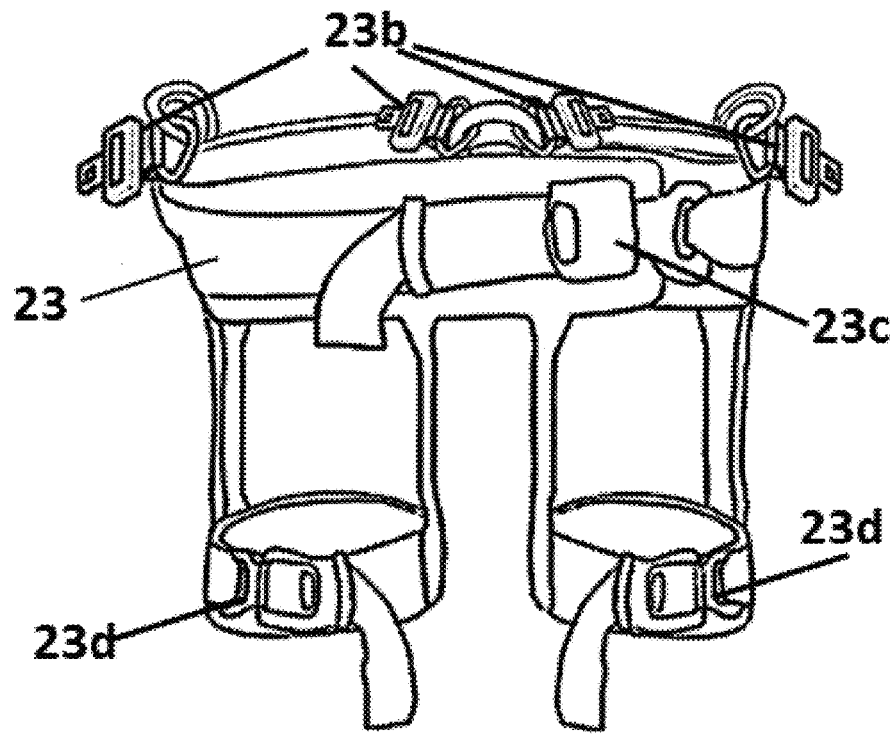
FIG. 49 shows an exemplary front view of harness.
Figure 50:
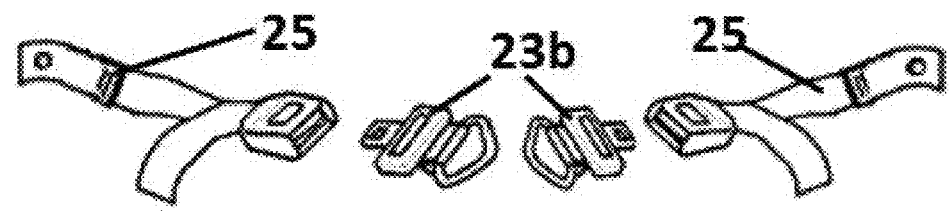
FIG. 50 shows an exemplary detail of harness attachment features.

FIG. 49 is a front view of the harness 23 again showing the details of harness latches 23b, waist belt 23c and leg belts 23d, while FIG. 50 shows attachment straps 25 and depicts how they latch and can be separated from harness 23 and harness latches 23b.

Figure 51:
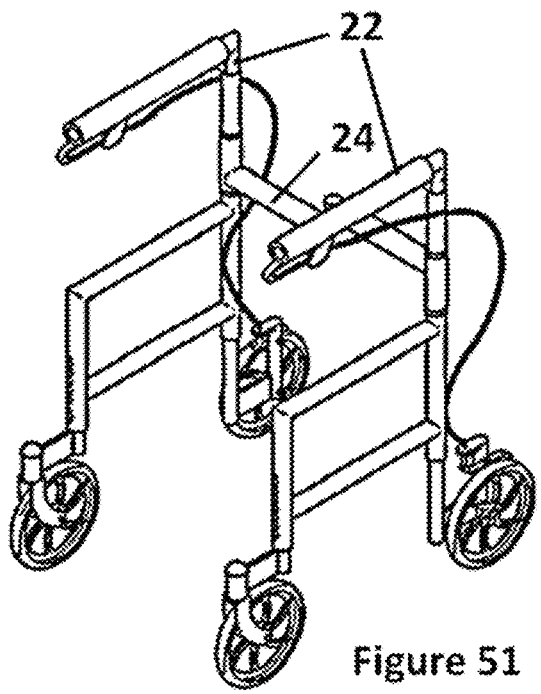
FIG. 51 shows an exemplary perspective view of device 20 without harness.
Figure 52:
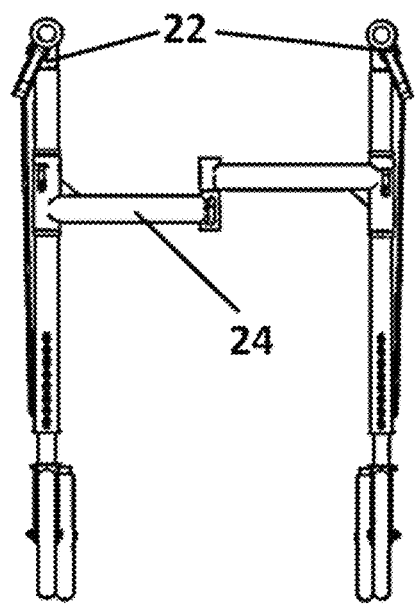
FIG. 52 shows an exemplary front view of device 20 without harness.

FIG. 51 is a front perspective view of device 20 without the harness 23 to show how the form of handles 22 and hinge arm 24 differs from the corresponding elements of device 10 but how the structure is otherwise similar. FIG. 52 is a front view of device 20 without the harness 23 to show how the form of hinge arm 24 differs from the corresponding element of device 10 but how the structure is otherwise similar.

Figure 53:
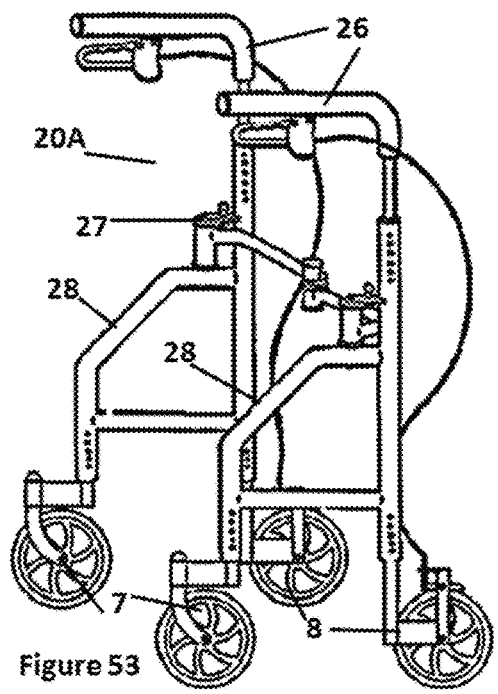
FIG. 53 shows an exemplary perspective view of alternative version of device 20A.

FIG. 53 shows an alternative form of the device 20A, including a variation on handles 26, the hinge arm mechanism 27, and side frames 28. Device 20A similar is shown without the harness 23 attached for clarity in this view. Device 20 shares many common components with devices 10 and 20, including caster wheel assemblies 7 and rear wheel assemblies 8.

Figure 54:
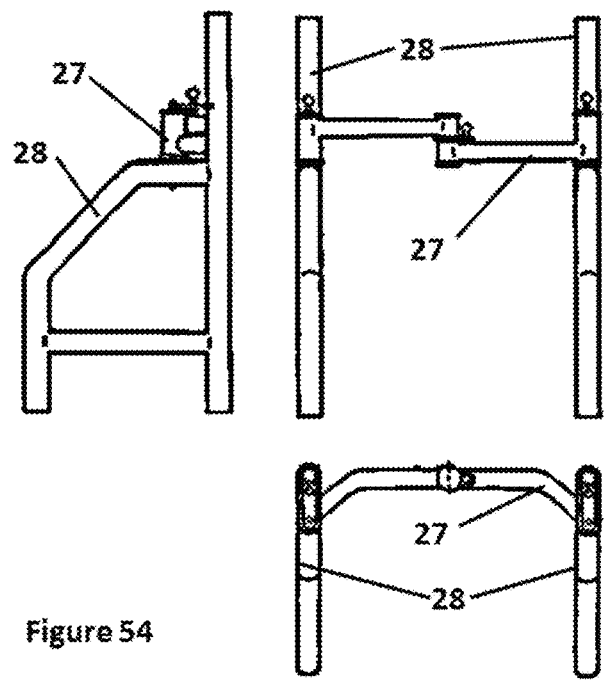
FIG. 54 shows an exemplary Side, front and top view of device 20A without handles and wheels.
Figure 55:
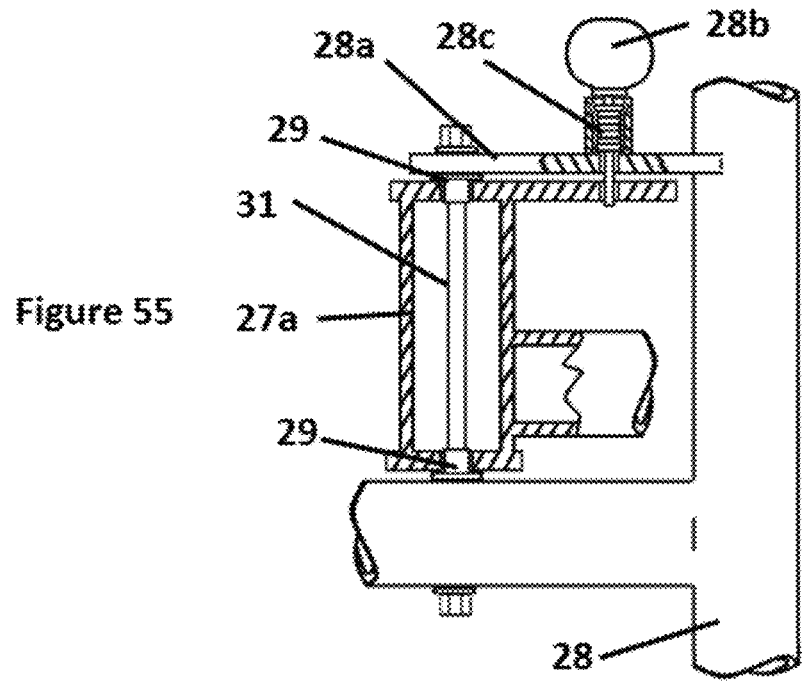
FIG. 55 shows an exemplary detail cut-away view of hinge features for device 20A.

FIG. 54 shows side, front and top views of the structural elements of device 20A, including side frames 28 and hinge arm mechanism 27. FIG. 55 shows a detail cut-away view of the hinge and locking features of device 20A. Side frame 28 contains pull-pin 28b mounted on flange 28a to rigidly lock the position with hinge arm mechanism 27. Pull pin 28b includes spring 28c. Pulling up on the pull pin 28b withdraws a pin and allows free axial movement around the hinge bolt 31 contained in hinge cylinder 27a. The hinge swings freely due to bearings 29. This hinge and locking mechanism is functionally equivalent to the mechanism described earlier for device 10.

Figure 56:
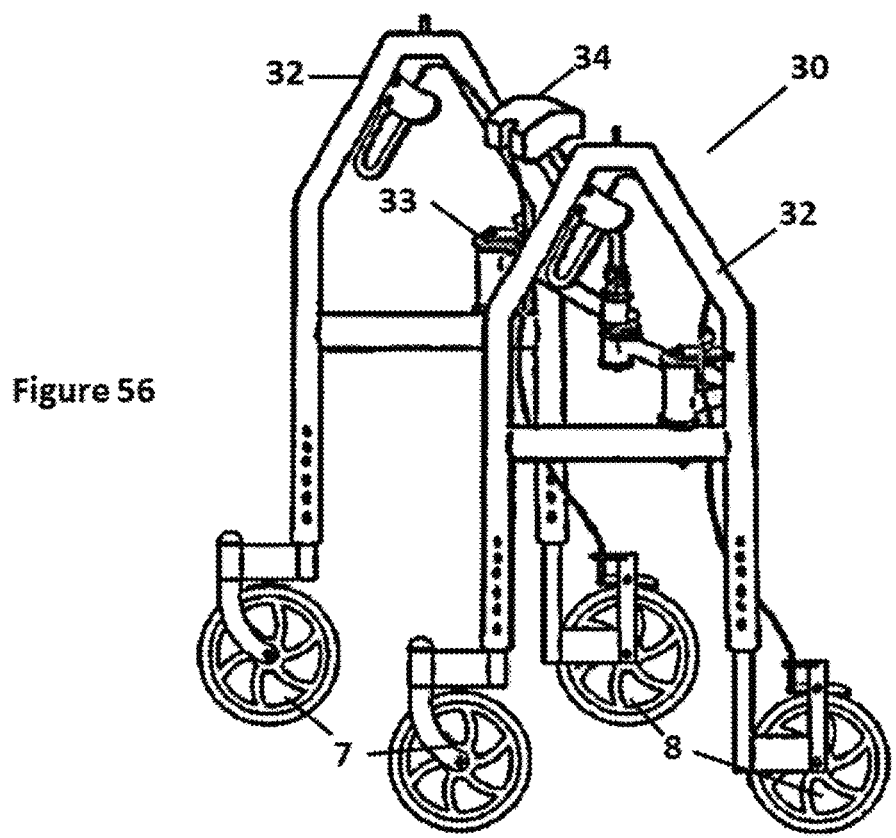
FIG. 56 shows an exemplary perspective view of device 30.

FIG. 56 shows a front perspective view of another form of the mobility assistance device 30. Device 30 shows alternative design for side frame 32. The view does not show belt 2 that is used with device 30. Hinge arm mechanism 33 is essentially similar to hinge arm mechanism 27 of device 20 except that it includes the seat attachment features similar to hinge arm mechanism 5 of device 10. Walking seat 34 is similar to walking seat 1 of device 10 but is depicted slightly differently. When operating the device 30, the user walks by using as much or as little force as desired (or comfortable) through one or both of their legs. Caster wheel assembly 7 and rear wheel assembly 8 allow both turning and forward movement with a minimum of force required through the users legs so that user's with even severe limitations can safely and conveniently propel themselves about.

Figure 57:
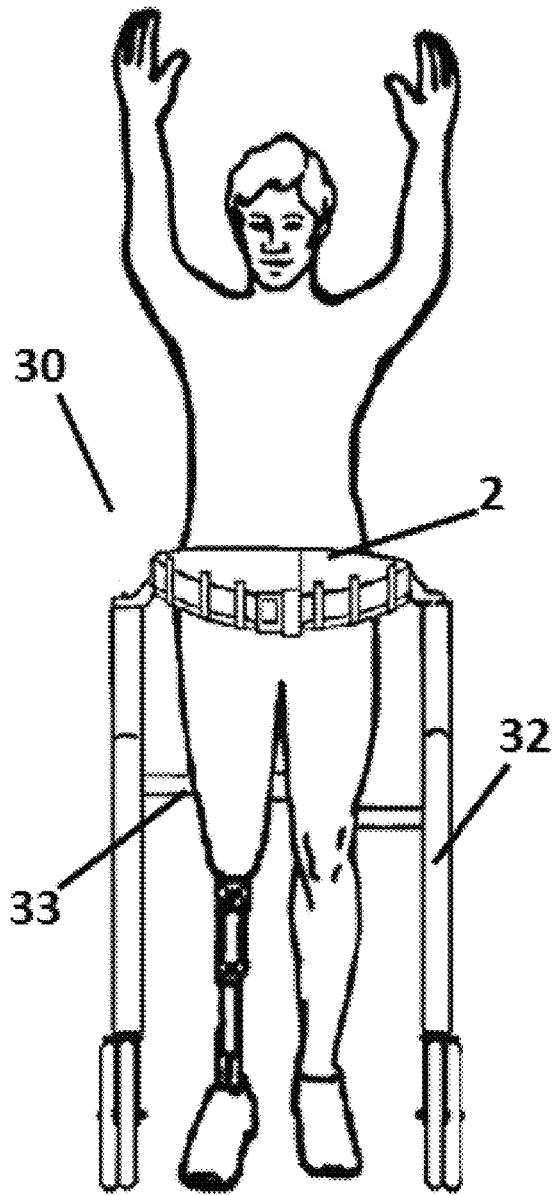
FIG. 57 shows an exemplary front view of device 30 with person.

FIG. 57 shows a front view of device 30 including a person positioned in the device. Device 30 is functionally similar to device 10, however device 30 is designed to allow more unrestricted movement of the user's upper body. Device 30 has no elements that protrude above the user's waist. In particular Device 30 provides the user more freedom of movement of the upper body because of the lack of handles. Some advanced user may prefer device 30 without the braking features shown in later figures.

Figure 58:
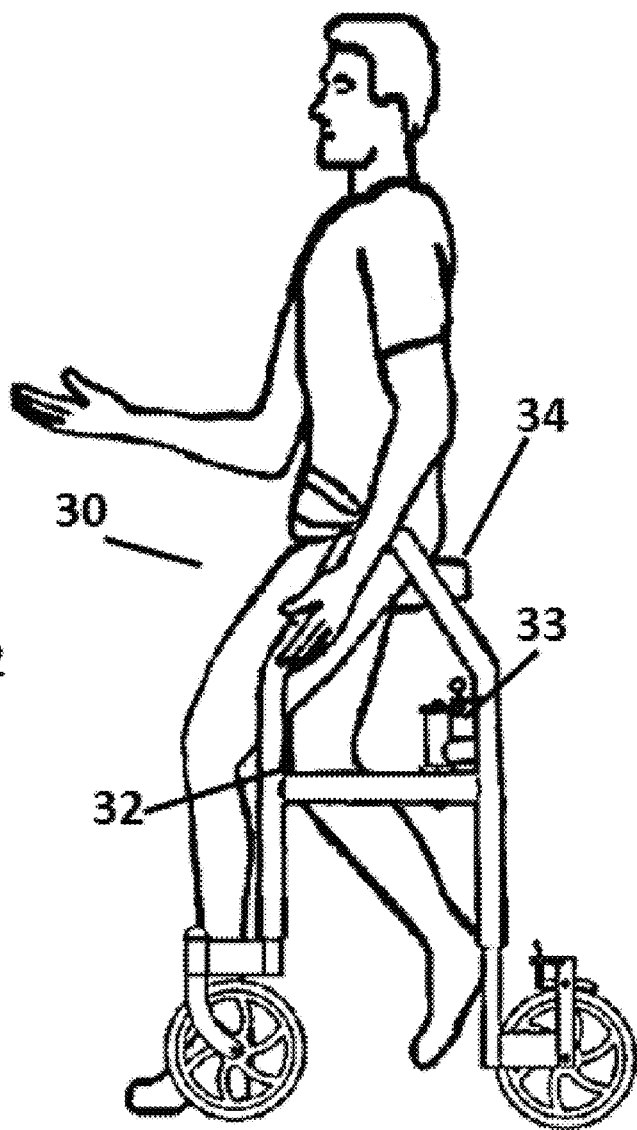
FIG. 58 shows an exemplary side view of device 30 with person.

FIG. 58 shows the side view of device 30 including a person walking. The view shows that no components of the walker extend beyond the user's waist thereby providing freedom of movement of the upper body.

Figure 59:
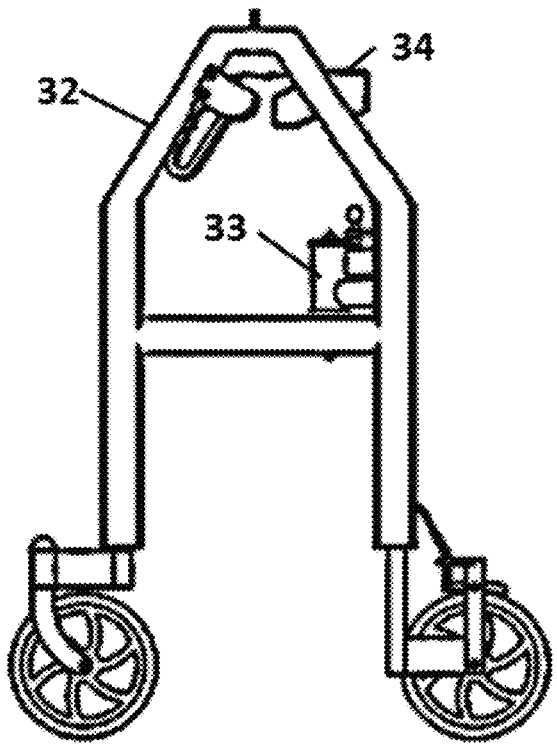
FIG. 59 shows an exemplary side view of device 30.
Figure 60:
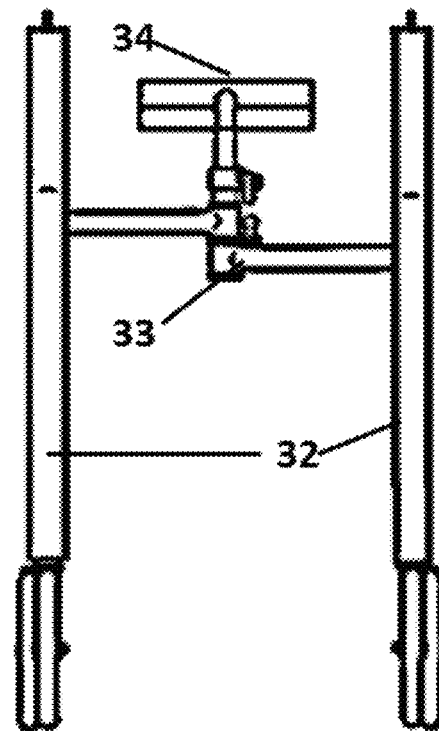
FIG. 60 shows an exemplary front view of device 30.
Figure 61:
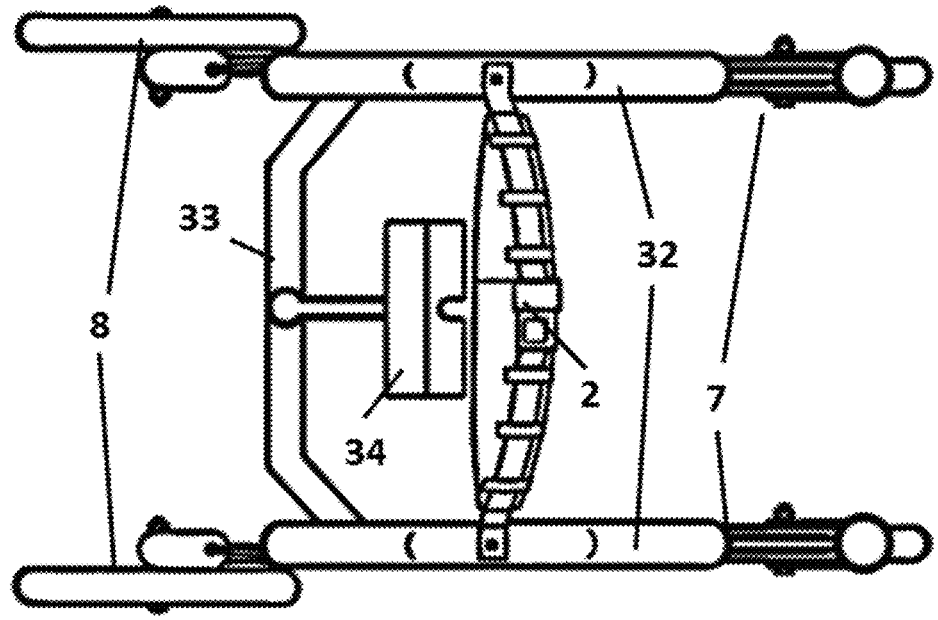
FIG. 61 shows an exemplary top view of device 30.

FIG. 59 shows the side view of device 30 not including the belt 2, while FIG. 60 shows the front view of the device 30 not including the belt 2. FIG. 61 shows a top view of device 30 including belt 2.

Figure 62:
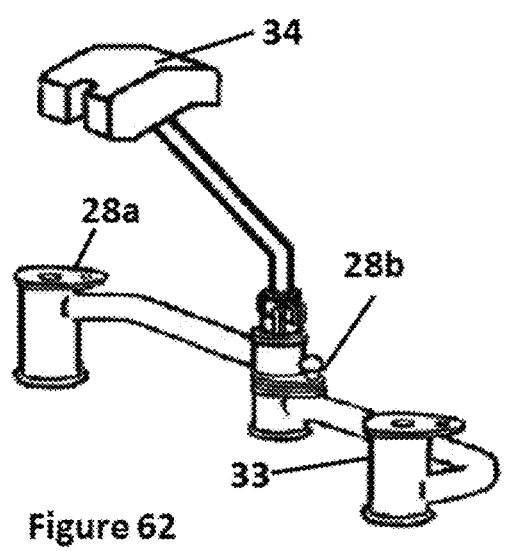
FIG. 62 shows an exemplary perspective view of hinge arm mechanism assembly with walking seat for device 30.
Figure 63:
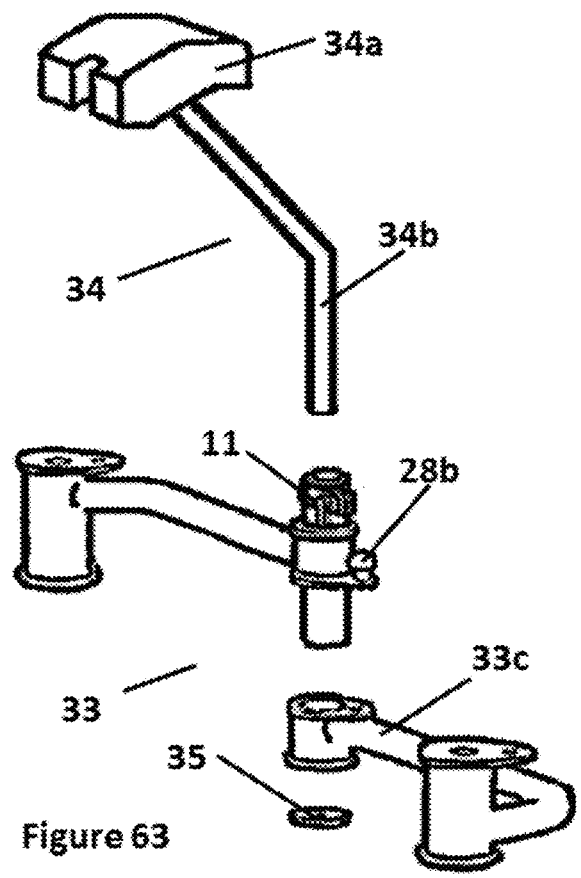
FIG. 63 shows an exemplary perspective exploded view of hinge arm mechanism with walking seat for device 30.

FIG. 62 shows the hinge arm mechanism 33 in front perspective with the walking seat 34 installed. Hinge arm mechanism 33 is show in its open and locked form, locked by pull pin 28b. FIG. 63 shows an exploded front perspective view of the hinge arm mechanism 33 and walking seat 34. The seat attachment feature includes a cam lever lock 11. The primary difference between walking seat 1 and walking seat 34 is the bent seat post 34b.

Figure 64:
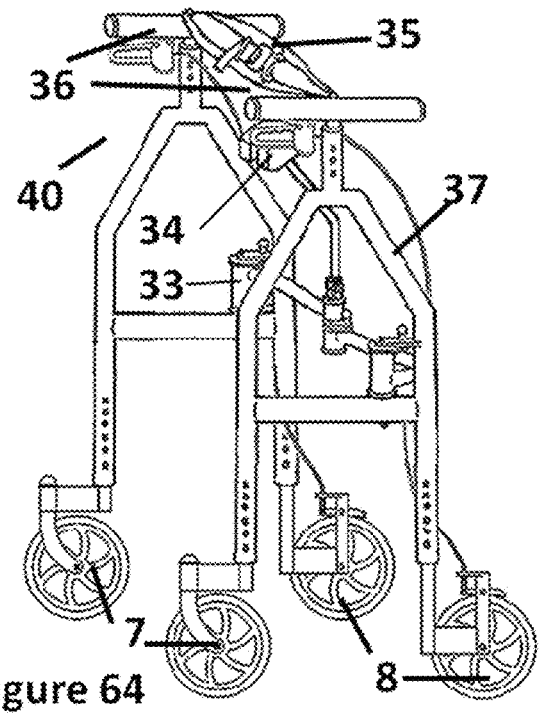
FIG. 64 shows an exemplary perspective view of device 40.

FIG. 64 shows a side perspective view of another form of the mobility assistance device 40. Device 40 shows alternative design for side frame 37. The view shows belt 2 that is used with in conjunction with walking seat 34 to fixedly hold the user in place. Device 40 uses the same hinge arm mechanism 33 walking seat 34 of device 30. The primary difference between device 40 and device 30 is the inclusion of handles 36. These handles 36 are in the form of a "tee"

and provide a comfortable place for the user to hold onto, should they choose. When operating the device 40, the user walks by using as much or as little force as desired (or comfortable) through one or both of their legs. Caster wheel assembly 7 and rear wheel assembly 8 allow both turning and forward movement with a minimum of force required through the users legs so that user's with even severe limitations can safely and conveniently propel themselves about.

Figure 65:
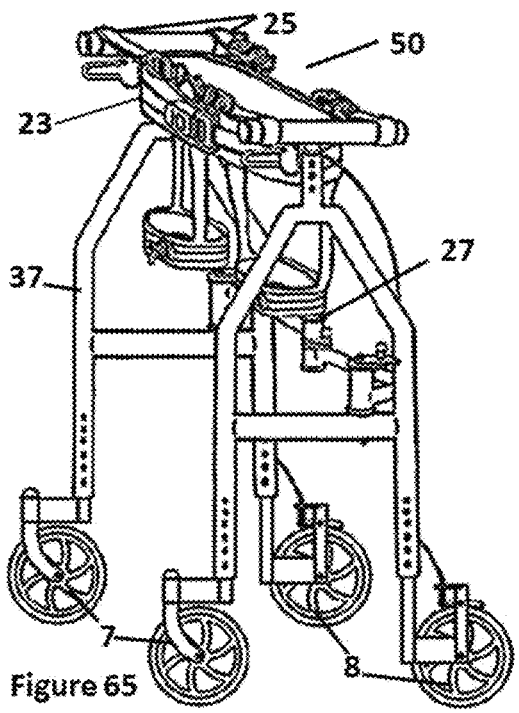
FIG. 65 shows an exemplary perspective view of device 50.

FIG. 65 shows a side perspective view of another form of the mobility assistance device 50. Device 50 uses harness 23 to secure the user into position. Device 50 uses the same hinge arm mechanism 27 of device 20. Device 50 otherwise uses essentially the same components as device 40. When operating the device 40, the user walks by using as much or as little force as desired (or comfortable) through one or both of their legs. Caster wheel assembly 7 and rear wheel assembly 8 allow both turning and forward movement with a minimum of force required through the users legs so that user's with even severe limitations can safely and conveniently propel themselves about.

Figure 66:
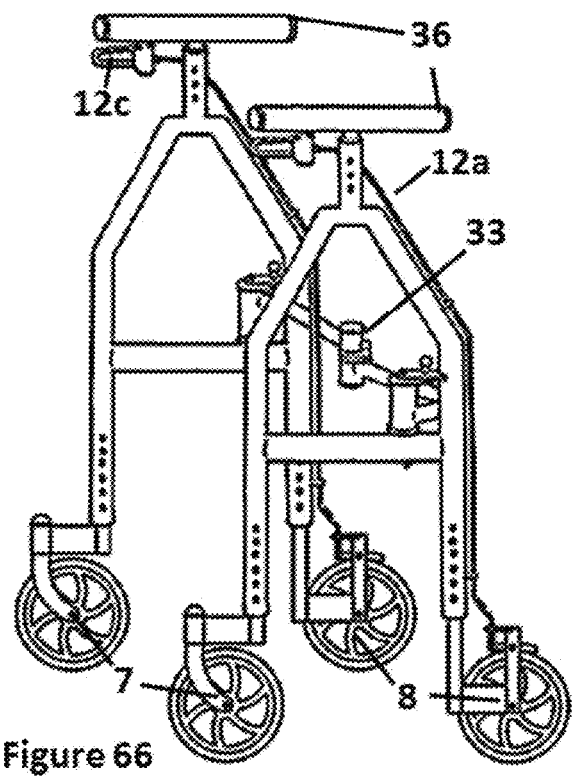
FIG. 66 shows an exemplary perspective view of device 50 showing brake features, but no harness.

FIG. 66 shows a side perspective view of device 50 without the harness 23 to more clearly show the form of device 50.

Figure 67:
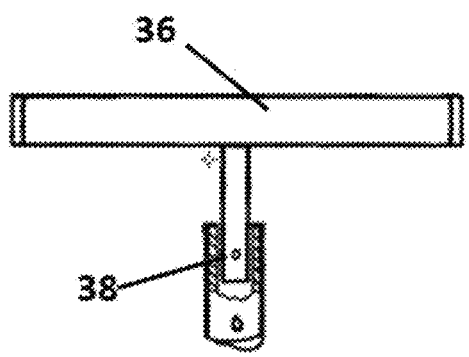
FIG. 67 shows an exemplary side view of handle for device 50.

FIG. 67 shows the handle 36 used for both device 40 and device 50. The handle height adjustment features a similar spring button as used in device 10.

Figures 68, 69:
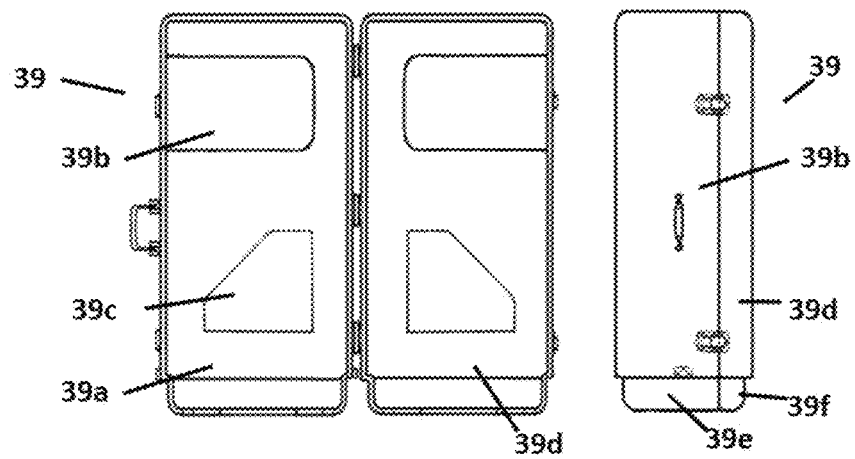
FIG. 68 shows an exemplary front view of open travel case.
FIG. 69 shows an exemplary side view of closed travel case.

FIG. 68 shows an open view of the carrying case 39 that includes left side 39a, right side 39d, foam padding 39b and 39c, while FIG. 69 shows carry case 39 in closed state. Feature 39e mates securely into bottom wheel housing 41, shown in more details in FIG. 70.

Figure 70:
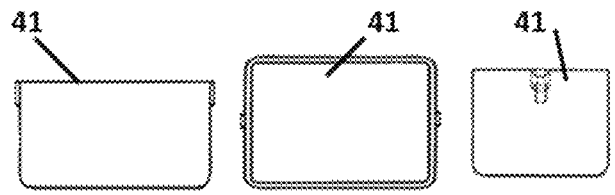
FIG. 70 shows an exemplary front, top and side views of bottom wheel housing for travel case.

FIG. 70 shows bottom wheel housing 41. Bottom wheel housing 41 is separable from case 39 to allow the person transporting the device to roll the walker and case, if they so choose to do so rather than to carry it.

Figures 71, 72:
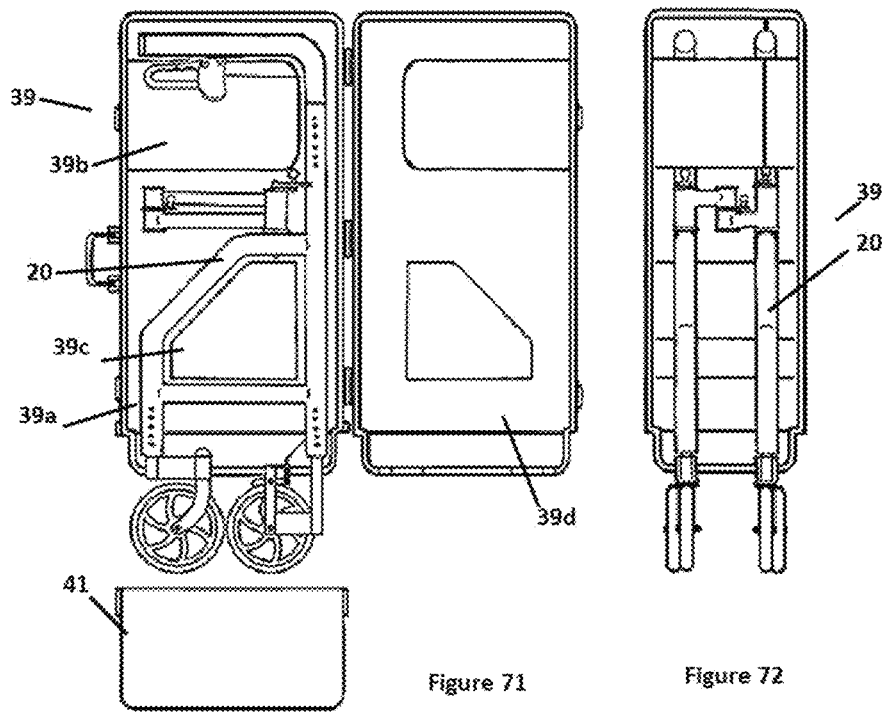
FIG. 71 shows an exemplary front view of open travel case with device.
FIG. 72 shows an exemplary side cut-away view of travel case with device.

FIG. 71 shows the walker installed in the open carrying case 39 and wheel housing 41 is necessarily not installed at this state. FIG. 72 shows a side cutaway section view of the carrying case 39 with a walker and without the bottom wheel housing 41 installed. FIG. 73 shows a side view of the carrying case 39 with a walker and without the bottom wheel housing 41 installed. FIG. 74 shows a side view of the carrying case 39 with the bottom wheel housing 41 installed.

FIG. 75 shows a front perspective of the heavyweight motorized mobility assistance device 60. Device 60 uses the side frames 32, hinge arm mechanism 33, seat 34 from device 30 with joystick/LCD 17 of device 10M. Device 60 also uses belt 2, but not shown in this view for clarity. These are mounted on powered sled 43. The user operates the device similarly to device 10M. Device 60 is suitable for use in similar settings as motorized wheelchairs. It is more capable of handling deficits in the surface over which it travels as compared to device 10M. Similar to device 30, it does not have handles.

FIG. 76 shows a front perspective of the heavyweight motorized mobility assistance device 70. Device 70 uses side frames 28, handles 26, hinge arm mechanism 33, seat 34 with joystick/LCD 17 of device 10M. Devise 70 also uses belt 2, but not shown in this view for clarity. These are mounted on powered sled 43. The user operates the device similarly to device 10M. Device 70 is suitable for use in similar settings as motorized wheelchairs and scooters. It is more capable of handling deficits in the surface over which it travels as compared to device 10M.

Figure 77:
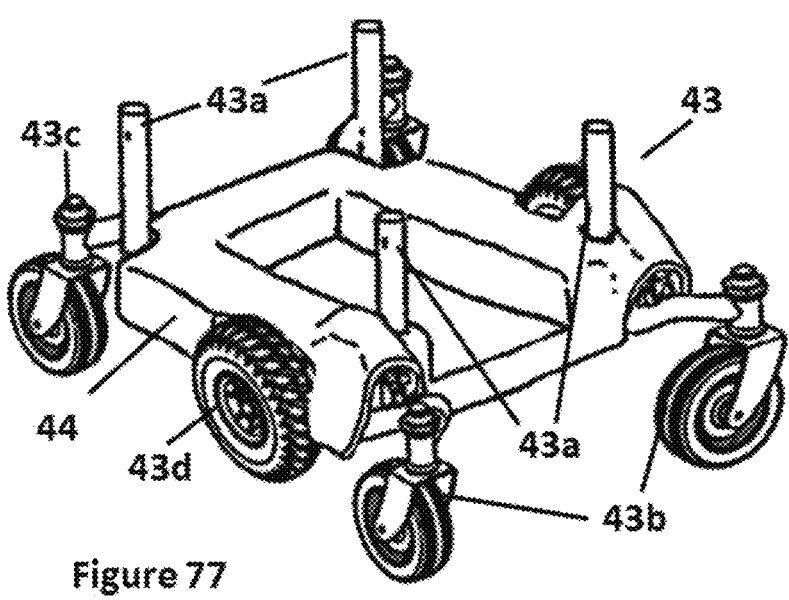
FIG. 77 shows an exemplary perspective view of powered sled.

FIG. 77 shows a perspective view of the powered sled 43, including mounting shafts 43a to fasten to side frames 32 or 28, front caster wheels 43b, rear caster wheels 43c, drive wheels 43d and sled cover 44. Both sets of caster wheels can rotate 360 degrees without restriction.

Figure 78:
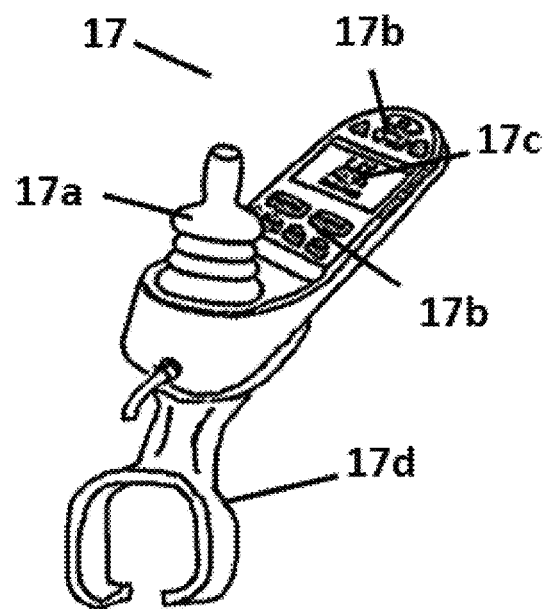
FIG. 78 shows an exemplary perspective view of joystick and LCD.

FIG. 78 shows joystick/LCD unit 17 with mount 42 for use on device 60. In this embodiment, the LCD unit can be a dedicated LCD driven by a processor electrically coupled to the joystick and LCD and programmed to actuate the motor as desired. A system host controller is responsible for managing all aspects of the device 10M, 60 or 70 operation. It determines operation of the device 10M, 60 or 70 based on the appropriate stimuli for the device's mode of operation. The controller captures input controls for "forward and reverse" motion and "left right" steering. The system receives any commands from a control panel and drives the motors at selected speed. Maintenance mode will override any setting of the mode switch except parked. When in parked mode the controller controls the drive control section so that the motors and or gearboxes are in neutral mode and no brake or lock is applied. When in parked mode, the controller controls the drive control section such that the motors are disabled and the gearboxes and or brakes are applied. The controller manages all auxiliary functions of the device including the selection and indication of operational modes as well as interlocks that are interference or safety related. The controller takes input from a collision detection system, collision avoidance system and or keep out systems and controls movement in accordance with prescribed parameter base data. The controller controls all LED operating status indication. The controller provides audible annunciation by way of Beeps for any status change. The controller maintains a logging process of all device operation and use that can be extracted for external analysis if required. The controller maintains a register of allowable hours of use and will prevent commencement of operation if the hours have been exceeded. The controller monitors battery condition and will advise if battery health has diminished below a preset operating margin. The controller has provision for data and software update via a computer port such as a USB port. The controller has provision for in device 10M, 60 or 70 updating of allowable hours such updating to be by either keypad encrypted entry triggered from the host controller serial number or by USB port with an encrypted update and destroy process. The monitoring of the number of hours of use allow the system to track when power will be low and thus halt operation of the unit before power failure.

The system preferably has the capability of recording the operational time of the device 10M, 60 or 70. Preferably the device 10M, 60 or 70 can alert a remote monitoring system whether the operational time is approaching its allocated time. Preferably all usage of the device 10M, 60 or 70 is recorded. The device 10M, 60 or 70 preferably has an override system where the electrical current powering the wheels 15 or 43d increases up to a threshold level to keep the wheels turning. When the threshold level is reached or exceeded the current to the motor is preferably stopped. The override system is preferably activated when the device 10M, 60 or 70 moves up a very steep slope, when there is too much weight on the device 10M, 60 or 70 and when one or more wheels lose traction. In another embodiment the device 10M, 60 or 70 may have a weight sensor that detects whether the weight of the device 10M, 60 or 70 is over a predetermined limit and if so the device 10M, 60 or 70 stops. In another embodiment the device 10M, 60 or 70 may have a lateral sensor to detect sideways tipping movement of the device 10M, 60 or 70. In another embodiment the device 10M, 60 or 70 may have a gradient sensor that is able to sense the incline of a gradient and if over a predetermined limit, the processor will prevent the device 10M, 60 or 70 from continuing movement in the inclined direction.

In other embodiments, the controller can be a smart phone running suitable software to control the motors through a wireless link such as Bluetooth (or a wired link). The phone would include the LCD and would receive input from the joystick by USB cable or by Bluetooth transmissions.

In yet other embodiments, the device 10M, 60 or 70 has a collision avoidance system that enables the device 10M, 60 or 70 to avoid or stop before it contacts an object. The device 10M, 60 or 70 may include a collision avoidance system that has a plurality of infrared ranging transceivers spaced about the device 10M, 60 or 70. The collision avoidance system preferably includes infrared charge coupled device (CCD) range sensors located about the device 10M, 60 or 70 and capable of detecting objects between 0.01 and 5 meters and more preferably up to 1.6 meters from the sensor. The collision avoidance system can have guard bands that provide an outer boundary and an inner boundary about the device 10M, 60 or 70. Preferably an alarm and or response in accordance with the processor programming is actuated when an object enters the outer or inner boundaries. The outer boundary is preferably set between 1 and 2 meters and more preferably 1.2 meters from the device 10M, 60 or 70. The inner boundary is preferably set between 0.01 and 1 meters and more preferably 0.3 meters for the front of the device 10M, 60 or 70 and 0.08 meters for the sides of the device 10M, 60 or 70. Preferably there are rules forming part of the processor programming that direct the operation of the device 10M, 60 or 70 when an object is detected by the infrared CCD sensors. The device 10M, 60 or 70 may also include a satellite navigation system to assist in controlling the movement of the device 10M, 60 or 70 in a defined area. Alternatively, markers can be sensed by the controller to guide device movement to reach a predetermined location in the house, for example. Such markers can be wireless or can be magnetic or optical. For example, a line sensor can track and detect the line. The line sensor can be made using IR sensors. The position\number of these sensors depends on the complexity of the track to be solved. Once the position of the device 10M, 60 or 70 on the line is read, a decision has to be made to move the device so that the line is in the center of the device. Various other local positioning methods known to those skilled in the art can be used.

Figure 79:
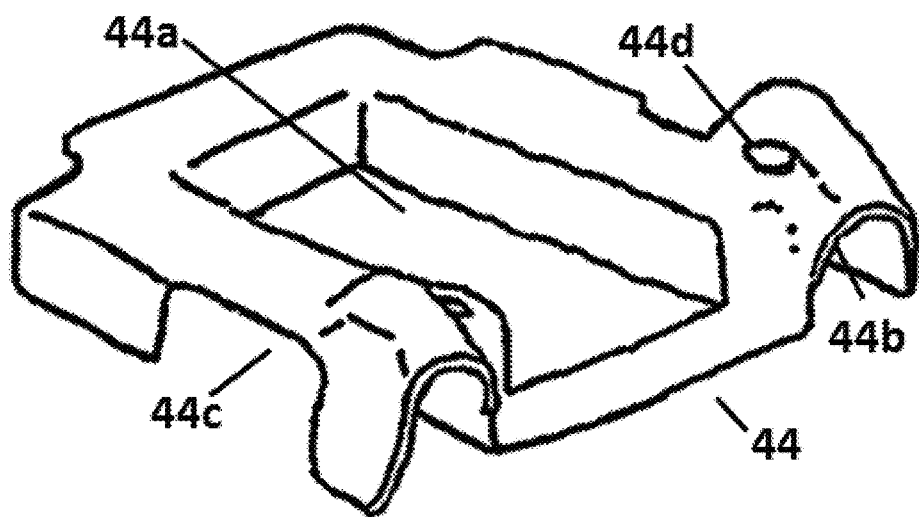
FIG. 79 shows an exemplary perspective view of sled cover.

FIG. 79 shows a perspective view of sled cover 44 that includes foot bed 44a, mounting shaft opening 44d, drive wheel opening 44c and shroud 44b that covers the drive system 43f and suspension 43h. Sled cover 44 provides a rigid skin to protect and hide from view the underlying components of the sled while also providing a platform for the user's feet.

Figure 80:
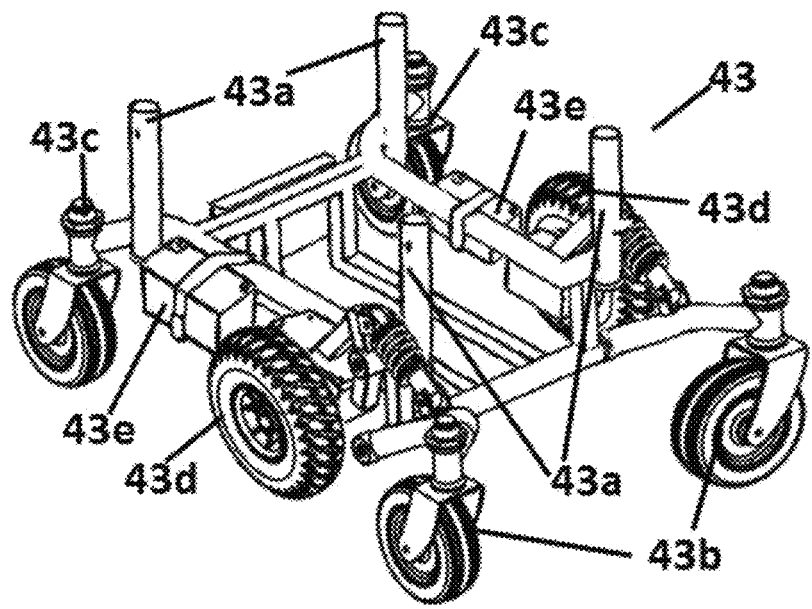
FIG. 80 shows an exemplary perspective view of powered sled with sled cover removed.

FIG. 80 shows the powered sled 43 with sled cover 44 removed to show internal major components, Powered sled 43 is constructed of mounting posts 43a, front wheels 43b, rear wheels 43c, drive wheels 43d, batteries 43e, drive system 43f, suspension 43h, and controller unit 43g. By operating both left and right drive wheels 43d in synch at equal revolutions per minute (RPM) and the same direction, devices 60 and 70 moves either forward or backward accordingly. Devices 60 and 70 can turn in a small radius when the drive wheels are operated in opposite directions simultaneously. A wider turn can be achieved by operating the right drive wheel 43d at a higher RPM than the left drive wheel 43d to turn left and vice versa for the other direction. Control for each drive wheel 43d speed and direction are provided from the joystick/LCD controller unit 17 in conjunction with controller unit 43g.

Figure 81:
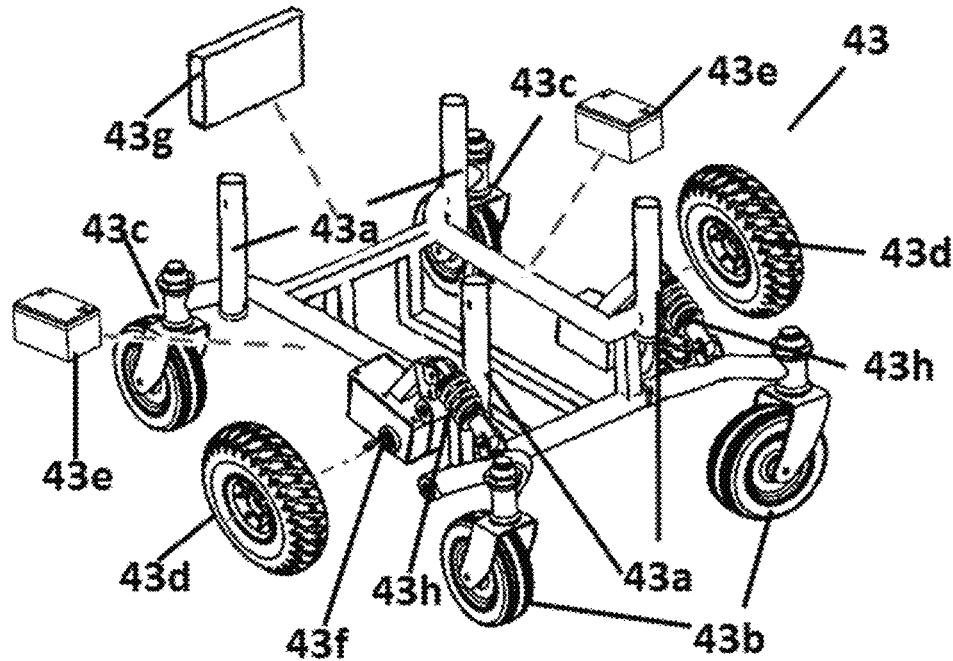
FIG. 81 shows an exemplary exploded view of powered sled with sled cover removed.

FIG. 81 shows the exploded view of the powered sled 43 with sled cover 44 removed to show more clearly the internal major components, Powered sled 43 is constructed of mounting posts 43a, front wheels 43b, rear wheels 43c, drive wheels 43d, batteries 43e, drive system 43f, suspension 43h, and controller unit 43g.

In more detail, still referring to the preferred embodiment of FIGS. 1-81, the mobility assistance devices 10, 10M, 20, 20A, 30, 40, 50, 60 and 70 transfer body weight from the legs to the "sit bones" or otherwise more broadly distributed across the pelvis either through a walking seat with belt or a harness. When is use, the individual's legs are used to move the device (for self-propelled embodiments) rather than fully supporting the individual's weight. Several positions are possible from a full standing posture with the legs essentially vertical (in this case, the individual's heels may even be off the ground and movement driven using the "ball" or front portions of the feet), to partially standing posture with the legs positioned forward of the body (thighs not fully vertical, entire foot may be engaged).

Figure 82:
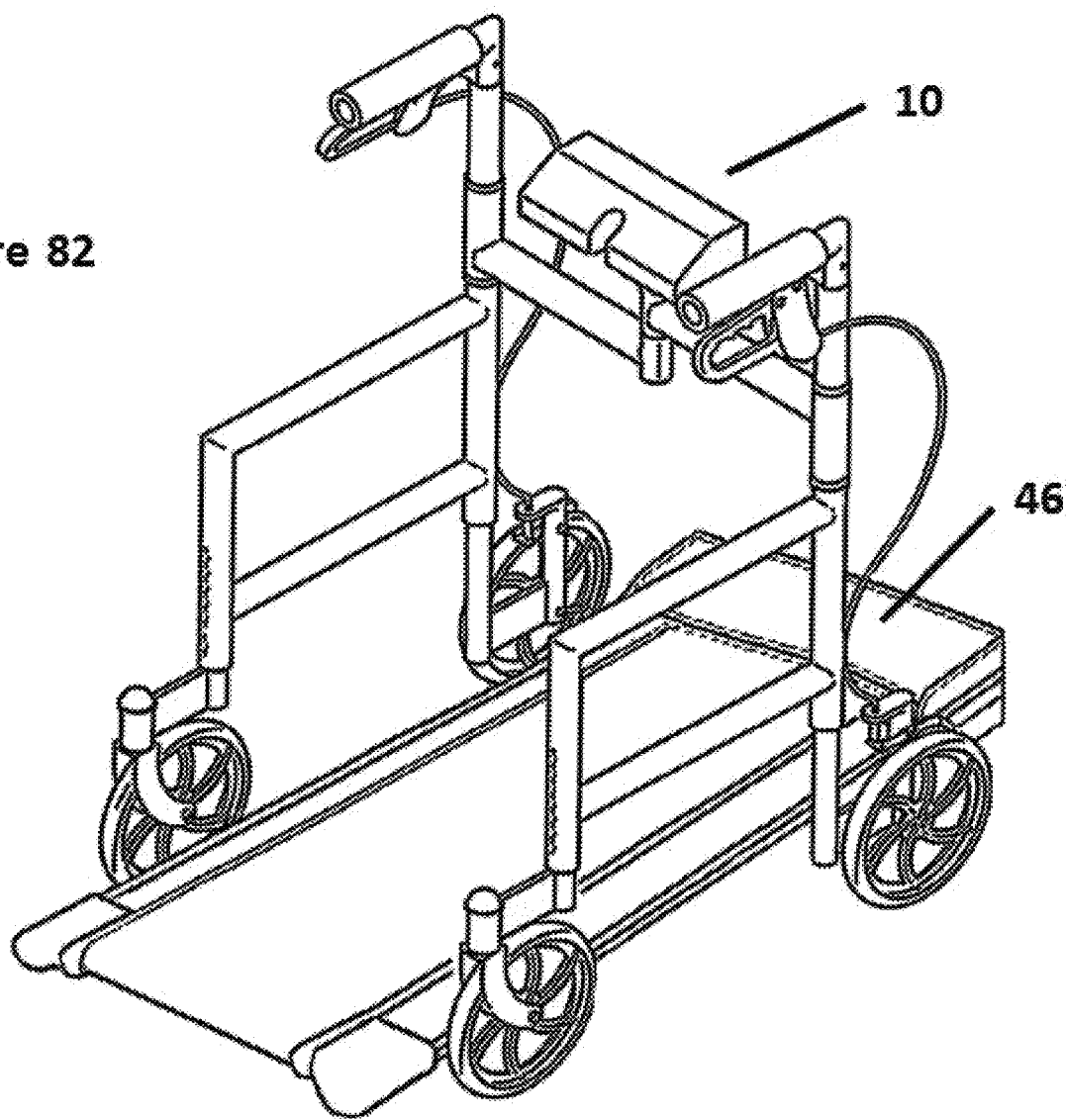
FIG. 82 shows an exemplary use of the walker with a treadmill for rehabilitation purposes.

FIG. 82 shows an exemplary use of the device 10 with a treadmill 46 for rehabilitation purposes. In this embodiment, a low profile slim treadmill 46 is positioned below the device 10 and below the walking seat. The treadmill 46 together with the device 10 allows the disabled user to perform walking or running aerobic-type exercise while the user remains in a relatively stationary position so that long periods of walking exercise can be done, despite the user's leg disabilities or balance problems. Device 10 coupled with the treadmill 46 provide a significant health benefit to those who otherwise may not be able to exercise their legs and achieve a full cardio-vascular workout. This embodiment with the treadmill 46 allows the user to exercise in a confined space that would otherwise require a large area. The treadmill 46 generally has a base that the disabled patient can walk on, a pair of parallel, spaced rollers journalled in the base, and belt carried by the rollers. A suitable motor powers one of the rollers, thereby moving the belt with the rollers. A moving upper surface of the belt provides a running/walking surface. A forward post extends up from the base for supporting a control panel, which typically has controls for turning the treadmill on and off and for varying the speed of the belt. The control panel often has indicators for selectively displaying operational information such as speed, distance traveled, and time. The user may press a suitable button on the control panel to toggle between two or more different displays.

FIG. 83 shows an exemplary treatment process using the above devices. The process starts by positioning first and second frames on left and right sides of the users with a hinge arm mechanism coupled to the first and second frames including a walking seat positioned on the hinge arm mechanism to receive the person (102). Next, the patient is instructed to comfortably position their sit-bones on the walking seat and then to secure the user with the belt, adjusted firmly but comfortably, to the walking seat (104). The patient then walks while contacting the walking seat for support, wherein the walking seat provides clearance for legs walking in a forward and backward motion (106). The patient gradually transitions in position from a mostly seated posture to a fully or nearly fully standing posture over the course of therapy (108). This treatment continues until the user assumes as vertical a standing posture as deemed appropriate by the directing health professional. If the user is done with the therapy and no longer requires the device (such as for a surgically repaired knee, for example) the user can resume walking without the device. If the user will continue to require the device to enable walking for the indefinite future (such as for a permanent leg disability, for example), the device will remain more or less at this setting going forward.

Figure 84:
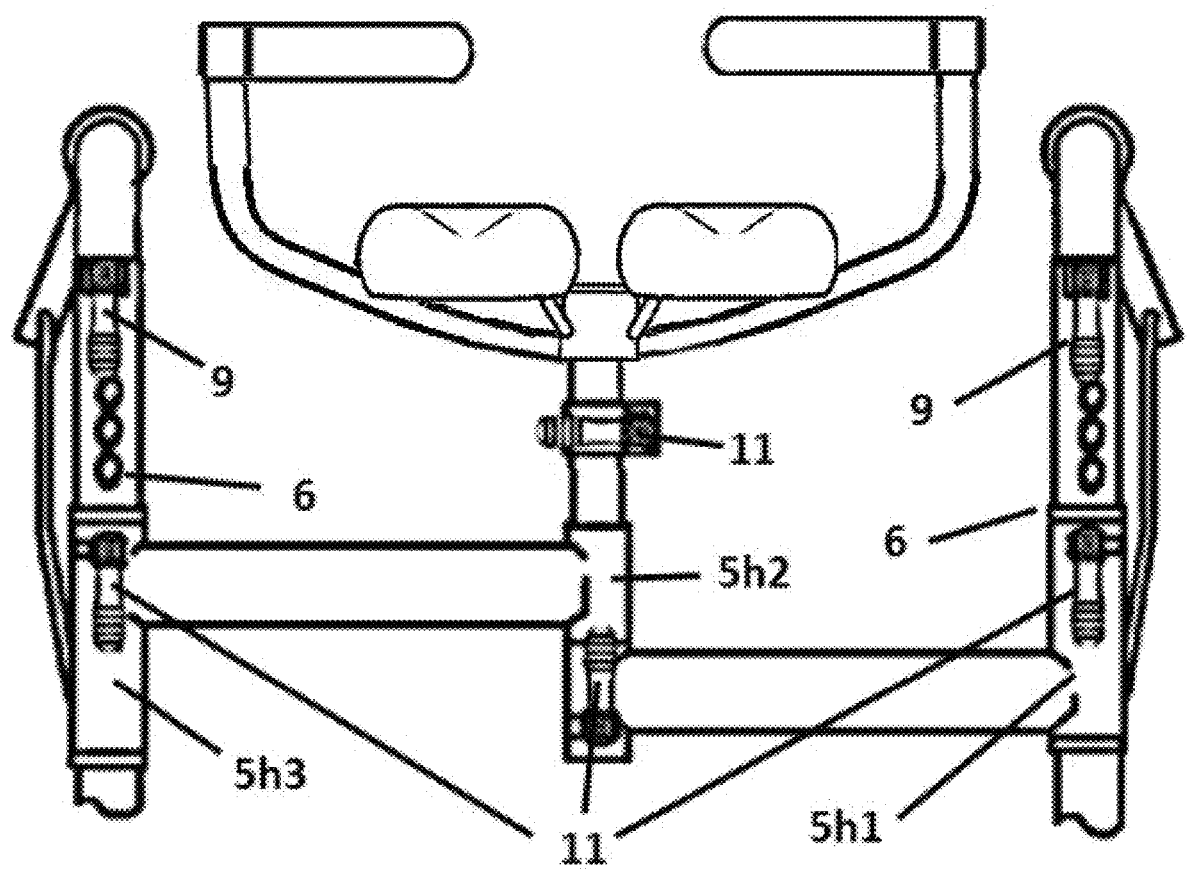
FIGS. 84-86 show alternative designs that replace the belt with "swivel arms."
Figure 85:
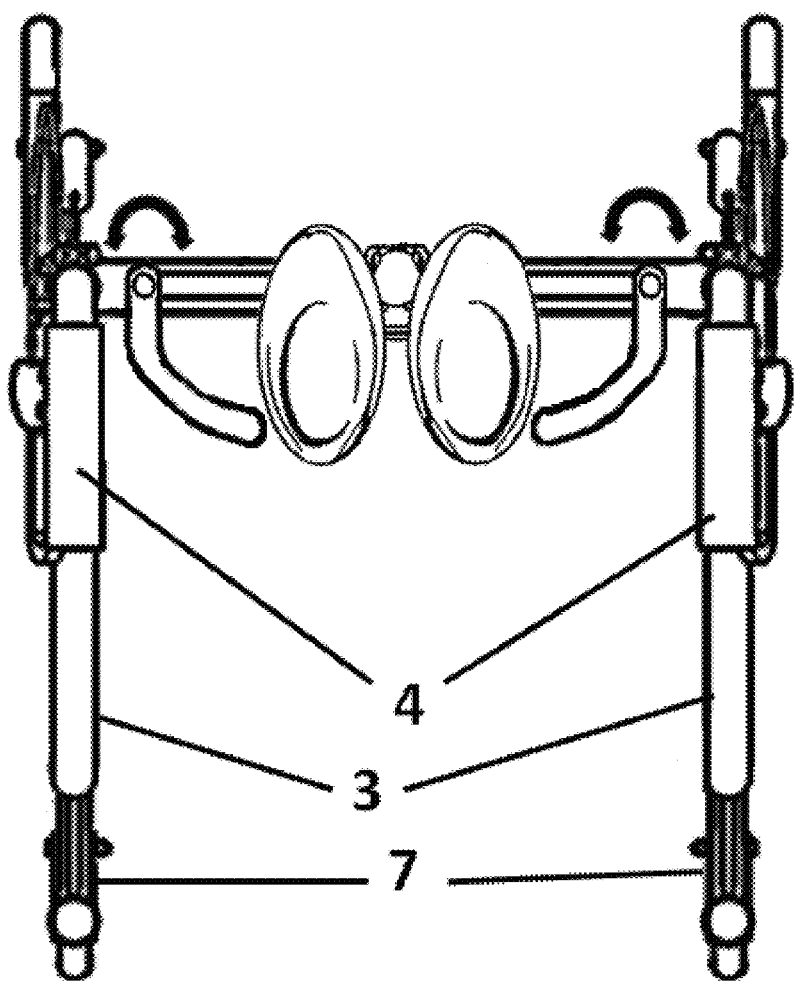
Figure 86:
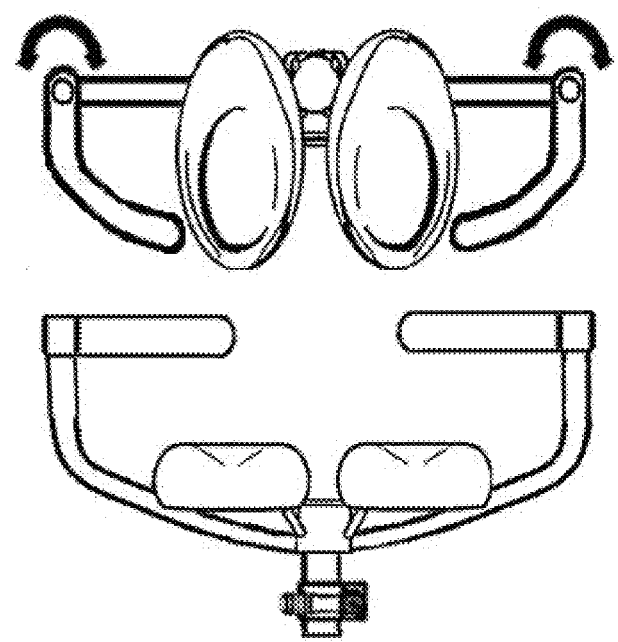

FIGS. 84-86 show alternative designs that replace the belt with "swivel arms" which pivot around, ratcheting as they go to provide the equivalent function of the belt to secure the user in place. When the user pushes the bottom on the top and the arms release outward and thereby release the user from the device.

The device frames can be used simply to help someone stand comfortably. The user may not be ready yet to walk around or may not want to use it for walking, but simply want to be supported when he or she stands. So, the user may use a version without wheels or just use it with wheels locked when he or she wants to stand more so s/he can reduce her time sitting. S/he does not intend to use it for walking.

Figure 87A:
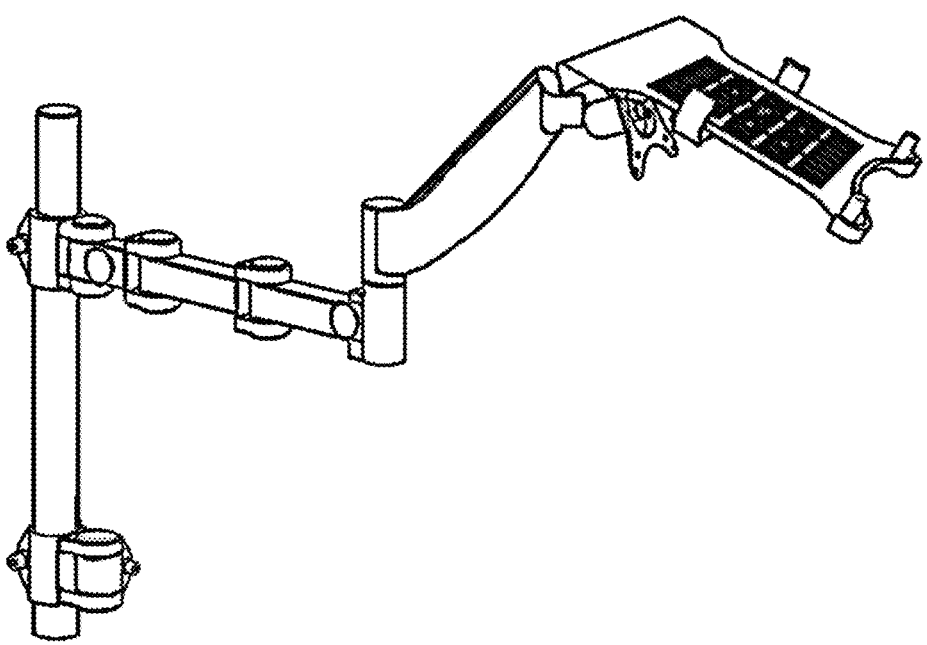
FIGS. 87A-87B show an exemplary swing arm attachment to allow a user to rest on the frames and use a computer, laptop, or tablet, among others.
Figure 87B:
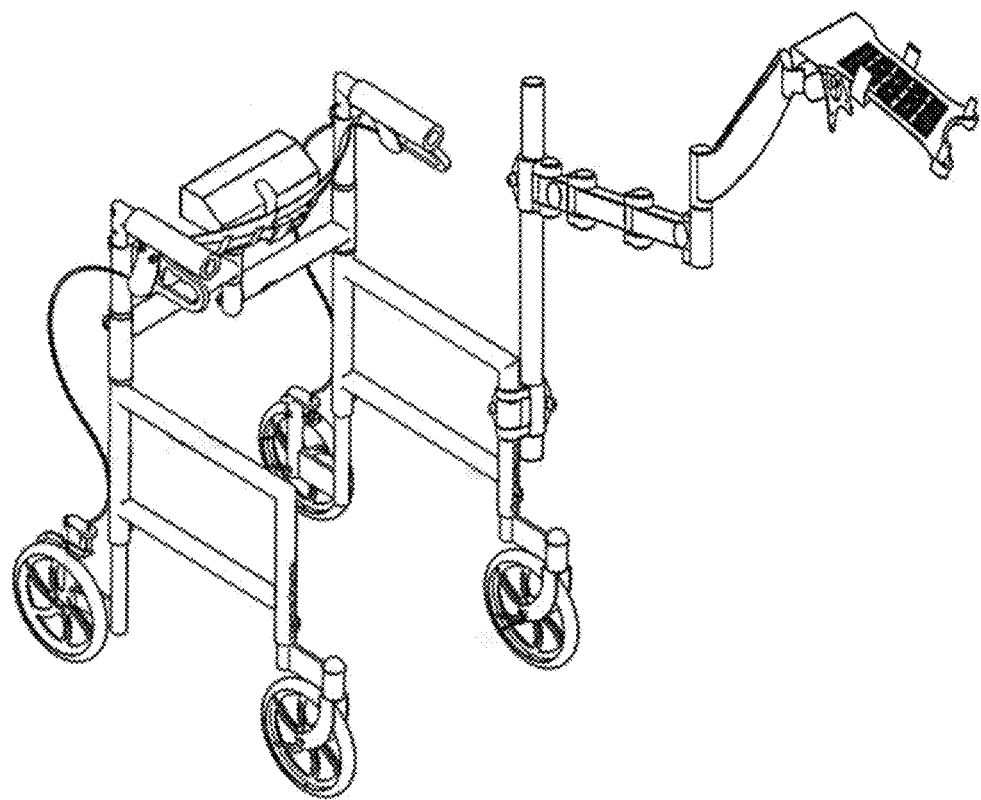

In other embodiments, the user can use the LifeGlider as support for working on computers without sitting on a chair. FIGS. 87A-87B show an exemplary swing arm attachment to allow a user to rest on the frames and use a computer, laptop, or tablet, among others. This is an attachment that enables the frames to position a tablet or a notebook PC in position for use. As shown, the attachment unit is mounted on the frames with the holder for the tablet or PC swiveled out for clarity. The articulated arm can swivel, raise, lower and otherwise be moved and secured into position at any number of heights, angles and position by the user. The system can be used as a stand-up desk and allows the user to stand and work effectively all day without fatigue. Office workers typically sit all day at their desks and such environment causes the workers to become less energetic as time goes by. With the system, the workers are partially active even as they work and thus they no longer get fatigued. In tests, at the end of the day, workers have as much energy and their legs feel as fresh as their morning conditions.

Figure 88A:
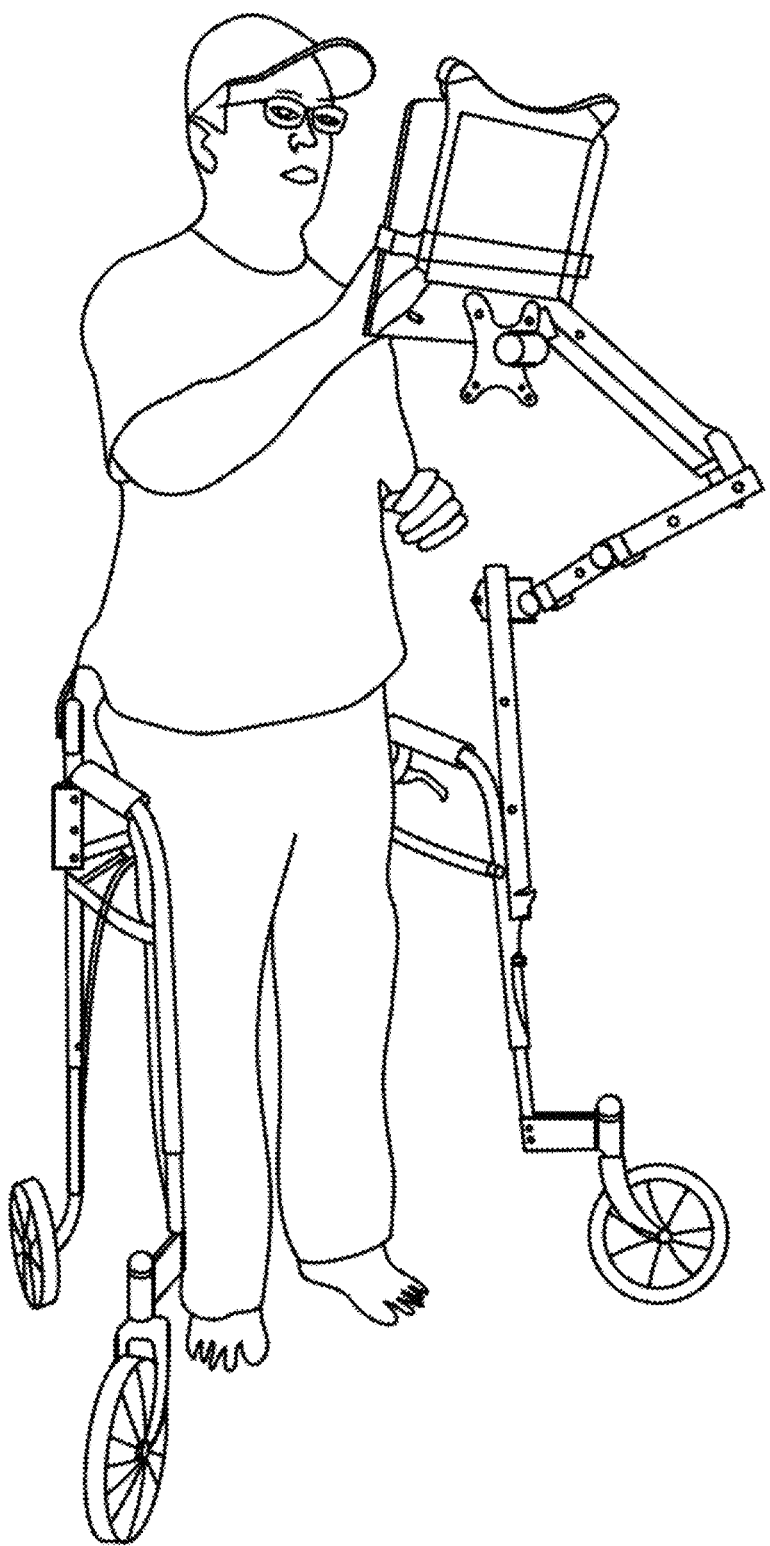
FIGS. 88A-88B show exemplary usage scenarios where the user is standing with the walking seat and the arm in an extended position for work and where the user is resting with the arm folded.
Figure 88B:
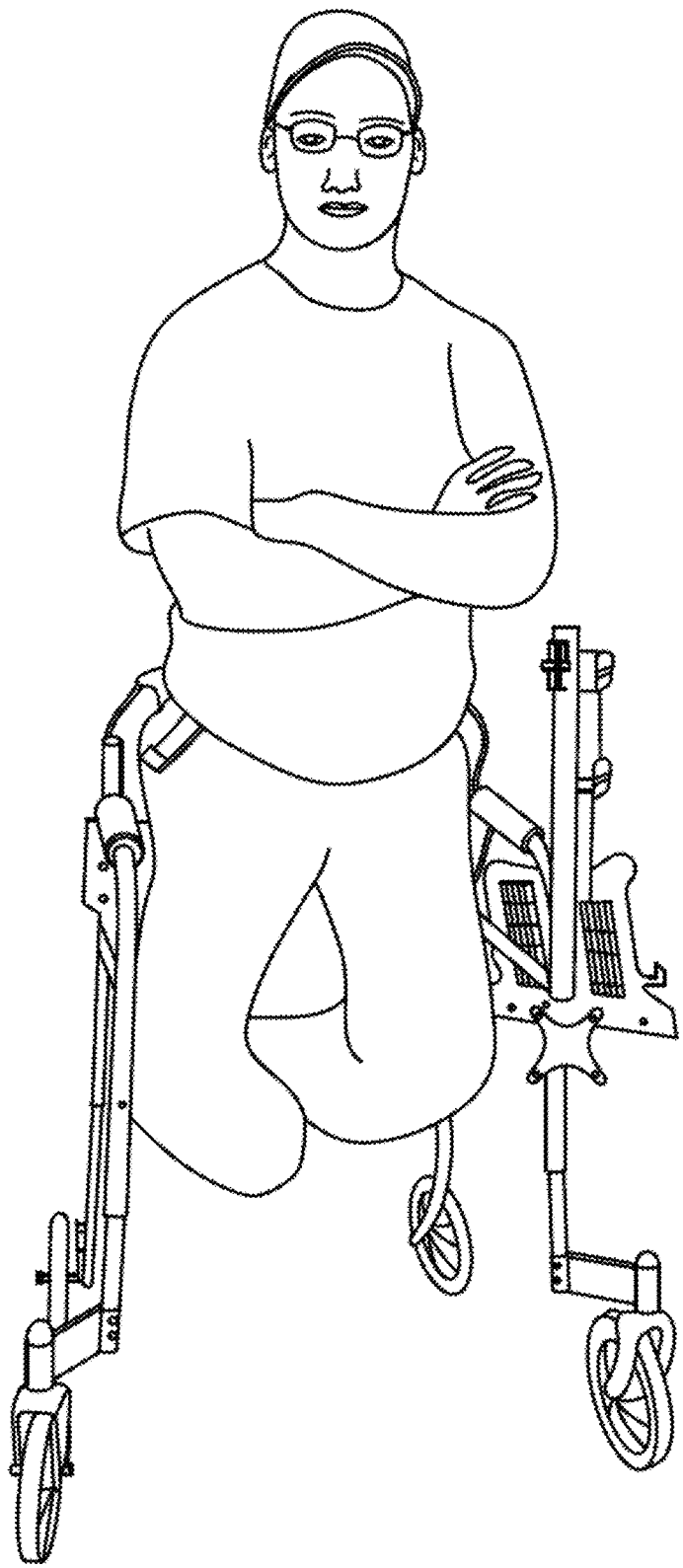

Turning now to FIG. 87A-87B, exemplary walking seats with Attachment Arm(s) are shown. Both mobility and furniture embodiments can be extended by attaching arms that allow a portable work environment. The use of these arms can support to the use of computers, tablets, smart phones, cameras and many other devices. They can also hold trays and tables for portable uses beyond electronics. These arms can hold other medical equipment such IV units, monitoring apparatus, oxygen supply systems and other apparatus as may be necessary in a hospital setting or other institutional or rehabilitation setting. These arms can allow people to remain standing while doing a variety of functions. This can be working, studying or walking and moving with medical equipment as part of a recovery program. These arms can also be adapted to enable carrying items both lightweight and heavy. This may be convenient for environments where user's need to transport items. Examples can be factory, warehouse, retail and delivery services employees, These arms can be conveniently folded and stowed and/or removed for times when not in use. FIGS. 88A-88B show exemplary usage scenarios where the user is standing with the walking seat and the arm in an extended position for work and where the user is resting with the arm folded.

Alternatives to the Belt are detailed next. The above discussions show exemplary means to secure the user's pelvis and center of gravity by means of a "walking seat" and an upper pelvis capture mechanism. The user's pelvis is secured by such a means as to allow the user to walk with proper gait and with proper posture. The foregoing a belt and buckle system for the upper pelvis capture mechanism that in conjunction with the walking seat to fully secure the user's pelvis and center of gravity.

Figure 89:
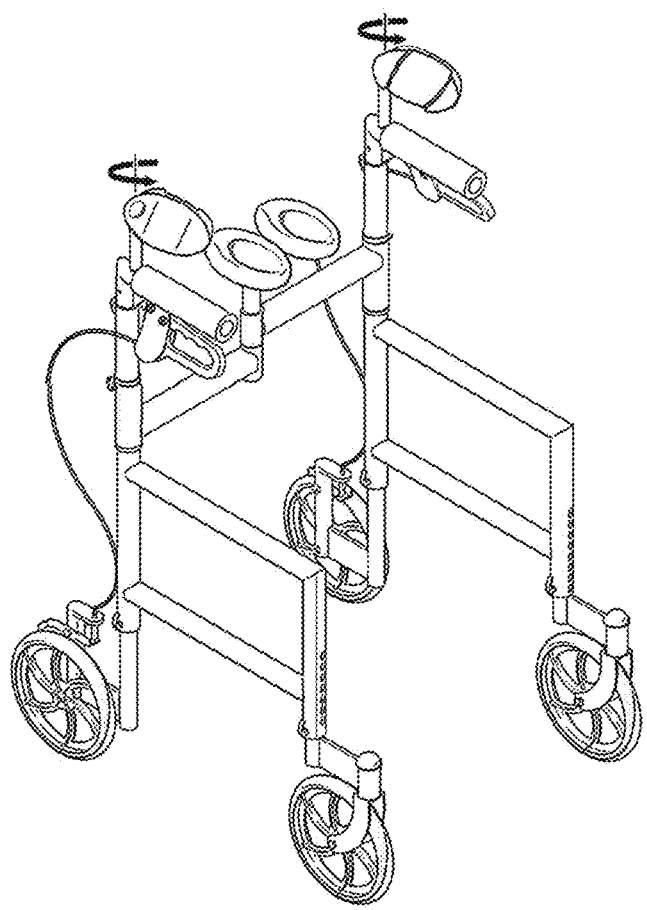
FIGS. 89-91 shows various alternatives to the belt that use the walking seat (and variations) as the by providing alternative upper pelvis capture mechanisms to the belt and buckle system.
Figure 90:
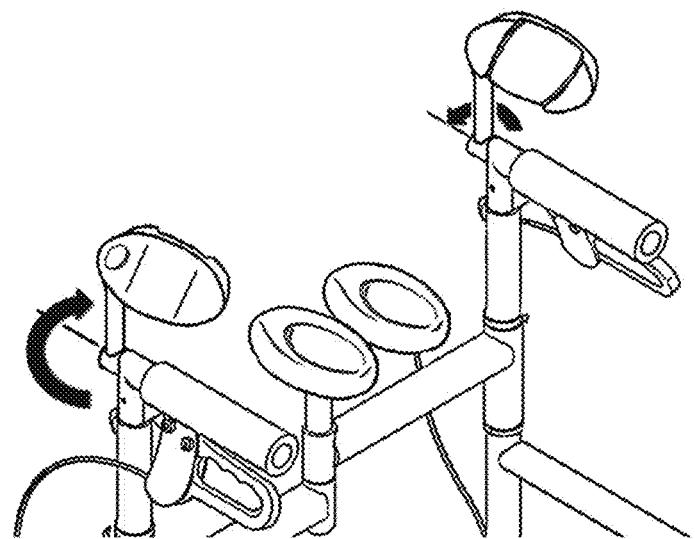
Figure 91:
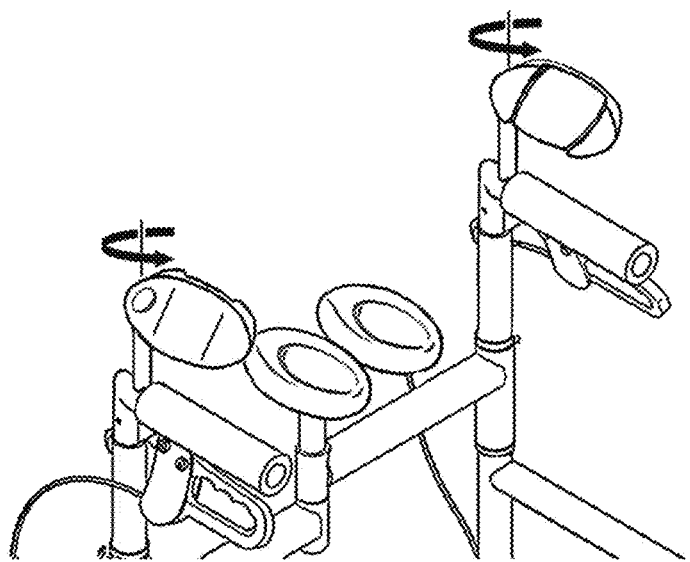

FIGS. 89-91 shows various alternatives to the belt that use the walking seat (and variations) as the by providing alternative upper pelvis capture mechanisms to the belt and buckle system.

FIG. 89 shows a "flip" arrangement that rotates around a vertical axis on each side of the user and captures the hip points or upper portion of the pelvis in a manner equivalent to the belt and buckle. The "flip" opens laterally to allow entry by the user and ratchets closed to form a firm hold on the user's hip points or upper boney structure of the pelvis. The "flip" is released, allowing exit by the user by a push button, a lever or other mechanism to open the "flip." Activation of the "flip" can be through either manual or motorized means.

FIG. 90 shows a "grasp" arrangement that rotates around a horizontal axis on each side of the user and captures the hip points or upper portion of the pelvis in a manner equivalent to the belt and buckle. The "grasp" opens laterally to allow entry by the user and ratchets closed to form a firm hold on the user's hip points or upper boney structure of the pelvis. The "grasp" is released, allowing exit by the user by a push button, a lever or other mechanism to open the "grasp." Activation of the "grasp" can be through either manual or motorized means.

Figure 92:
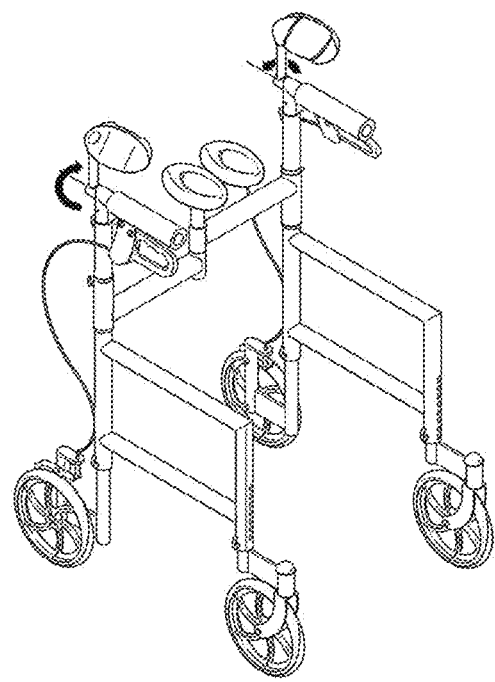
Figure 93:
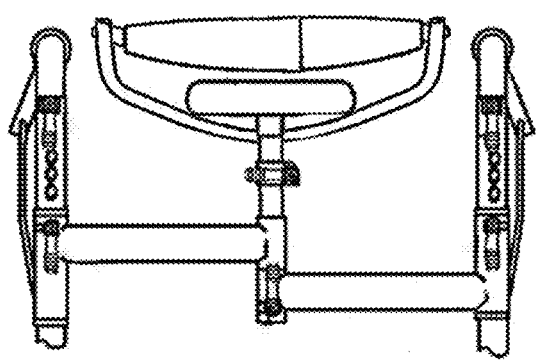
FIGS. 93-96 show various exemplary Upper Pelvis Capture integrated into the Walking Seat assembly.
Figure 94:
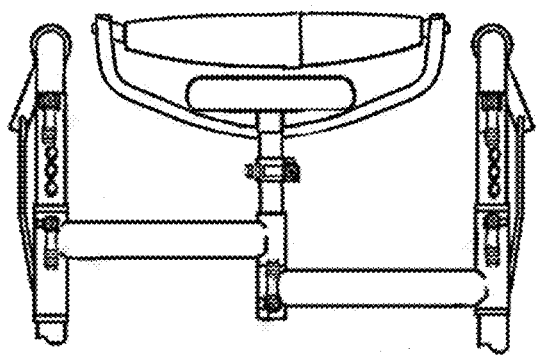
Figure 95:
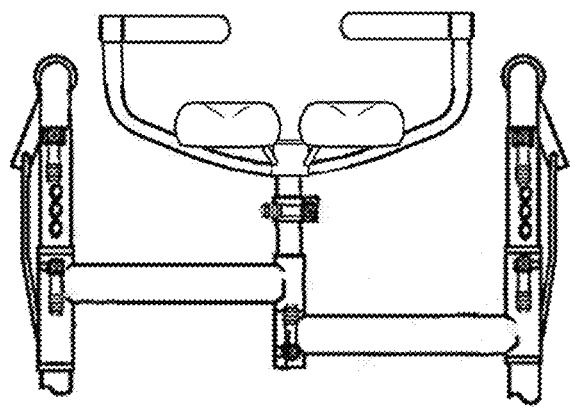

FIGS. 91-92 show a "capture arm" arrangement that is a combination of the "flip" and "grasp" that rotates around both vertical and horizontal axes on each side of the user and captures the hip points or upper portion of the pelvis in a manner equivalent to the belt and buckle. The "capture arm" opens laterally to allow entry by the user and ratchets closed to form a firm hold on the user's hip points or upper boney structure of the pelvis. The "capture arm" is released, allowing exit by the user by a push button, a lever or other mechanism to open the "capture arm." Activation of the "capture arm" can be through either manual or motorized means.

FIGS. 93-96 show various exemplary Upper Pelvis Capture integrated into the Walking Seat assembly. While the above discussion illustrates how to secure the user's pelvis and center of gravity by means of a "walking seat" and an upper pelvis capture mechanism. The user's pelvis is secured by such a means as to allow the user to walk with proper gait and with proper posture. In contrast to a belt and buckle system connected to side frames that in conjunction with the walking seat secures the user's pelvis, the system of FIGS. 93-96 uses the same walking seat (and variations) as the original patent but innovates further by integrates the pelvis capture means into the walking seat assembly directly. These embodiments enable the pelvis capture innovation to go beyond mobility. It frees the primary innovation of capturing the user's pelvis from the mobility device and makes it available to many other use cases where a comfortable alternative to sitting is desirable.

Figure 96:
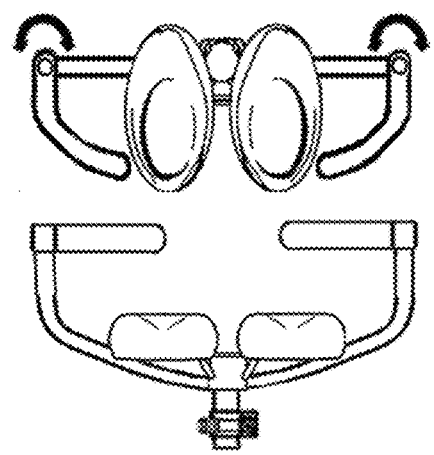

From furniture, to comfortable means to stand for any and all situations as an alternative to sitting. Some examples include office, school, factory floor, transportation, entertainment, and retail to name a few. These embodiments work for any and all applications where it may be more desirable to stand than sit. These embodiments are also applicable for situations where individuals predominantly stand and could benefit from reduced fatigue of the legs by having weight bearing fully or partially removed from the legs. Some examples in retail clerks, law enforcement officers, warehouse and factory workers, teachers, doctors, dentists and many others. FIG. 96 shows an isolated view of the upper pelvis capture arrangement integrated into a walking seat assembly.

Figure 97:
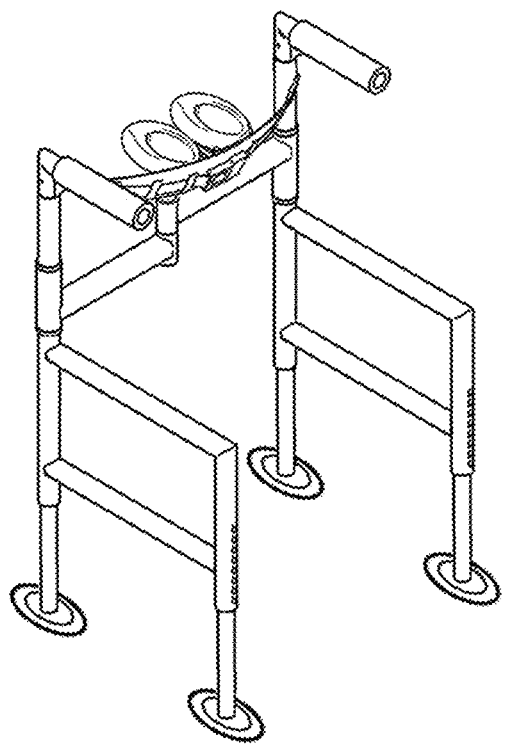
FIG. 97 shows an exemplary support device for Standing without Wheels.

FIG. 97 shows an exemplary support device for Standing (No Wheels). The above discussion shows the means to secure the user's pelvis and center of gravity by means of a "walking seat" and an upper pelvis capture mechanism. While the combination of "walking seat" and an upper pelvis capture mechanism combination enables walking, it also supports standing in the body's optimal position where it works most efficiently and effectively. The user's pelvis is secured by such a means as to allow the user to stand with proper posture while allowing all of the body's functions to work better. Standing in the position provided by this means allows improved circulation, improved respiration, improved digestion, and other body functions. When the body operates more efficiently, it can heal faster and operate better. In the embodiment of FIG. 97, the wheels are replaced by legs with base pads or any other suitable floor contacting surfaces to secure the support device to the floor for standing purposes. The standing versions can be considered furniture since its utility is no longer geared towards mobility purposes.

Figure 98A:
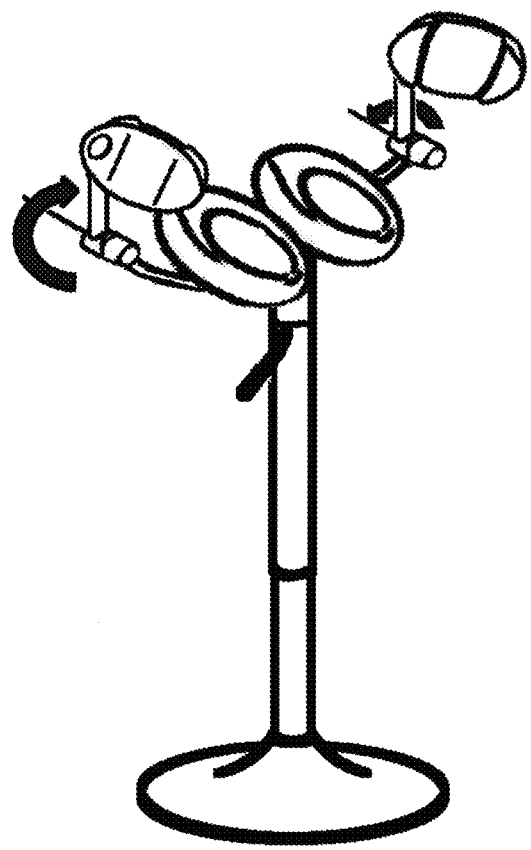
FIG. 98A-98C show another embodiment for Rehabilitation Use (No Wheels).
Figure 98B:
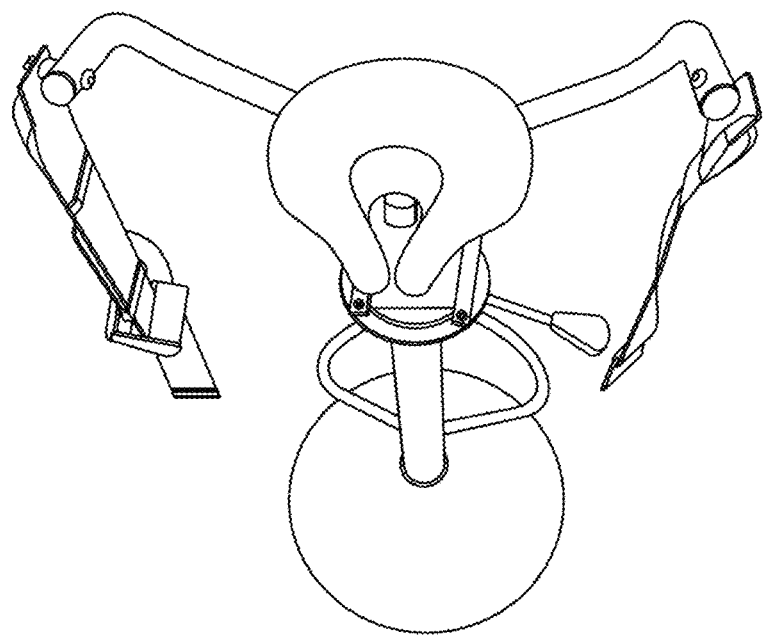
Figure 98C:

FIG. 98A-98C show another embodiment for Rehabilitation Use (No Wheels). FIG. 98A shows the "grasp" mechanism with allow ratcheting with a push button release. The embodiment grasps onto the user's hip in place of a belt. FIG. 98B shows a version with belts in place of the grasps, and FIG. 98C shows a user on the walking seat secured by the belt. The "walking seat" and upper pelvis capture mechanism combination enables walking not only while using the device on wheels but also while using the device without wheels and walking using a treadmill. The walking seat and upper pelvis capture combination as described in the previous disclosures has been found to position the user's body in its optimal position where it works most efficiently and effectively. By stabilizing the pelvis and center of gravity, the embodiment enables an ideal position for rehabilitation as a part of a treadmill. The system allows wheel free walker to be used for rehabilitation, including use with a treadmill. Because the user's body is operating optimally and held in the proper postural position while exercising (such as on a treadmill) enabled by the innovation, even severally debilitated individuals can be retrained for a proper gait, regain endurance and rapidly improve in capability. So the new disclosure is for the stationary use of the technology for rehabilitation activities such as walking on a treadmill. FIGS. 98B-100C show another exemplary furniture embodiment that supports the user. The "walking seat" and upper pelvis capture mechanism combination has been found to place the user's body in the optimal standing posture, ideal for furniture applications where individuals desire a comfortable alternative to sitting. Because the user's body is operating optimally and held in the proper postural position while in this new class of furniture enabled by the innovation, there is the opportunity to provide broad benefits to everyone who desires to stand comfortably for extended periods and avoid excess sitting. Standing in the position provided by this means allows improved circulation, improved respiration, improved digestion, and other body functions. When the body operates more efficiently, it can operate better. Excess sitting has been compared to smoking for its negative impacts on health and " . . . increases the risk for developing dozens of chronic diseases from cancer and diabetes to cardiovascular disease and non-alcoholic fatty liver disease. The furniture embodiment of FIGS. 100A-100C can be use in applications where chairs and other devices for sitting are currently used. This application allows all members of the general population to benefit by avoiding excess sitting and the long-term adverse health effects of sitting too much.

Figure 99:
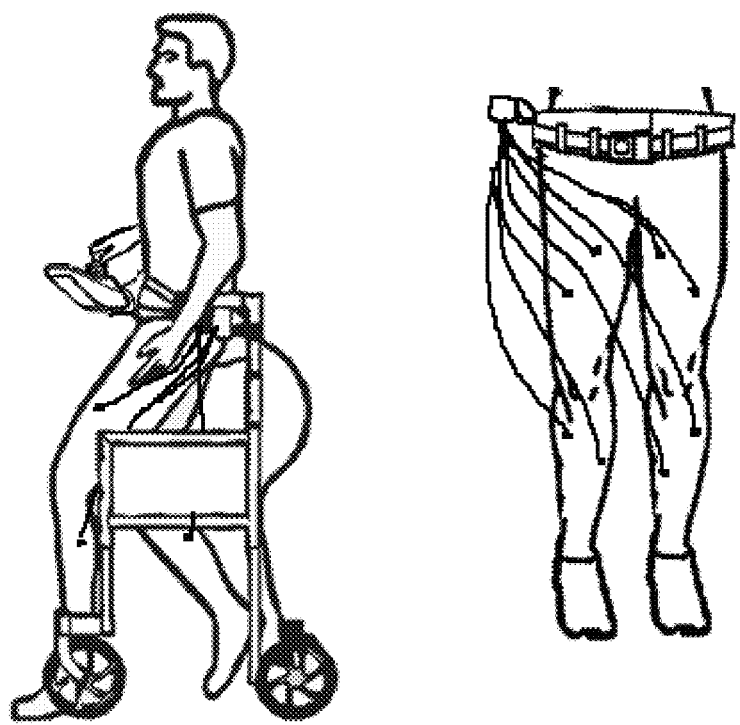
FIG. 99 shows an exemplary walking device with Functional Electrical Stimulation (FES).

FIG. 99 shows an exemplary walking device with Functional Electrical Stimulation (FES). A joystick or a smartphone can be used to control the wheels of a powered version of the walking device. The embodiment of FIG. 99 uses FES to control and drive the legs of paraplegic or other individual who has difficulty directly moving the legs themselves. So, instead of driving wheels, the joystick or smartphone application is connected either through wires or wireless means to electrodes that make the leg muscles operate in the proper sequence to walk, stand, and otherwise move about. The "walking seat" and upper pelvis capture mechanism combination can place the user's body in the optimal standing posture and to enable proper gait while securing the user's center of gravity. While the walking device maintains the center of gravity, maintain balance, enable proper gait and proper posture, the FES electronics with wireless or wired electrodes can sequentially stimulate the muscles to enable walking. A joy stick or a smartphone application can provide control for the direction and speed of walking. Instead of driving the wheels, the FES embodiment helps the leg muscles to move and drive the walking device forward.

Embodiments provide a control system for a FES system that is capable of providing safe and effective stimulation of muscles which may be described as reliant on a combination of applied stimulation and passive stimulation. With the walker, the system can provide near isokinetic training which may be applied using a set of rules-based programs of exercise therapy that recommend certain programs for certain patients. In various embodiments, the FES module applies slow velocity isokinetic exercise (e.g. FES-induced cycling at 5-25 rev.min-1) to build muscle strength and bulk, medium velocity isokinetic exercise (e.g. FES-induced cycling at 25-40 rev.min-1) to promote leg muscle fatigue-resistance, and fast velocity isokinetic exercise (e.g. FES-induced cycling at 40-60 rev.min−1) to promote enhanced cardiorespiratory fitness.

The FES can be used in a motor-less walker or a motorized walker in which there is combined the use of a motor driven exercise machine with the user connected to an FES system via electrodes for activating selected muscle groups corresponding to those to be used on the walker. In at least a preferred embodiment, a control system is deployed that receives signals via closed loop feedback, indicative of the user's performance during exercise, and the system controls the FES pulses to the user to maintain a substantially isokinetic exercise regime whereby average power output and/or average torque is the controlled outcome. The controlling of the FES signals, advantageously, can be by manipulating current amplitude and timing and obtaining biofeedback to assist the user to perform exercise. The FES system can elicit muscle contractions for a paretic or paraplegic user, but in the alternative, the system can be applied to those with impaired or normal voluntary muscle activation wherein the FES system simply assists such muscle contractions via sensory biofeedback.

One FES embodiment provides a method of operation and a control system that establishes substantially isokinetic FES-induced exercising. This approach is believed to provide a significantly enhanced therapeutic effect compared with conventional exercise regimes. In one embodiment, the FES unit and the walker maintain a constant speed, for example a particular distance over a predetermined interval of exercise such as 30 minutes. When muscle power is generated in excess of that required to move the legs, the adaptive control loop operates to adjust both current to the motor to maintain constant velocity and regulate FES pulses to the legs to maintain constant average power output. By simultaneously controlling both the motor and the stimulation pulses, the system can maintain both constant velocity and constant power/torque output regardless of whether the user can provide voluntary contractions in addition to those generated by electrical stimulation (i.e. FES). In other implementations, the FES and walker control an exercise regime to permit muscles to perform a lengthy exercise session by arranging for relatively low speed initially with subsequent exercise at higher speed to materially avoid premature fatiguing, thereby permitting more effective muscle training over an extended period. The system can be applied in exercise regimes to recognise that different types of therapy can be achieved at different velocities of limb movements. For example, training at a relatively high speed will promote cardiorespiratory training, whereas slower speeds enhance the development of muscular strength. This speed-relative training can be applied to forms of therapy that utilise FES-induced muscle contractions, or therapies that employ voluntary muscle contractions by users.

In one aspect, the invention may be defined as consisting of an apparatus comprising a motor-driven walker machine, a functional electrical stimulation (FES) system for delivering stimulation to corresponding muscles of the user, and a control system to monitor the power applied to the electrical drive system of the motor as well as to control the timing, nature and duration of the FES pulses. The motor and FES control system act in response to measured performance, whereby the pedalling velocity is maintained at a user-specified substantially isokinetic rate while the muscles are simultaneously kept operating at a constant average power/torque output.

In one embodiment, there is provided an apparatus which includes a motor-driven exercise machine, an FES system for providing skin/muscle sensory biofeedback over corresponding muscles of a non-paralysed user and a feedback control system monitoring the power/torque applied to the electrical drive system of the motor to control the timing, nature and duration of the low current amplitude FES pulses in response to measured performance output by the user on the machine, whereby the speed of operation of the exercise machine can be pre-set to a desired constant velocity and substantially isokinetic FES exercise is thereby achieved. For paralyzed users; in this case, the system may be defined as consisting in an apparatus including a motor-driven walking machine, an FES system for the activation of corresponding muscles of a paralysed user, and a feedback control system monitoring the power/torque applied to the electrical drive system of the motor to control the timing, nature and duration of the FES pulses in response to measured performance output by the user on the machine, whereby the speed of operation of the exercise machine can be pre-set to a desired constant velocity and substantially isokinetic FES exercise is thereby achieved. In one embodiment, a system provides Progressive Resistance Isokinetic Training (PRIT) with the walker. PRIT allows training individuals with neuromuscular disabilities such as spinal cord injury, hemiplegic stroke or traumatic brain injury in a new and valuable way using FES. FES induces leg muscle contractions, during constant-velocity leg movement with the walker, under control of a computer with purpose built software to achieve substantially isokinetic exercise.

The portable mobility assistance device allows individuals to move about in a standing or partially standing posture supported in a manner that can significantly reduce the stresses and discomfort on ankle, knee, hip, wrist, elbow and shoulder joints or at the interface with a prosthetic leg. The device potentially reduces or eliminates the dependency on a wheelchair for mobility. Because of its compact size, maneuverability, and the standing or partially standing posture of the user, the device can potentially enable the user to avoid costly renovations to house and office that would otherwise be necessary if the user was wheelchair bound. The device allows the arms of the individual to be more available to use for other purposes while in use. The preferred embodiment also provides stable support while traversing wheelchair accessible walkways, ramps, paths, rooms and other indoor and outdoor facilities as well as (when appropriately outfitted) over a variety of other terrain. Additionally, the device is foldable into a compact form and capable of being conveniently transported such as in an automobile trunk or as a checked item for an airplane. The system supports a disabled or elderly person during ambulation so that he or she can walk or exercise while minimizing risks of falls or injuries related thereto. The mobility device reduces the user reliance on the wheelchair. By encouraging the user to walk with aided support by the system, the system reduces causes of skin sores. The system encourages active walking with attendant increased blood flow. Pressure on the buttock is reduced, and blood circulation is enhanced to minimize pressure or skin sores. The device minimizes skin sores as it eliminates prolonged pressure and wetness on the skin.

The walking assistance device has many other benefits. For example, the proportion of weight supported by the device can be variable. For example, individuals may prefer the device to support about 50% of their weight and therefore adjust the height to posture themselves accordingly in the device. It is totally up to the user and their managing health practitioner to decide what portion of the weight to remove from the legs. This distribution can be varied by the individual by the height adjustment prior to use as well as posture during device use.

The wheel assemblies 7 and 8 allow natural fluid transfer of the device forward, backward and turning motions with minimal force driven through the individual's legs and without the necessity of using the arms. The belt 2 and harness 23 use buckles similar to those used in automotive or aircraft seat belts (of the non-retractable type). This allows the individuals to get secured into and out of the device quickly and to make adjustments easily. Because walking seat 1 with belt 2 and harness 23 are load-bearing, comfort is very important. Walking seat 1 employs cushioning and other features similar to those on bicycle seats for comfort and freedom of leg movement. The preferred embodiment figures show a truncated walking seat front to free legs for easy and full movement and a cut-away for long-term comfort by avoiding excess pressure on the tailbone, but any number of alternative walking seat designs is possible. Harness 23, is designed to cushion and distribute the individuals weight for extended time use. The harness 23 can combine features of a bungee trampoline harnesses and rock and mountain climbing harnesses.

Users of the device are able to relax and use a resting sling seat 13 when not needing or wanting to be moving. Seat 13 allows the individual to be in a stationary and seated position (thighs positioned approximately horizontally, feet comfortably on the ground).

Powered sled assembly 43 and controller unit 43*g* are of a similar design to analogous components of a battery operated wheelchair. This includes standard rechargeable batteries, drive motors and circuit boards, joystick controller, and other components commonly found in battery operated wheelchairs. The power drive wheels 43*d* are attached to independently controlled and operate gearboxes that allow differential speeds and can also operate in opposite directions (to turn around in a tight radius). While the frame and sled cover 44 of the power sled assembly 43 are unique to the devices 60 and 70, the other components are purchased and are also used in other devices.

The construction details of the preferred embodiment, as shown in FIG. 1 through FIG. 81, include structural tube members welded, fused, pinned or otherwise fastened securely in place. These materials can optionally be metals (such as aluminum, steel, titanium or another alloy, for example), lightweight composite material (such as graphite, fiber glass or carbon fiber, as examples), reinforced resin (structural "plastic" for example), or a combination thereof. The ideal construction will be of lightweight materials which are still very structurally strong and rigid, however, as with other devices, there is generally a trade off between weight and costs which is a major consideration in the choice of materials.

In one embodiment, an overall approximate size of the mobility assistance device 10 is approximately 21 inches wide by 25 inches deep by 32-42 inches (adjustable) tall. Mobility assistance device 20 is approximately 21 inches wide by 25 inches deep by 32-42 inches (adjustable) tall. These can be scaled up or down to accommodate larger of smaller individuals.

The wheels can be constructed of metal or structural plastic and include rubber tires (of pneumatic, solid or other construction) and be sized according to intended use (smaller wheels, such as 4 inch diameter, may be suitable for indoor use while larger wheels, such as 8 inch or larger more appropriate for outdoor use).

The harness 23, belt 2, sling seat 13 and latching straps 25 would be constructed primarily of lightweight and strong fabric such as nylon or the like and could incorporate cushioning, wire, cable, rubber or plastic components to provide shape, strength, comfort or adjustability.

The mobility assistance devices 10 through 70 are sized to comfortably accommodate full grown adults including those of above average height and above average weight. The adjustability for height allows a common design to accommodate significant variation from below average to above average height in the user base. Adjustability for height can be up to +/−4 or more from a nominal device height.

The harness 23 can accommodate waist sizes from approximately 28 inches through 42 inches, or larger (more comfort can be derived by providing a greater range of sizes). Harness 23 and walking seat 1 may be further modified to accommodate more comfortably the anatomical differences between men and women.

Because the wheel assemblies 7 and 8 are relatively distant from the center of gravity of the device (approximately 12-15 inches), the device is very stable and not prone to tipping even when the operated on the incline of a conforming wheelchair accessible ramp.

The preferred embodiment allows the person transporting the device to optionally use the wheels to roll the device rather than carry it.

The wheels may be of a different characteristic for those individuals who would like to use the device outdoors as compared to those individuals who would predominantly use it indoors.

Variations of the device would include various options for brakes, suspension systems (to reduce jolts from mismatch pavement and other bumps), as well as other options that would add to the convenience and comfort of the individual (such as baskets, bottle or cup holders, mobile phone/device stand, umbrella holder, etc.). These variations are not shown in the figures, but are envisioned for the device. For example, in some embodiments of the mobility assistance device 10, a pocket assembly is provided on the inner surface of one of the frames 3. The pocket assembly includes an elongated first pocket attachment strip which is secured to the frame 3 according to the knowledge of those skilled in the art, such as using an adhesive, for example. An elongated second pocket attachment strip can be attached to the first pocket attachment strip. In some embodiments, the second pocket attachment strip is detachably attached to the first pocket attachment strip. One or more pockets can be provided on the second pocket attachment strip in adjacent relationship with respect to each other. Accordingly, various items (not illustrated) can be placed in the pocket or pockets when a user deploys the mobility assistance device 10.

There are other ways to connect the belt 2 to the side frames (3 for example) and other belt and buckle designs available. The one shown in the figures is one of the simpler configurations. As an alternative for attaching the harness 23 through latching straps 25, cables, rope, webbing or a simple direct latch to the structural through other means are available to equivalently perform this connection.

There are other ways of orienting the side frames. They could equivalently be positioned in front and behind the user and the user enters the device laterally. The hinge arm mechanism could be made of multiple arms connecting between the frames. The hinge arm could be located in front of the user rather than behind the user as portrayed in the figures.

There are other configurations possible connect the sling seat 13 to the side frames. There are multiple ways to accomplish the height adjustability. There are various configurations of walking seat 1 possible, similar to the range of variations available for bicycle seats. There are many possible forms of seat 13, including: rigid and semi-rigid seats, seats that are attached to the hinge arm members instead of the side frames, and rigid seats that fold out of the way, etc. There are other ways to securely fasten the walking seat. The one portrayed is one of the simplest and most common means available.

While the preferred embodiment 60 or 70 is depicted as a having battery operated sled 43 option, the power source could alternatively be delivered by an electrical cord connected to an electrical outlet, a solar cell, or an internal combustion engine, as examples. While portrayed in a sled configuration, alternative configurations could be open allowing the individual's feet to access to the ground.

Harness 23 could be composed of two or more separable subassemblies, one subassembly for supporting the individual under the sit bones and another means (such as belt 2) to hold the individual firmly in place. Additionally, variations of harness 23, include harnesses with any number of attachment loops or other means of connecting the harness to the structural members of the preferred embodiment. This could include using weight-bearing "pants" or "skirt" (not pictured), or pneumatic lift belt (not pictured) or other means that allow support of the pelvis and sit bones and transfer of body weight from the legs while still allowing relatively free movement of the legs.

There are alternative means for height adjustment such as the air spring used for seat height adjustment of many office chairs. The devices could incorporate shock absorbing features in wheel assemblies 7 or 8 to smooth out the feel over rough surfaces.

The advantages of the preferred embodiment include, without limitation, allowing the individual to move about in a standing or partially standing posture for an extended period of time while supporting their body weight using a harness or walking seat and belt. This reduces pain and discomfort on associated joints or from a prosthetic interface. Additionally, many individuals simply would prefer to move about in a more erect standing posture rather than to be seated in a wheelchair or scooter.

Additionally the device is designed to support a complete rehabilitation cycle, from the first days of treatment when a user is very limited in use of a leg or joint and getting acclimated to moving with the incapacity to the final and full recover of the affected function.

A significant benefit of the preferred embodiment is, because the device does not rely on the arms or shoulders to bear weight or maneuver the device, the individual has more freedom of movement and use of their arms for other purposes. The individual is able to walk and maneuver the device while keeping the hands generally free for other uses. This potentially allows individuals to more actively participate in many common activities otherwise only achieved with significantly greater difficulty without the preferred embodiment. By standing supported through the pelvis capture means, the body is in its optimal posture for operation of all basic functions including respiratory, circulatory, digestive and other systems and because the weight is relieved from the legs, users do not get fatigued nearly so quickly.

Isolating the pelvis capture means for use with any structure allows people to be held in the optimal posture for long periods of time. This improves the experiences of people traveling by airplane by helping them avoid the discomfort of long-term sitting. This could improve the experience of people at events since they can be closer to whatever is going on. This could reduce trucker accidents, especially long-haul truckers (not to mention the potential for dramatically improving their health). Thus, the means to capture the pelvis is very powerful to support proper body posture and the optimal performance of the body's basic functions. Also, the means to capture the weight of an individual through the pelvis is very comfortable and through this means standing, even for long periods of time, can be more comfortable than sitting. The body has the benefit of operating more efficiently so that energy can go to other activities such as physical (using hands and upper body to accomplish tasks) and mental tasks (office work, as an example). Additionally because the legs do not get fatigued body does not need to stop, sit or rest so much. This shows potential for great gains in productivity and for longer periods of activity without straining or fatiguing the body. For walking, this means users can go much further before reaching fatigue.

The frames and support form with the pelvis capture means can be used as a separate unit completely isolated from the frame itself. So, any structure can now be designed to make use of the disclosed pelvis captured means for any of many other situations including transportation (autos, airplanes, buses, trains, etc.), entertainment (auditorium, theater, stadium, etc.), furniture (rolling or stationary, occupational or home use, etc.), rehabilitation/exercise (treadmill, gait trainers, strength training, etc.)

Some other anecdotal evidence from user trials include: because there pelvis capture means creates a new "base platform" frame of reference, the brain can solve challenges of gait and the movement of the legs from the challenges of posture of the upper body. Users brains quickly use this new base platform to self correct hair problems and postural problems. The device helps the brain relearn proper gait and proper posture. Even when the user isn't using the device, the gait and posture remains improved. So the pelvis support helps retrain the brain for the long term.

Another aspect of the pelvis capture is that this allows the user to avoid the degradation of the body inherent from the use of current working mobility devices. Current walking mobility devices actually lead users to further degradation in gait and in posture because they do not use the pelvis capture means to secure the user. They actually promote bad posture and improper gait because the user's center of gravity is not contained within the bounds of the device so people tend to lean forward, becoming progressively stooped with head dropping downward. This leads to many unintended posture and gait related problems over extended periods of time. Over the past several years I've witnessed remarkable recovery of capabilities for device users because of the pelvis capture means users in the device. The system supports any and all applications where standing is desirable; where people want to avoid excess sitting; and when they want to avoid the inherent health degrading characteristics of other mobility devices, including both wheelchairs and walking assistive devices. Various applications of the embodiments have found advantages that may include one or more of the following:

that capturing the pelvis and keeping it stabilized helps the brain to separate the challenges of walking from the challenges of posture. The pelvis replaces the get as the reference point from which the brain addresses challenges with standing and walking. The brain in many individuals seems to rapidly learn from information received using the device and naturally works to improve gait and improve upper body posture. The means of securing the user's pelvis helps realign the user's posture into a better posture. Initial testing shows that users with more severe challenges benefit from professional therapy and can make extraordinary progress in a matter of weeks of once or twice weekly professional sessions. One spinal cord injury patient re-learned proper gait and good posture by using the device over a two-week period. It seemed to become imprinted into his brain so that even when he was no longer in the device, his gait and posture remained improved. A couple of weeks later, the same individual showed up at therapy with his horse's saddle—using the device to carry it into the session. A remarkable feat that would have been inconceivable just weeks earlier.

that many people with pain due to improper gait and/or improper posture have marked reduction of pain symptoms when they use the device because of the ability of the device to improve gait and posture. In some cases, the reduction in pain is near 100%. One woman with cerebral palsy suffered excruciating pain when she walked ordinarily. Within minutes of using the device, her gait and posture were corrected and the pain was gone She went on to stand and walk in comfort for over an hour with no need to sit down for a rest.

that for people with balance problems the device can allow them to stand and walk with reduced fear of falling. One 53 year-old individual with cerebral palsy and severe balance problems had never stood or walked hands free in his life, he did so using the device within a minute. He stayed in the device standing and walking for nearly 4 hours while experiencing no pain and using his hands to gesture as he spoke rather than to hold on. He refused to get out of the device because of how good it felt fit him to be comfortably standing. A 60 year old woman with cerebral palsy with even more severe balance problems began walking hands free within a couple of minutes. She repeatedly "tried to fall" but the device prevented her from doing so.

that the many people who have been using wheelchairs even for decades can stand and walk with the device. One man with muscular dystrophy has been wheelchair bound for over 40 years. Within a minute of getting into the device he walked about 30 feet, turned around, and walked back to where he started. Two women with spinal cord injuries who have been wheelchair bound for more than 20 years each were able to stand and walk within minutes of being in the device. Because of their long term confinement to wheelchairs, these individuals have atrophied muscles and in the cases of the women with spinal cord injuries the control of leg movement is limited. Nonetheless, all now seem capable to regain the ability to walk given adequate personal motivation with extensive training and rehabilitation.

that standing in using this device can be as comfortable as sitting for many people. This, we believe, will encourage users to be more active. Many trial users have used the device to stand and move comfortably for extended periods of time without experiencing the fatigue typical of standing for long durations. Several people have used the device to stand and move for over 6 hours continuously and reported no fatigue and no desire to sit down. They found the devise to enable standing for long periods to be as comfortable as sitting.

That people with mobility challenges are often most interested in standing and moving with their hands free in order to do typical ordinary activities of daily living. Walking long distances or over rough terrain is a secondary interest. They are frustrated that they do not have a device that allows them to stand with their hands free to use their kitchens, push a grocery cart and select their own groceries and generally be enabled to stand and use their hands. People who have tried the device report that they can cook meals for themselves and others, grocery shop and even play pool!

Additionally, and for example, by remaining mobile in a standing or partially standing posture, the individual may be able to avoid the retrofit of the individual's kitchen, office or other facilities for wheelchair accessibility. In many cases, it is anticipated that the individual will be able to make use of standard appliances, restrooms and other conveniences taken for granted by others without mobility impairments. There are many other tangible and intangible benefits of this preferred embodiment as compared to the currently available mobility assistance devices.

The preferred embodiment provides for multiple means to allow the individual to retain a standing or partially standing posture while being securely held in and actively operating the mobility assistance device. A harness and walking seat with belt are depicted in the disclosure as examples, but other equivalent means are available. Additionally, the preferred embodiment provides for multiple designs for the structural elements to allow for other means to transfer the individual's weight through the device to the ground or floor. None should be considered as limiting the preferred embodiment from other structural designs.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The preferred embodiment should therefore not be limited by the above described embodiments, method, and examples, but by all embodiments and methods within the scope and spirit of the preferred embodiment.

What is claimed is:

1. A mobility assistance apparatus, comprising:
   first and second frames positioned on left and right sides of a user;
   a hinge arm mechanism coupled to the first and second frames; and
   a securing unit coupled to the frames to transfer at least a portion of the user's body weight from the legs and to transfer weight through the user's hip or pelvis to the first and second frame enabling the user to stand or work on a working surface for an extended period without requiring the user's arms to hold the frame.

2. The apparatus of claim 1, walking seat comprising two seat pans mounted on a seat frame, each supporting a corresponding side of the buttocks, each of the seat pans independently pivoting around a horizontal axis while the user walks.

3. The apparatus of claim 1, wherein each frame comprises a height adjuster to adjust a frame height to fit the user.

4. The apparatus of claim 3, wherein the height adjuster comprises a manual extender with a core and a plurality of openings to select height, or the height adjuster comprises a motorized extender.

5. The apparatus of claim 4, wherein the motorized extender comprises a linear actuator or a pneumatic pump.

6. The apparatus of claim 1, wherein the hinge arm is foldable and comprises three hinge points: one on a seat support and two points each to be connected to one of the first and second frames.

7. The apparatus of claim 1, wherein each frame has one or more non-moving foot or locked wheels when stationary.

8. The apparatus of claim 7, comprising a first wheel that swivels 360 degrees around a vertical axis and a second wheel that does not swivel.

9. The apparatus of claim 7, comprising a brake assembly coupled to the one or more wheels and controlled by the user to stop movement.

10. The apparatus of claim 7, wherein at least one wheel is motorized.

11. The apparatus of claim 1, comprising a joystick or a smartphone application to receive direction command, a display to provide visual feedback, and a processor coupled to the joystick or a smartphone and the display to guide the user.

12. The apparatus of claim 1, comprising an obstacle warning system.

13. The apparatus of claim 1, comprising buttons to select move forward, move backward, turn right, turn left, and brake.

14. The apparatus of claim 1, wherein the frame members are of identical design and interchangeable.

15. The apparatus of claim 1, wherein the frames and the hinge arm are collapsible.

16. The apparatus of claim 1, comprising a seat height adjuster including an air spring used for seat height adjustment.

17. The apparatus of claim 1, comprising one or more shock absorbers to smooth out rough surface rides.

18. The apparatus of claim 1, comprising a walking seat positioned on the hinge arm to receive the user at a predetermined point and a belt to secure the user to the walking seat, the walking seat and belt operate in concert with each other to transfer weight from the user's legs, and wherein the walking seat has a predetermined shape providing clearance for leg motion.

19. The apparatus of claim 1, comprising functional electrical stimulation electrodes coupled to leg muscles and actuated by a user to move forward or backward.

20. The apparatus of claim 1, comprising attachment arms coupled to the hinge arm mechanism or to the first or the second frames.

21. The apparatus of claim 1, wherein the securing unit comprises two flippers each coupled to one frame.

22. The apparatus of claim 1, wherein the securing unit comprises two grasping devices each coupled to one frame.

23. The apparatus of claim 1, wherein the securing unit comprises a harness or cable coupled to the frames.

24. The apparatus of claim 1, comprising a seat assembly with belt and buckle integrated therein.

25. The apparatus of claim 1, comprising a treadmill coupled to the frame.

26. The apparatus of claim 1, comprising attachment arms coupled to the frame.

27. The apparatus of claim 1, wherein the securing unit is used in a transportation vehicle, an auditorium, a theater, a stadium, a rolling furniture, a stationary furniture, or an exercise machine.

* * * * *